(12) United States Patent
Yoshida

(10) Patent No.: US 8,744,563 B2
(45) Date of Patent: Jun. 3, 2014

(54) MENTAL DISORDER ANALYSIS APPARATUS, MENTAL DISORDER ANALYSIS METHOD, AND PROGRAM

(75) Inventor: Masaki Yoshida, Osaka (JP)

(73) Assignee: Sleepwell Co., Ltd., Osaka (JP)

( * ) Notice: Subject to any disclaimer, the term of this patent is extended or adjusted under 35 U.S.C. 154(b) by 0 days.

(21) Appl. No.: 13/825,011

(22) PCT Filed: Jun. 20, 2012

(86) PCT No.: PCT/JP2012/065703
§ 371 (c)(1),
(2), (4) Date: Mar. 18, 2013

(87) PCT Pub. No.: WO2012/176790
PCT Pub. Date: Dec. 27, 2012

(65) Prior Publication Data
US 2013/0218043 A1 Aug. 22, 2013

(30) Foreign Application Priority Data
Jun. 21, 2011 (JP) .................................. 2011-137741

(51) Int. Cl.
*A61B 5/04* (2006.01)

(52) U.S. Cl.
USPC ........................................................ 600/544

(58) Field of Classification Search
USPC ................................................. 600/544, 545
See application file for complete search history.

(56) References Cited

U.S. PATENT DOCUMENTS

| | | | |
|---|---|---|---|
| 6,430,443 B1 * | 8/2002 | Karell .............................. | 607/55 |
| 8,425,583 B2 * | 4/2013 | Nofzinger ..................... | 607/109 |
| 2001/0003145 A1 | 6/2001 | Mori et al. | |
| 2004/0116791 A1 | 6/2004 | Miyauchi | |
| 2009/0082691 A1 * | 3/2009 | Denison et al. ................ | 600/544 |
| 2010/0042011 A1 * | 2/2010 | Doidge et al. ................ | 600/544 |

FOREIGN PATENT DOCUMENTS

| | | |
|---|---|---|
| JP | S58-78647 A | 5/1983 |
| JP | 2001-161652 A | 6/2001 |
| JP | 2004-173887 A | 6/2004 |

OTHER PUBLICATIONS

Kajimura, Naofumi, "Insomnia in senility. Features of sleep disorder in senile functional diseases (depression and hallucination paranoid state)", Japanese Journal of Geriatric Psychiatry, vol. 10, No. 4, Apr. 1999, 431 to 437.

Nishida, Masaki, "Suimin Noha nite Hyoka shita Kibun Shogai no Suimin Jotai Oyobi Suimin Kozo ni Tsuite'", Suimin Iryo, vol. 5, No. 2, 2011, 222 to 224.

Uchiyama, Makoto, "Suimin to Utsubyo", Journal of Clinical and Experimental Medicine, vol. 219, No. 13, Dec. 20, 2006 (Dec. 30, 2006), 1075 to 1079.

International Search Report, dated Sep. 18, 2012, which issued during the prosecution of International Patent Application No. PCT/JP2012/065703, of which the present application is the national phase.

* cited by examiner

*Primary Examiner* — Navin Natnithithadha
*Assistant Examiner* — Etsub Berhanu
(74) *Attorney, Agent, or Firm* — Troutman Sanders LLP

(57) ABSTRACT

A mental disorder analysis apparatus includes a storage portion in which sleep electroencephalogram information, which is information on electroencephalograms during sleep of a test subject, is stored, an analyzing portion that performs analysis regarding presence or absence of a mental disorder using the sleep electroencephalogram information stored in the storage portion, and an output portion that outputs a result of the analysis performed by the analyzing portion.

21 Claims, 34 Drawing Sheets

FIG.11

| Test subject name | Sleep electroencephalogram information |
|---|---|
| Kimura A | EEGDATA01 |
| Kinoshita B | EEGDATA02 |
| Sakamoto C | EEGDATA03 |
| Yokoyama D | EEGDATA04 |
| ⋮ | ⋮ |

FIG.12

| Start time (HH:MI:SS) | End time (HH:MI:SS) |
|---|---|
| 22:00:10 | 22:00:12 |
| 22:00:18 | 22:00:22 |
| 22:00:32 | 22:00:34 |
| 22:00:37 | 22:00:40 |
| 22:00:49 | 22:00:51 |
| 22:01:10 | 22:01:12 |
| ⋮ | ⋮ |

FIG.13

| Start time (HH:MI:SS) | $\alpha$ Power ($\mu V^2$) |
|---:|---:|
| 22:00:00 | 1.5 |
| 22:00:30 | 1.6 |
| 22:01:00 | 1.8 |
| 22:01:30 | 2.1 |
| 22:02:00 | 2 |
| 22:02:30 | 2.3 |
| 22:03:00 | 1.9 |
| 22:03:30 | 1.5 |
| 22:04:00 | 1.2 |
| 22:04:30 | 1.3 |
| 22:05:00 | 1.2 |
| 22:05:30 | 1.7 |
| 22:06:00 | 1.9 |
| 22:06:30 | 1.7 |
| 22:07:00 | 1.8 |
| 22:07:30 | 1.9 |
| 22:08:00 | 2.1 |
| 22:08:30 | 2.3 |
| 22:09:00 | 2.1 |
| 22:09:30 | 1.4 |

FIG.34

| Time (sec) | Output (µV) |
|---|---|
| 0.001 | 5.12 |
| 0.005 | 4.37 |
| 0.009 | 4.26 |
| 1.013 | 3.79 |
| 1.017 | 3.55 |
| 1.021 | 3.21 |
| ⋮ | ⋮ |

MENTAL DISORDER ANALYSIS APPARATUS, MENTAL DISORDER ANALYSIS METHOD, AND PROGRAM

CROSS-REFERENCE TO RELATED APPLICATIONS

This is a U.S. national phase application under 35 U.S.C. §371 of International Patent Application No. PCT/JP2012/065703, filed on Jun. 20, 2012, and claims benefit of priority to Japanese Patent Application No. 2011-137741, filed on Jun. 21, 2011. The International Application was published on Dec. 27, 2012, as International Publication No. WO 2012/176790 under PCT Article 21(2). The entire contents of these applications are hereby incorporated herein by reference.

TECHNICAL FIELD

The present invention relates to apparatuses and the like for analyzing information on electroencephalograms during sleep and diagnosing a mental disorder.

BACKGROUND ART

As a conventional mental disorder analysis apparatus, an apparatus is known that can solve disadvantages in medical interview techniques and accurately diagnose a mental disorder, using brain activity diagnostic information acquired by analyzing α wave signals and β wave signals in electroencephalogram (EEG) signals and calculating a ratio of integral values of the β wave signals with respect to integral values of the α wave signals, or by obtaining integral values of complex electroencephalogram signals, α wave signals, and β wave signals for a predetermined number of times of sampling and calculating a ratio of β% with respect to α%, where α% indicates a ratio of integral values of the α wave signals generated with respect to integral values of the complex electroencephalogram signals, and β% indicates a ratio of integral values of the β wave signals generated with respect to integral values of the complex electroencephalogram signals (see Patent Document 1, for example).

CITATION LIST

Patent Document

[Patent Document 1] JP 2001-161652A (p. 1, FIG. 1, etc.)

However, since such a conventional mental disorder analysis apparatus uses information obtained from electroencephalograms during non-sleep times such as while a test subject is awake or at rest, the external environment, consciousness or thoughts, and the like of the test subject during the electroencephalogram measurement act on the electroencephalograms, and, thus, the waveform and the like resulting from these factors are included in the measured electroencephalograms, which leads to a problem that a mental disorder of the test subject cannot be properly diagnosed. For example, during non-sleep times, only if the test subject is sharply conscious of being under electroencephalogram measurement, his or her mental conditions may be different from those in a normal state, and, thus, abnormal electroencephalograms may be measured, which leads to a problem that the diagnosis cannot be accurately performed.

SUMMARY

The present invention is directed to a mental disorder analysis apparatus, including: a storage portion in which sleep electroencephalogram information, which is information on electroencephalograms during sleep of a test subject, is stored; an analyzing portion that performs analysis regarding presence or absence of a mental disorder using the sleep electroencephalogram information stored in the storage portion; and an output portion that outputs a result of the analysis performed by the analyzing portion.

With this configuration, it is possible to determine the presence or absence of a mental disorder, using the electroencephalogram information measured during sleep, and to properly diagnose a mental disorder by reducing, to the extent possible, the influence on electroencephalograms from an external environment or the like of a test subject during the electroencephalogram measurement.

Furthermore, in the mental disorder analysis apparatus according to the present invention, as the analysis, the analyzing portion acquires information indicating an appearance status of electroencephalogram information at a predetermined specific frequency contained in the sleep electroencephalogram information, and determines the presence or absence of a mental disorder according to the information, and the output portion outputs a result of the determination regarding the presence or absence of a mental disorder performed by the analyzing portion.

With this configuration, it is possible to properly diagnose a mental disorder using a change in an appearance status of electroencephalogram information at a specific frequency during sleep, resulting from a mental disorder.

Furthermore, in the mental disorder analysis apparatus according to the present invention, the analyzing portion acquires information indicating an appearance status of any of α waves, δ waves, and β waves contained in the sleep electroencephalogram information, and determines the presence or absence of a mental disorder according to the information.

With this configuration, it is possible to properly diagnose a mental disorder using a change in an appearance status of α waves, δ waves, or β waves during sleep, resulting from a mental disorder.

Furthermore, in the mental disorder analysis apparatus according to the present invention, the analyzing portion acquires information indicating either one of an appearance rate and a power of α waves contained in sleep electroencephalogram information in a non-REM sleep period, in the sleep electroencephalogram information, and determines the presence or absence of a mental disorder according to the information.

With this configuration, it is possible to determine the presence or absence of a mental disorder, based on a change in an appearance rate or a power of α waves in a non-REM sleep period.

Furthermore, in the mental disorder analysis apparatus according to the present invention, the analyzing portion detects spindle waves in an a band in sleep electroencephalogram information in a non-REM sleep period, in the sleep electroencephalogram information, and determines that depression is present in a case where an appearance rate of the detected spindle waves exceeds a predetermined threshold value.

With this configuration, it is possible to determine whether or not depression is present, based on a change in an appearance status of spindle waves in α wave band in a non-REM sleep period.

Furthermore, in the mental disorder analysis apparatus according to the present invention, the analyzing portion performs Fourier transform to detect an α wave component in each of multiple periods forming a non-REM sleep period in the sleep electroencephalogram information, and determines that depression is present in a case where an appearance rate of periods in which the α wave component is detected exceeds a predetermined threshold value.

With this configuration, it is possible to determine whether or not depression is present, based on an appearance rate of α waves in a non-REM sleep period.

Furthermore, in the mental disorder analysis apparatus according to the present invention, the analyzing portion performs Fourier transform to detect an α wave component in each of at least one period forming a non-REM sleep period in the sleep electroencephalogram information, and determines that depression is present in a case where any detected α wave component has a power exceeding a predetermined threshold value.

With this configuration, it is possible to determine whether or not depression is present, based on a power of α waves in a non-REM sleep period.

Furthermore, in the mental disorder analysis apparatus according to the present invention, the analyzing portion acquires information indicating either one of an appearance rate and a power of δ waves contained in sleep electroencephalogram information in a non-REM sleep period, in the sleep electroencephalogram information, and determines the presence or absence of a mental disorder according to the information.

With this configuration, it is possible to determine the presence or absence of a mental disorder, based on a change in an appearance rate or a power of δ waves in a non-REM sleep period.

Furthermore, in the mental disorder analysis apparatus according to the present invention, the analyzing portion performs Fourier transform to detect a δ wave component in each of multiple periods forming a non-REM sleep period in the sleep electroencephalogram information, and determines that depression is not present in a case where an appearance rate of periods in which the δ wave component is detected exceeds a predetermined threshold value.

With this configuration, it is possible to determine whether or not depression is present, based on an appearance rate of δ waves in a non-REM sleep period.

Furthermore, in the mental disorder analysis apparatus according to the present invention, the analyzing portion performs Fourier transform to detect a δ wave component in each of at least one period forming a non-REM sleep period in the sleep electroencephalogram information, and determines that depression is not present in a case where any detected δ wave component has a power exceeding a predetermined threshold value.

With this configuration, it is possible to determine whether or not depression is present, based on a power of δ waves in a non-REM sleep period.

Furthermore, in the mental disorder analysis apparatus according to the present invention, the analyzing portion acquires information indicating either one of an appearance rate and a change in a waveform size of β waves contained in sleep electroencephalogram information in a REM sleep period, in the sleep electroencephalogram information, and determines the presence or absence of a mental disorder according to the information.

With this configuration, it is possible to determine the presence or absence of a mental disorder based on information indicating an appearance rate or a change in a waveform size of β waves in a REM sleep period.

Furthermore, in the mental disorder analysis apparatus according to the present invention, the analyzing portion performs Fourier transform to detect a β wave component in each of multiple periods forming a REM sleep period in the sleep electroencephalogram information, and determines that depression is present in a case where an appearance rate of periods in which the β wave component is detected exceeds a predetermined threshold value.

With this configuration, it is possible to determine whether or not depression is present, based on an appearance rate of β waves in a REM sleep period.

Furthermore, in the mental disorder analysis apparatus according to the present invention, the analyzing portion acquires a difference between amplitudes of adjacent waves in β waves in each of at least one period forming a REM sleep period in the sleep electroencephalogram information, and determines that depression is present in a case where any acquired difference between the amplitudes exceeds a predetermined threshold value.

With this configuration, it is possible to determine whether or not depression is present, based on information indicating a change in a waveform size of β waves in a REM sleep period.

Furthermore, the mental disorder analysis apparatus according to the present invention further includes a medication determining portion that acquires information indicating an appearance status of γ waves contained in the sleep electroencephalogram information stored in the storage portion, and determines whether or not drug administration has been performed for a mental disorder according to the information, wherein the output portion further outputs a result of the determination performed by the medication determining portion.

With this configuration, it is possible to determine whether or not drug administration has been performed for a mental disorder.

Furthermore, in the mental disorder analysis apparatus according to the present invention, the analyzing portion acquires at least two pieces of information from among: information indicating either one of an appearance rate and a power of α waves contained in sleep electroencephalogram information in a non-REM sleep period, in the sleep electroencephalogram information; information indicating either one of an appearance rate and a power of δ waves contained in sleep electroencephalogram information in a non-REM sleep period, in the sleep electroencephalogram information; and information indicating either one of an appearance rate and a change in a waveform size of β waves contained in sleep electroencephalogram information in a REM sleep period, in the sleep electroencephalogram information; and determines the presence or absence of a mental disorder according to a combination of the acquired pieces of information.

With this configuration, it is possible to more accurately diagnose a mental disorder.

Furthermore, in the mental disorder analysis apparatus according to the present invention, the analyzing portion acquires electroencephalogram information at least one predetermined specific frequency from the sleep electroencephalogram information, and the output portion outputs the sleep electroencephalogram information at the specific frequency acquired by the analyzing portion.

With this configuration, for example, it is possible to use sleep electroencephalogram information at a specific frequency, for example, to diagnose a mental disorder.

Furthermore, in the mental disorder analysis apparatus according to the present invention, the output portion outputs the sleep electroencephalogram information at the specific frequency acquired by the analyzing portion, and the sleep electroencephalogram information from which said sleep electroencephalogram information has been acquired.

With this configuration, for example, it is possible to diagnose a mental disorder and the like, using sleep electroencephalogram information, and sleep electroencephalogram information at a specific frequency acquired therefrom.

Furthermore, in the mental disorder analysis apparatus according to the present invention, the analyzing portion acquires electroencephalogram information at least two predetermined specific frequencies from the sleep electroencephalogram information, and the output portion outputs the sleep electroencephalogram information at the at least two specific frequencies acquired by the analyzing portion.

With this configuration, for example, it is possible to accurately diagnose a mental disorder by referring to sleep electroencephalogram information at different frequencies.

Furthermore, in the mental disorder analysis apparatus according to the present invention, the analyzing portion acquires information indicating an appearance status of electroencephalogram information at a predetermined specific frequency from the sleep electroencephalogram information, and the output portion outputs the information indicating the appearance status acquired by the analyzing portion.

With this configuration, it is possible to use an appearance status of sleep electroencephalogram information at a specific frequency, for example, to diagnose a mental disorder.

Furthermore, in the mental disorder analysis apparatus according to the present invention, the mental disorder is depression.

With this configuration, it is possible to properly diagnose depression.

Furthermore, the present invention is directed to an electroencephalogram information output apparatus, including: a healthy electroencephalogram storage portion in which healthy electroencephalogram information, which is information on electroencephalograms during sleep of a healthy person, is stored; a disordered electroencephalogram storage portion in which disordered electroencephalogram information, which is information on electroencephalograms during sleep of a patient with a mental disorder, is stored; and an output portion that outputs a waveform indicated by the healthy electroencephalogram information and a waveform indicated by the disordered electroencephalogram information in juxtaposition.

With this configuration, it is possible to output information useful when diagnosing a mental disorder using the electroencephalogram information, and to reduce dispersion in diagnostic results of a mental disorder. For example, it is possible to easily compare the electroencephalogram of a test subject with the electroencephalogram of a healthy person and the electroencephalogram of a patient with a mental disorder, and to easily and accurately determine the presence or absence of a mental disorder.

Furthermore, the electroencephalogram information output apparatus according to the present invention further includes an accepting portion that accepts test subject electroencephalogram information, which is information on electroencephalograms during sleep of a test subject, wherein the output portion further outputs, a test subject electroencephalogram, which is a waveform indicated by the test subject electroencephalogram information, in juxtaposition with a healthy electroencephalogram and a disordered electroencephalogram.

With this configuration, it is possible to easily compare the electroencephalogram of a test subject, the electroencephalogram of a healthy person, and the electroencephalogram of a patient with a mental disorder, and to easily and accurately determine whether or not the test subject has a mental disorder.

Furthermore, in the electroencephalogram information output apparatus according to the present invention, the disordered electroencephalogram information is information on electroencephalograms of a patient with depression.

With this configuration, it is possible to easily and accurately determine whether or not the test subject is a patient with depression.

Furthermore, the present invention is directed to a mental disorder diagnostic sheet that is output by the electroencephalogram information output apparatus, wherein waveforms respectively indicating the healthy electroencephalogram information and the disordered electroencephalogram information are displayed in juxtaposition.

With this configuration, it is possible to easily compare the electroencephalogram of a test subject with the electroencephalogram of a healthy person and the electroencephalogram of a patient with a mental disorder, to easily and accurately determine the presence or absence of a mental disorder, and to reduce dispersion in diagnostic results when diagnosing a mental disorder using the electroencephalogram information.

Furthermore, in the mental disorder diagnostic sheet that is output by the electroencephalogram information output apparatus according to the present invention, wherein waveforms respectively indicating the healthy electroencephalogram information, the disordered electroencephalogram information, and the test subject electroencephalogram information are displayed in juxtaposition.

With this configuration, it is possible to easily compare the electroencephalogram of a test subject, the electroencephalogram of a healthy person, and the electroencephalogram of a patient with a mental disorder, and to easily and accurately determine whether or not the test subject has a mental disorder.

Furthermore, in the mental disorder diagnostic sheet according to the present invention, a healthy electroencephalogram, which is a waveform indicating healthy electroencephalogram information, which is information on electroencephalograms during sleep of a healthy person, and a disordered electroencephalogram, which is a waveform indicating disordered electroencephalogram information, which is information on electroencephalograms during sleep of a patient with a mental disorder, are displayed in juxtaposition.

With this configuration, it is possible to easily compare the electroencephalogram of a test subject with the electroencephalogram of a healthy person and the electroencephalogram of a patient with a mental disorder, to easily and accurately determine the presence or absence of a mental disorder, and to reduce dispersion in diagnostic results when diagnosing a mental disorder using the electroencephalogram information.

Furthermore, in the mental disorder diagnostic sheet according to the present invention, wherein a test subject electroencephalogram, which is a waveform indicated by test subject electroencephalogram information, which is information on electroencephalograms during sleep of a test subject, is further displayed in juxtaposition with the healthy electroencephalogram and the disordered electroencephalogram.

With this configuration, it is possible to easily compare the electroencephalogram of a test subject, the electroencephalogram of a healthy person, and the electroencephalogram of a patient with a mental disorder, and to easily and accurately determine whether or not the test subject has a mental disorder.

Furthermore, in the mental disorder diagnostic sheet according to the present invention, the disordered electroencephalogram information is information on electroencephalograms of a patient with depression.

With this configuration, it is possible to easily and accurately determine whether or not the test subject is a patient with depression.

With the mental disorder analysis apparatus according to the present invention, it is possible to properly diagnose a mental disorder, using electroencephalograms during sleep.

With the electroencephalogram information output apparatus according to the present invention, it is possible to output information useful when diagnosing a mental disorder using the electroencephalogram information, and to reduce dispersion in diagnostic results of a mental disorder.

With the mental disorder diagnostic sheet according to the present invention, it is possible to reduce dispersion in diagnostic results when diagnosing a mental disorder using the electroencephalogram information.

BRIEF DESCRIPTION OF DRAWINGS

FIG. 11 is an electroencephalogram information management table of the mental disorder analysis apparatus according to this example.

FIG. 12 is an $\alpha$ spindle wave management table of the mental disorder analysis apparatus according to this example.

FIG. 13 is an $\alpha$ power management table of the mental disorder analysis apparatus according to this example.

FIG. 34 is a table showing exemplary healthy electroencephalogram information stored in the electroencephalogram information output apparatus.

DETAILED DESCRIPTION

Figure 1:
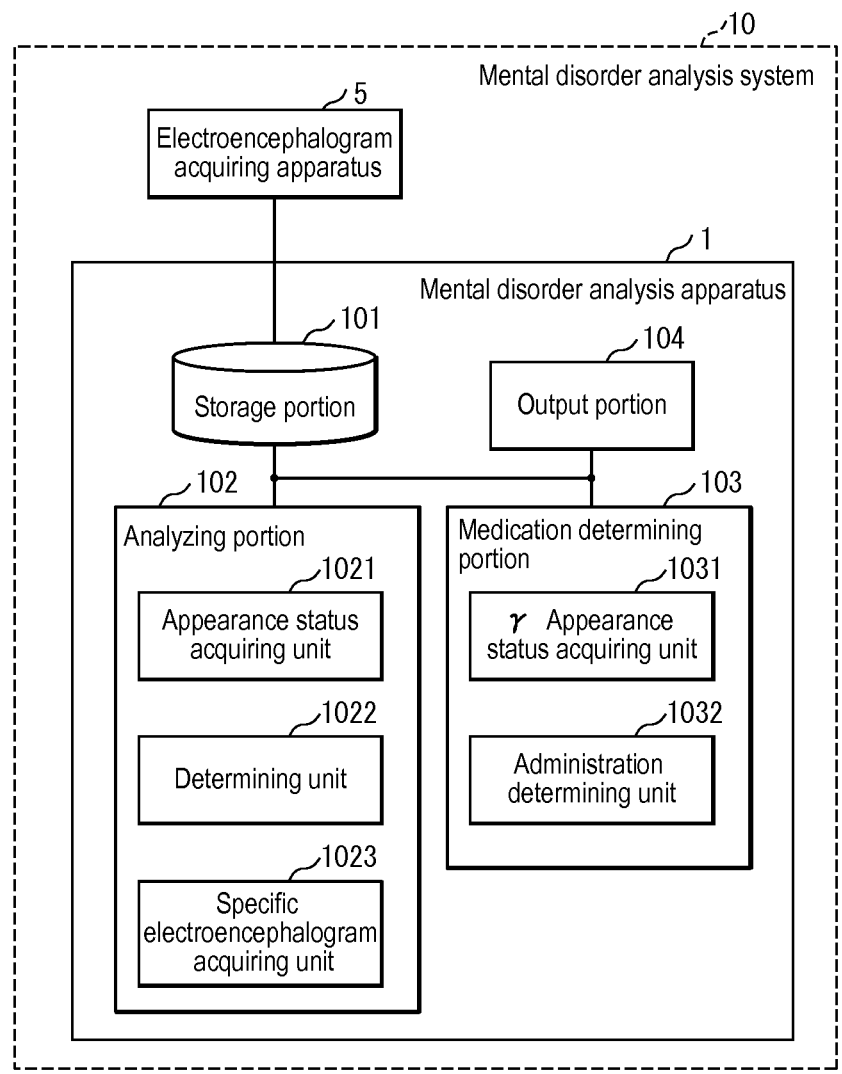
FIG. 1 is a block diagram of a mental disorder analysis system according to Example of the present invention.

Hereinafter, examples of a mental disorder analysis apparatus and the like will be described with reference to the drawings. Note that constituent elements denoted by the same reference numerals perform the same operations in the examples, and, thus, a description thereof may not be repeated.

EXAMPLE

The present invention is to analyze a mental disorder of a test subject using information on electroencephalograms measured during sleep of the test subject, in order to eliminate influences on the electroencephalograms given by the state or the environment of the test subject during the electroencephalogram measurement. In particular, the present invention is to analyze the presence or absence of a mental disorder of a test subject using electroencephalograms during sleep, utilizing a new finding on a relationship between the electroencephalograms during sleep of a healthy person and a mental disorder such as depression, which was obtained as a result of an in-depth study by the inventors.

FIG. 1 is a block diagram of a mental disorder analysis system 10 in this example.

The mental disorder analysis system 10 includes a mental disorder analysis apparatus 1 and an electroencephalogram acquiring apparatus 5.

The mental disorder analysis apparatus 1 includes a storage portion 101, an analyzing portion 102, a medication determining portion 103, and an output portion 104.

The analyzing portion 102 includes an appearance status acquiring unit 1021, a determining unit 1022, and a specific electroencephalogram acquiring unit 1023.

The medication determining portion 103 includes a γ appearance status acquiring unit 1031 and an administration determining unit 1032.

In the storage portion 101, sleep electroencephalogram information, which is information on electroencephalograms during sleep of a test subject, is stored. The information on electroencephalograms (hereinafter, referred to as "electroencephalogram information") is, for example, information indicating an electroencephalogram. For example, the electroencephalogram information is information indicating a power such as a voltage acquired from the brain in a time series. The sleep electroencephalogram information may be divided into one or more sections each in a period having a predetermined length called an epoch or the like. As the epoch, for example, a period having any length within approximately 30 to 60 seconds is set. Note that any seconds may be set as the length of the epoch, and there is no limitation on the length. Here, the epoch may be considered as a measurement time unit when measuring electroencephalograms or as a processing unit when performing calculation or the like of electroencephalograms. Each period called an epoch or the like may be associated, for example, with information on the start time or the end time of the period. Furthermore, each period may be associated with information indicating the acquisition order of the epoch, information for identifying the epoch, or the like. The sleep electroencephalogram information stored in the storage portion 101 may be electroencephalogram information in part of the sleep period of a test subject. For example, in the sleep electroencephalogram information, information only in a REM sleep period or a non-REM sleep period, or only partial information thereof may be stored in the storage portion 101. In the storage portion 101, electroencephalogram information containing the sleep electroencephalogram information may be stored. For example, in the storage portion 101, electroencephalogram information during sleep and electroencephalogram information before or after sleep may be stored.

Figure 2:
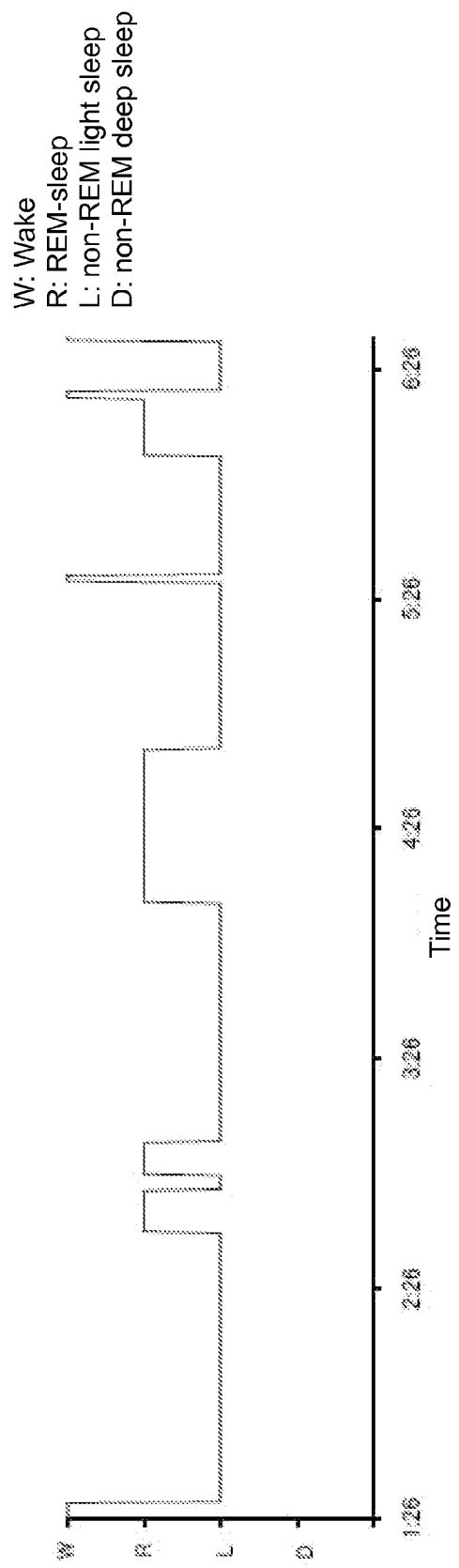
FIG. 2 is a schematic graph of sleep electroencephalogram information stored in the mental disorder analysis apparatus according to this example.

FIG. 2 is a schematic graph of a sleep process in which the sleep state indicated by electroencephalogram information containing one piece of sleep electroencephalogram information stored in the storage portion 101 is shown in a time series. For example, in the graph, the portions indicated by "R", "L", and "D" correspond to the sleep electroencephalogram information. Note that this graph does not show the electroencephalogram information itself.

In the storage portion 101, for example, the sleep electroencephalogram information of a test subject is stored in association with identifying information of the test subject. The identifying information of a test subject is a name of the test subject, a number or a symbol allocated to the test subject, or the like. In the storage portion 101, sleep electroencephalogram information acquired by an electroencephalograph or the like may be stored as it is, or sleep electroencephalogram information at one or more specific frequencies may be stored. Here, the frequency may be considered as a frequency band. The sleep electroencephalogram information at a specific frequency refers to, for example, δ waves (0.5 to 4 Hz), α waves (8 to 12 Hz), β waves (18 to 30 Hz), γ waves (35 to 45 Hz), and the like.

There is no limitation on the procedure in which the sleep electroencephalogram information is accumulated in the storage portion 101. For example, the sleep electroencephalogram information may be accumulated via a storage medium, or the sleep electroencephalogram information transmitted via a communication line, a signal wire, or the like may be accepted via an accepting portion (not shown) or the like and accumulated in the storage portion 101. This example will be described using, as an example, a case in which the electroencephalogram information containing the sleep electroencephalogram information of a test subject acquired by the electroencephalogram acquiring apparatus 5 (described later) is accumulated in the storage portion 101. Note that the accumulation is a concept that also includes temporary storage. The storage portion 101 is preferably a non-volatile storage medium, but may be realized also as a volatile storage medium.

The analyzing portion 102 performs analysis regarding the presence or absence of a mental disorder using the sleep electroencephalogram information stored in the storage portion 101. Specifically, the sleep electroencephalogram information of one test subject is used to perform analysis regarding the presence or absence of a mental disorder of the test subject. Examples of the mental disorder include depression, schizophrenia, panic disorder, and the like. The analysis regarding the presence or absence of a mental disorder performed by the analyzing portion 102 is, for example, to determine the presence or absence of a mental disorder. Furthermore, a process in which information on electroencephalograms used to determine the presence or absence of a mental disorder is acquired from the sleep electroencephalogram information may be considered as the analysis regarding the presence or absence of a mental disorder using the sleep electroencephalogram information. For example, the analysis may be a process that acquires portions in the sleep electroencephalogram information related to the presence or absence of a mental disorder, values obtained by processing the sleep electroencephalogram information, or the like.

The analyzing portion 102 acquires, for example, information indicating an appearance status of electroencephalogram information at a predetermined specific frequency contained in the sleep electroencephalogram information. Then, the presence or absence of a mental disorder is determined according to the acquired information. The electroencephalogram information at a specific frequency may be considered as electroencephalogram information in a specific frequency band. The electroencephalogram information at a specific frequency refers to, for example, δ waves, α waves, β waves, γ waves, or the like as described above. For example, the analyzing portion 102 acquires information indicating an appearance status of α waves, δ waves, or β waves contained in the sleep electroencephalogram information, and determines the presence or absence of a mental disorder according to the information. The analyzing portion 102 performs the analysis, for example, using the electroencephalogram information at a frequency corresponding to an analysis content, in the sleep electroencephalogram information. Determining the presence or absence of a mental disorder may be considered as determining the possibility of the presence or absence of a mental disorder, determining the level of the possibility of the presence or absence, or the like.

The appearance status of the electroencephalogram information at a specific frequency is, for example, an appearance rate of the electroencephalogram information at a specific frequency, a status of the power of the electroencephalogram information at a specific frequency, a status of the amplitude of the electroencephalogram information at a specific frequency, a status of the waveform of the electroencephalogram information at a specific frequency being disordered or disturbed, or the like.

Furthermore, at the time of analysis, the analyzing portion 102 may use only the electroencephalogram information in a specific period corresponding to an analysis content, in the sleep electroencephalogram information. The specific period is, for example, a REM sleep period, a non-REM sleep period, or a period specified based on the time at which a person falls asleep, is awakened, or enters REM sleep, or the like. If the electroencephalogram information containing the sleep electroencephalogram information is stored in the storage portion 101, the analyzing portion 102 acquires the sleep electroencephalogram information, for example, from the electroencephalogram information. Furthermore, if the electroencephalogram information in a specific period in the sleep electroencephalogram information is used for the analysis, the analyzing portion 102 may acquire the electroencephalogram information in the specific period, for example, from the sleep electroencephalogram information stored in the storage portion 101. If the sleep electroencephalogram information in a specific period used for the analysis is stored in advance in the storage portion 101, the sleep electroencephalogram information in the specific period may be read. The sleep electroencephalogram information read by the analyzing portion 102 may be information in the unit of epoch described above. The process that acquires the sleep electroencephalogram information or the electroencephalogram information in a specific period such as a REM sleep period or a non-REM sleep period from the electroencephalogram information is known, for example, in JP 2004-173887A (Paragraph 0016, etc.), and, thus, a detailed description thereof has been omitted.

In this example, as an example, a case will be described in which the analyzing portion 102 includes the appearance status acquiring unit 1021 and the determining unit 1022, and uses these units to acquire information indicating an appearance status of α waves contained in the sleep electroencephalogram information in a non-REM sleep period, in the sleep electroencephalogram information, and to determine the presence or absence of a mental disorder according to the acquired information.

Furthermore, the analyzing portion 102 may acquire the electroencephalogram information at one or more, or two or more predetermined specific frequencies (frequency bands) from the sleep electroencephalogram information. The electroencephalogram information at one or more, or two or more specific frequencies can be acquired, for example, using a filter such as a bandpass filter. In this example, as an example, a case will be described in which the analyzing portion 102 includes the specific electroencephalogram acquiring unit 1023, and uses this unit to acquire the electroencephalogram information at one or more, or two or more specific frequencies (frequency bands).

The analyzing portion 102 may be realized typically as an MPU, a memory, or the like. Typically, the processing procedure of the analyzing portion 102 is realized by software, and the software is stored in a storage medium such as a ROM. Note that the processing procedure may be realized also by hardware (a dedicated circuit).

The appearance status acquiring unit 1021 acquires information indicating an appearance status of α waves contained in the sleep electroencephalogram information in a non-REM sleep period, in the sleep electroencephalogram information. For example, the appearance status acquiring unit 1021 acquires information indicating an appearance rate or a power of α waves contained in the sleep electroencephalogram information in a non-REM sleep period, in the sleep electroencephalogram information. Here, as an example, cases will be respectively described in which, in order to determine the presence or absence of depression, which is one type of mental disorder, the appearance status acquiring unit 1021 acquires (1) information indicating an appearance rate of spindle waves of α waves in a non-REM sleep period, (2) information indicating an appearance rate of α waves in a non-REM sleep period, and (3) a power of α waves in a non-REM sleep period.

(1) The Case in which an Appearance Rate of Spindle Waves of α Waves is Acquired Generally, in the electroencephalograms in a non-REM sleep period of a healthy person, a substantially spindle-shaped electroencephalogram pattern (waveform) in a frequency band of 12 to 14 Hz, which is called sleep spindle waves, is rhythmically and successively appears. Meanwhile, there are spindle waves in α wave band (hereinafter, "α spindle waves"), which are an electroencephalogram pattern having a shape similar to that of the sleep spindle waves, but having a frequency band different therefrom. As a result of an in-depth study by the inventors, a new finding was obtained that α spindle waves seldom appear in a non-REM sleep period of a healthy person, whereas α spindle waves very often appear in a non-REM sleep period of a patient with depression. The obtained finding was that, for example, if the sleep electroencephalogram information is composed of multiple epochs each in 30 seconds, the α spindle waves appear in almost all epochs in a non-REM sleep period.

Figure 3:
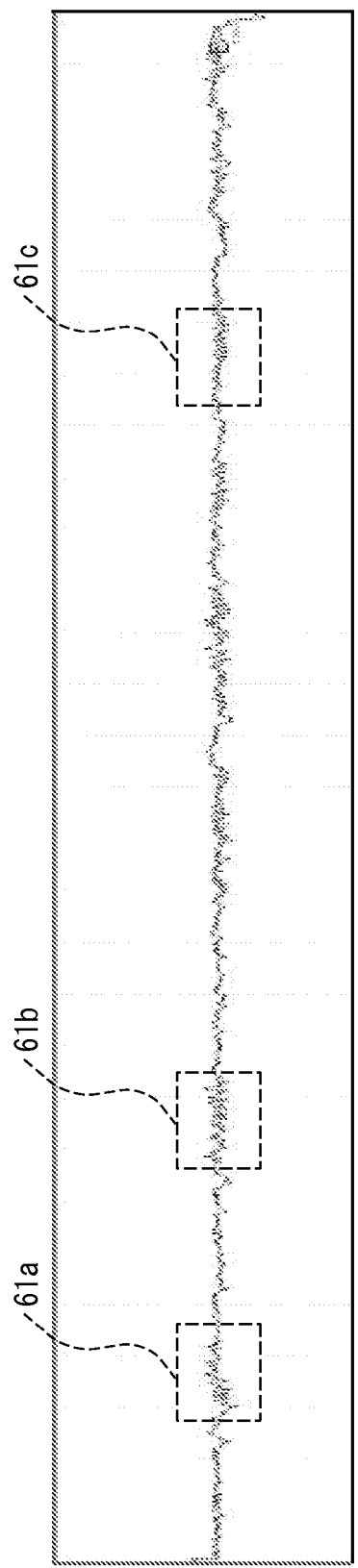
FIG. 3 is a graph showing an exemplary electroencephalogram of a patient with depression, illustrating the mental disorder analysis apparatus according to this example.

FIG. 3 is a graph showing an exemplary electroencephalogram in one epoch in a non-REM sleep period, in the sleep electroencephalogram information of a patient with depression.

Figure 4:
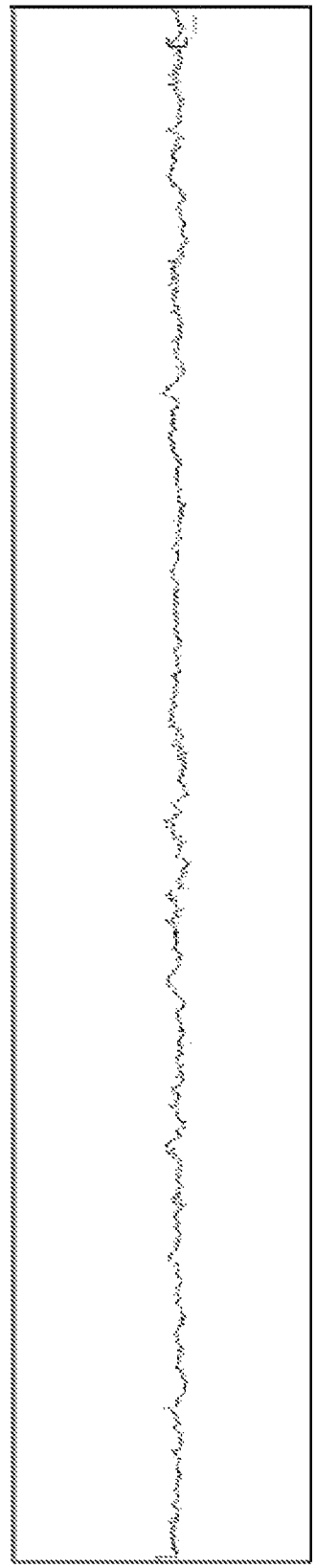
FIG. 4 is a graph showing an exemplary electroencephalogram of a healthy person, illustrating the mental disorder analysis apparatus according to this example.

FIG. 4 is a graph showing an exemplary electroencephalogram in one epoch in a non-REM sleep period, in the sleep electroencephalogram information of a healthy person.

As shown in FIG. 3, a large number of α spindle waves 61a to 61c appear in the electroencephalogram information in a non-REM sleep period of a patient with depression, whereas, as shown in FIG. 4, α spindle waves seldom appear in the electroencephalogram information in a non-REM sleep period of a healthy person.

Thus, the appearance status acquiring unit 1021 detects spindle waves in the α band in the sleep electroencephalogram information in a non-REM sleep period, in the sleep electroencephalogram information, and acquires information indicating an appearance rate of the spindle waves. The appearance status acquiring unit 1021 may detect spindle waves in the α band in predetermined part of a non-REM sleep period. For example, the appearance status acquiring unit 1021 detects α spindle waves, in a period having a predetermined length in a non-REM sleep period, or in a predetermined number of successive epochs. The α spindle waves have an electroencephalogram pattern similar to that of sleep spindle waves except for the frequency band. Accordingly, the α spindle waves can be acquired, for example, using similar processing for acquiring spindle waves as disclosed in JP S58-78647A, for example. Note that one α spindle wave has a length of, for example, 0.5 to 1.5 seconds.

The appearance status acquiring unit 1021 may take the number of detected α spindle waves, as the information indicating the appearance rate. Furthermore, for example, a value obtained by dividing the number of detected spindle waves with the number of epochs targeted for the detection or the length of period targeted for the detection may be taken as the information indicating the appearance rate. Furthermore, the appearance status acquiring unit 1021 may take the number of epochs in which one or more α spindle waves are detected in a predetermined number of epochs in a non-REM sleep period, or the ratio of this number of epochs with respect to a predetermined number, as the information indicating the appearance rate.

(2) The Case in which Information Indicating an Appearance Rate of α Waves is Acquired As described above, in the case of a patient with depression, α spindle waves often appear in a non-REM sleep period, and, thus, an appearance rate of the α waves in the non-REM sleep period is high.

Figure 5:
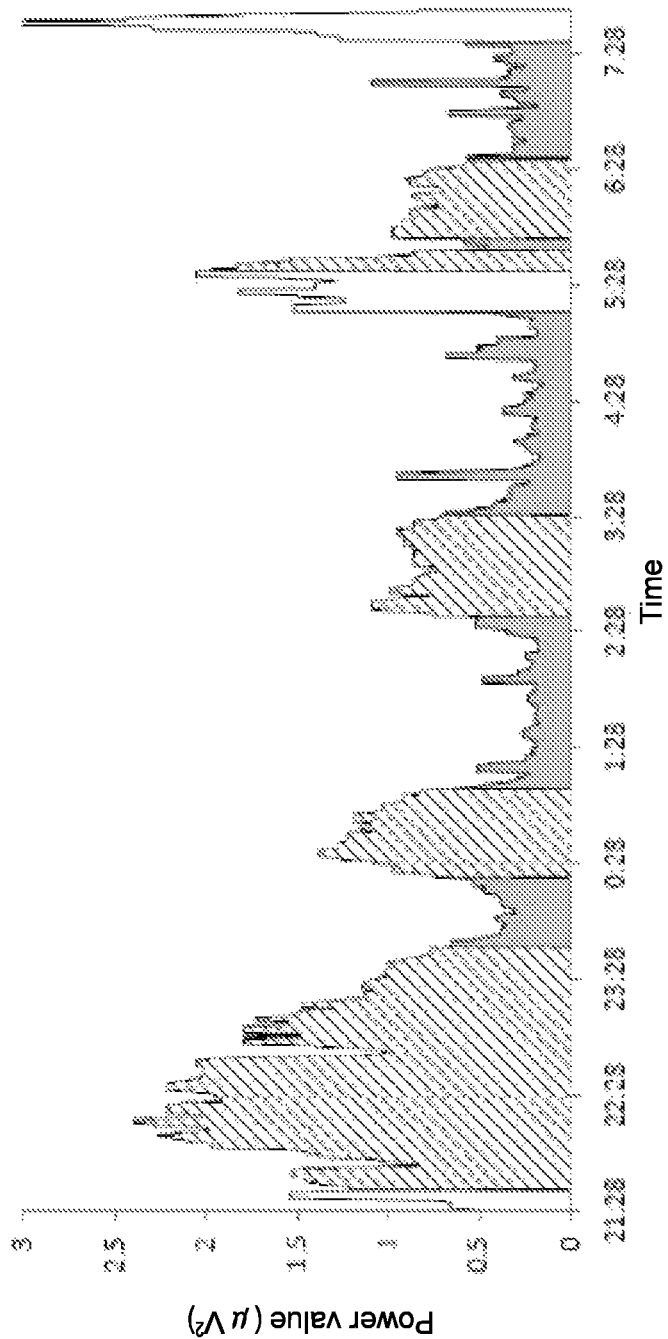
FIG. 5 is a graph showing the power of $\alpha$ waves, illustrating the mental disorder analysis apparatus according to this example.

FIG. 5 is an exemplary graph in which α wave peak values obtained by performing fast Fourier transform on the epochs of the sleep electroencephalogram information of a patient with depression are arranged in a time series. In the graph, a non-REM sleep period is indicated as a hatched portion.

Figure 6:
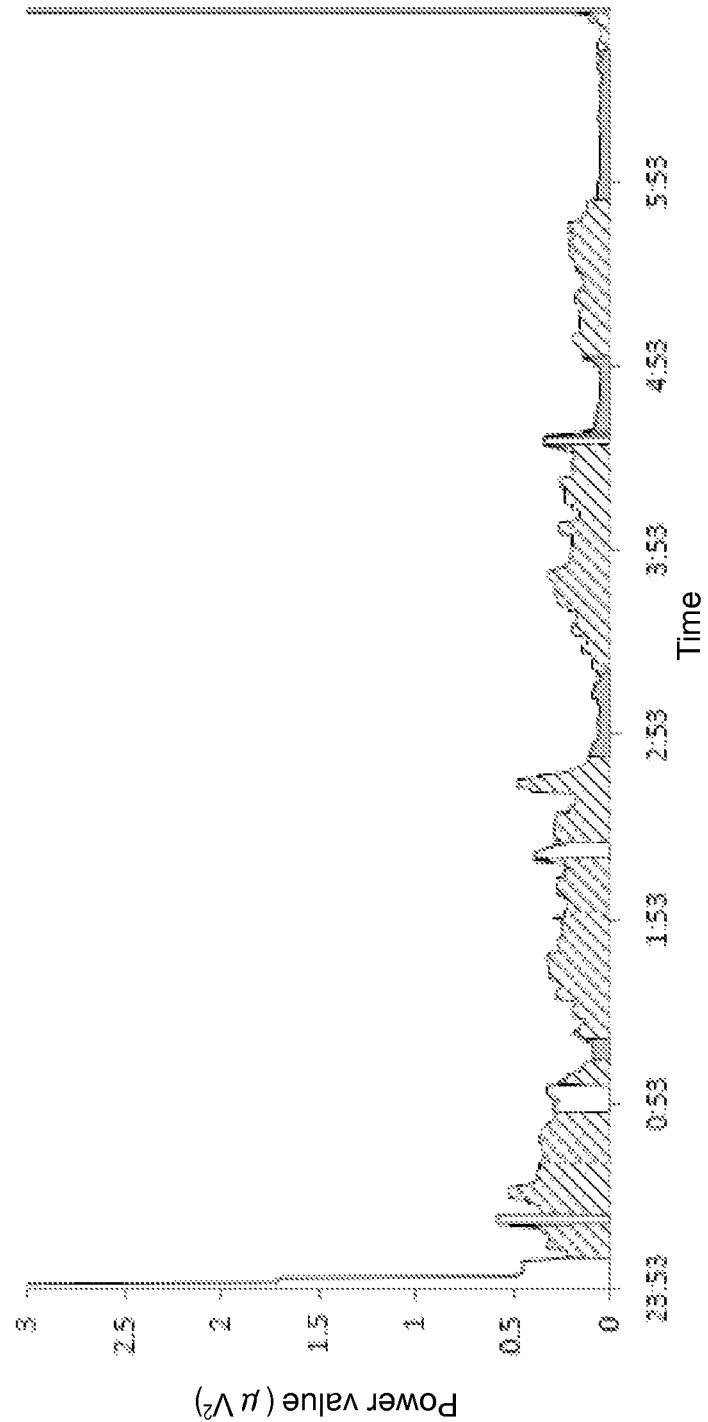
FIG. 6 is a graph showing the power of $\alpha$ waves, illustrating the mental disorder analysis apparatus according to this example.

Furthermore, FIG. 6 is an exemplary graph in which α wave peak values obtained by performing fast Fourier transform on the epochs of the sleep electroencephalogram information of a healthy person are arranged in a time series. In the graph, a non-REM sleep period is indicated as a hatched portion.

As clearly seen from FIGS. 5 and 6, a patient with depression has higher powers of α waves in a non-REM sleep period.

Thus, the appearance status acquiring unit 1021 acquires information indicating an appearance rate of α waves in the sleep electroencephalogram information in a non-REM sleep period, in the sleep electroencephalogram information. Here, as an example, the appearance status acquiring unit 1021 performs Fourier transform to detect an α wave component in each of multiple periods forming a non-REM sleep period in the sleep electroencephalogram information, and acquires information indicating an appearance rate of periods in which the α wave component is detected, as information indicating an appearance rate of α waves. The period in which an α wave component is detected may be considered as a period in which α waves at a predetermined threshold value or more are detected. The multiple periods forming a non-REM sleep period in the sleep electroencephalogram information may be multiple periods obtained by dividing a non-REM sleep period in order to perform Fourier transform, or may be periods such as epochs that have been divided in advance as described above. The periods preferably have the same length. For example, the appearance status acquiring unit 1021 performs Fourier transform on each of multiple predetermined periods (e.g., epochs) forming a non-REM sleep period, thereby acquiring a frequency spectrum. As the Fourier transform, for example, fast Fourier transform (hereinafter, referred to as "FFT") is performed. Then, it is determined whether or not an α wave component is contained in the FFT result (e.g., spectrum obtained by FFT) on each period (epoch). For example, the appearance status acquiring unit 1021 may determine whether or not an α wave component at a level of a predetermined threshold value or more is contained in the FFT result obtained on each period, and, if the α wave component at a level of the threshold value or more is contained, determine that the α wave component is contained in that period. Then, the number of periods (epochs) determined to contain the α wave component, or the ratio of this number with respect to the predetermined number of multiple periods may be taken as the information indicating the appearance rate. Note that, instead of Fourier transform, a spectrum analyzer or the like may be used to detect the presence or absence of α waves in each period.

(3) The Case in which a Power of α Waves in a Non-REM Sleep Period is Acquired

As described above, in the case of a patient with depression, α spindle waves often appear in a non-REM sleep period, and, thus, a power of the α waves in the non-REM sleep period is high. Thus, the appearance status acquiring unit 1021 acquires information indicating a power of α waves in the sleep electroencephalogram information in a non-REM sleep period, in the sleep electroencephalogram information. The power of α waves is, for example, an energy of the α waves per unit time, a waveform size (e.g., voltage) of the α waves, or the like. Note that the same is applied to the electroencephalogram information in other frequency bands. Here, as an example, the appearance status acquiring unit 1021 performs, as in (2) above, Fourier transform such as FFT to detect an α wave component in each of one or more periods forming a non-REM sleep period in the sleep electroencephalogram information, and acquires a level (value) such as peak of the detected α wave component, as information indicating a power of α waves in each period. Alternatively, the sum of the powers in α wave band or the integral values of the powers indicated by the FFT result may be acquired as the information indicating a power of α waves. Accordingly, for example, information indicating a time-series change in the power of α waves in each period can be acquired. Note that, instead of Fourier transform, a spectrum analyzer or the like may be used to detect the power of α waves in each period.

The appearance status acquiring unit 1021 may perform only one process or may perform multiple processes of the above-described processes (1) to (3).

The appearance status acquiring unit 1021 may be realized typically as an MPU, a memory, or the like. Typically, the processing procedure of the appearance status acquiring unit 1021 is realized by software, and the software is stored in a storage medium such as a ROM. Note that the processing procedure may be realized also by hardware (a dedicated circuit).

The determining unit 1022 determines the presence or absence of a mental disorder according to the information indicating an appearance status of α waves acquired by the appearance status acquiring unit 1021. For example, the determining unit 1022 determines the presence or absence of a mental disorder according to the information indicating an appearance rate or a power of α waves acquired by the appearance status acquiring unit 1021.

For example, if the appearance status acquiring unit 1021 acquires information indicating an appearance rate of spindle waves of α waves in a non-REM sleep period as in (1) above, the determining unit 1022 reads a threshold value for the appearance rate of α spindle waves prepared in advance, and determines whether or not the value indicating the appearance rate of α spindle waves acquired by the appearance status acquiring unit 1021 exceeds the threshold value. If the value exceeds the threshold value, the determining unit 1022 determines that the test subject associated with the sleep electroencephalogram information has depression. For example, the threshold value in this case is preferably 2 or more. Furthermore, if the appearance rate of epochs containing α spindle waves at the threshold value or more in multiple epochs in a non-REM sleep period is a threshold value or more, it may be determined that depression is present. For example, in this case, if the appearance rate of epochs containing two or more α spindle waves is 80% or more, preferably 90% or more, with respect to the entire epochs targeted for the detection, it is determined that the possibility of having depression is high. Determining that depression is present is a concept that also includes determining that the possibility of having depression is high. The same is applied to the description below.

Furthermore, for example, if the appearance status acquiring unit 1021 acquires information indicating an appearance rate of α waves in a non-REM sleep period as in (2) above, the determining unit 1022 reads a threshold value for the appearance rate of α waves prepared in advance, and determines whether or not the value indicating the appearance rate of periods in which α waves are detected exceeds the threshold value, the appearance rate being acquired by the appearance status acquiring unit 1021. If the value exceeds the threshold value, the determining unit 1022 determines that the test subject associated with the sleep electroencephalogram information has depression. The study by the inventors has revealed that the threshold value for the appearance rate of α waves may be set at, for example, 12%, preferably 15%. For example, if a ratio of the time in which α waves are detected in the whole or part of a non-REM sleep period is 12% or more, the determining unit 1022 determines that depression is present.

Furthermore, for example, if the appearance status acquiring unit 1021 acquires information indicating a power of an α wave component in a non-REM sleep period as in (3) above, the determining unit 1022 reads a threshold value for the power of α waves prepared in advance, and determines whether or not any α wave component acquired in each period by the appearance status acquiring unit 1021 has a power exceeding the threshold value. If any α wave component exceeds the threshold value, the determining unit 1022 determines that the test subject associated with the sleep electroencephalogram information has depression. The threshold value for the power of α waves is, for example, 1 to 1.5 $\mu V^2$. In order to detect serious depression, the threshold value may be set at 2 $\mu V^2$. Alternatively, in consideration of factors such as noise or measurement errors, it may be determined that any α wave component acquired in each period has a power exceeding the threshold value, if the number of periods exhibiting a power exceeding the threshold value is a predetermined number or more. Furthermore, the determining unit 1022 may calculate an average value of the powers of α waves in the respective periods, and determine whether or not this average value exceeds the predetermined threshold value, thereby determining whether or not any α wave component acquired in each period by the appearance status acquiring unit 1021 has a power exceeding the threshold value. It will be appreciated that, if the average value exceeds the threshold value, a value exceeding the threshold value is included, and, thus, such determination eventually provides a similar determination result.

Note that, if the appearance status acquiring unit 1021 performs multiple processes of the above-described processes (1) to (3), the determining unit 1022 may individually perform the above-described determination on each of the processing results, and acquire the respective determination results. Furthermore, a comprehensive determination result may be acquired by further using these determination results. For example, only if all the determination results on the respective multiple processes indicate that depression is present, a determination result that depression is present may be acquired. Furthermore, if the determination results on the respective multiple processes include both a determination result that depression is present and a determination result that depression is not present, a determination result that there is a possibility of depression or the like may be acquired.

The determining unit 1022 may be realized typically as an MPU, a memory, or the like. Typically, the processing procedure of the determining unit 1022 is realized by software, and the software is stored in a storage medium such as a ROM. Note that the processing procedure may be realized also by hardware (a dedicated circuit).

The specific electroencephalogram acquiring unit 1023 acquires electroencephalogram information at one or more predetermined specific frequencies from the sleep electroencephalogram information. Here, a specific frequency may be considered as a specific frequency band. In this example, as an example, α waves are acquired from the sleep electroencephalogram information. The electroencephalogram information at one or more predetermined specific frequencies may be a portion in which the above-described α spindle waves are detected. Acquiring the electroencephalogram information at a specific frequency may be extracting information on a waveform indicating only the specific frequency component using a filter such as a bandpass filter, may be acquiring electroencephalogram information containing the specific frequency, or may be acquiring information that eventually makes it possible to acquire electroencephalogram information containing the specific frequency, such as information indicating a period containing the specific frequency. For example, it may be acquiring information on a waveform containing the specific frequency component, or a time indicating a period in which this waveform is present (the start time or the end time), from the sleep electroencephalogram information. For example, in the sleep electroencephalogram information, a waveform in a period corresponding to a period in which α waves spindle waves are detected may be acquired as the electroencephalogram information at a specific frequency. The specific electroencephalogram acquiring unit 1023 acquires, for example, the electroencephalogram information at a specific frequency from the sleep electroencephalogram information in a non-REM sleep period. For example, the electroencephalogram information at a specific frequency is acquired in a period in which the appearance status acquiring unit 1021 is to acquire the information indicating an appearance status of α waves, in a non-REM sleep period. Here, the electroencephalogram information at a specific frequency that is to be acquired may be only a portion in which the output of the amplitude or the like is a predetermined threshold value or more. For example, the electroencephalogram information that is to be acquired by the specific electroencephalogram acquiring unit 1023 may be electroencephalogram information in non-successive multiple periods having the electroencephalogram information at a specific frequency. Furthermore, the analyzing portion 102 may acquire the electroencephalogram information at two or more predetermined specific frequencies. For example, the electroencephalogram information of α waves, β waves, or the like may be acquired.

Furthermore, the specific electroencephalogram acquiring unit 1023 may acquire information indicating an appearance status of electroencephalogram information at a predetermined specific frequency, from the sleep electroencephalogram information. This processing is similar to the processing performed by the appearance status acquiring unit 1021. Thus, portions of the appearance status acquiring unit 1021 and the specific electroencephalogram acquiring unit 1023 that perform this processing may be provided as one unit. Alternatively, the specific electroencephalogram acquiring unit 1023 may acquire as appropriate information indicating the appearance status acquired by the appearance status acquiring unit 1021. Here, as an example, the electroencephalogram information at a specific frequency refers to α waves.

The specific electroencephalogram acquiring unit 1023 may be realized typically as an MPU, a memory, or the like. Typically, the processing procedure of the specific electroencephalogram acquiring unit 1023 is realized by software, and the software is stored in a storage medium such as a ROM. Note that the processing procedure may be realized also by hardware (a dedicated circuit).

The medication determining portion 103 acquires information indicating an appearance status of γ waves contained in the sleep electroencephalogram information stored in the storage portion 101, and determines whether or not drug administration has been performed for a mental disorder according to this information. The γ waves detected in the sleep electroencephalogram information correspond to a waveform of noise generated by the body greatly swinging during body motion, and it seems that, during sleep, the γ waves correspond to a waveform generated when test subject is performing a so-called roll-over. That is to say, detecting γ waves is detecting a point in time at which the test subject rolls over. As a part of medical treatment for patients with depression, there is a case in which tranquilizers, anti-depressants, or the like are administered to induce sleep with the effects of these drugs. It is often the case that patients administered with such drags do not roll over particularly in the first half of sleep. That is to say, if patients are on medication, generation of γ waves tends to be lowered.

Figure 7:
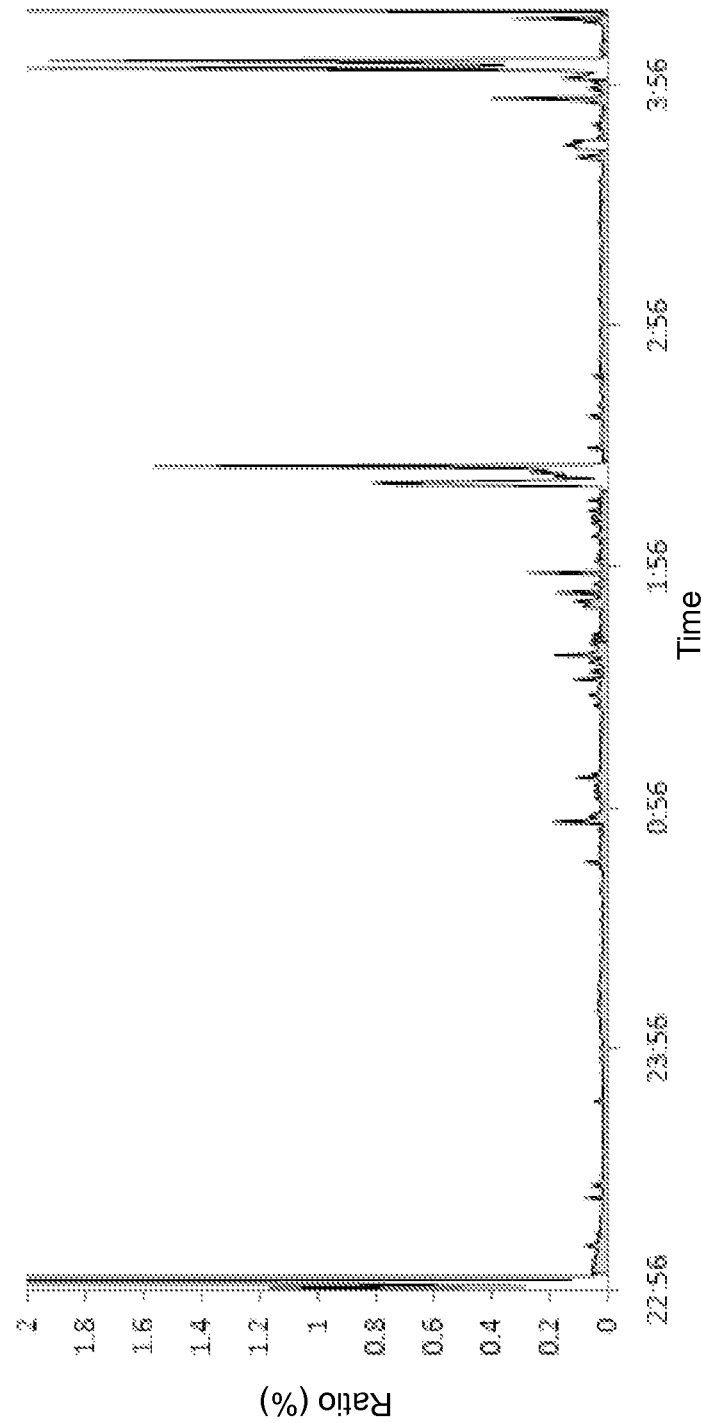
FIG. 7 is a graph showing the appearance rate of $\gamma$ waves, illustrating the mental disorder analysis apparatus according to this example.

FIG. 7 is an exemplary graph in which generation ratios of γ waves in respective epochs in sleep period of a patient with depression, obtained by performing FFT on the epochs, are arranged in a time series.

Figure 8:
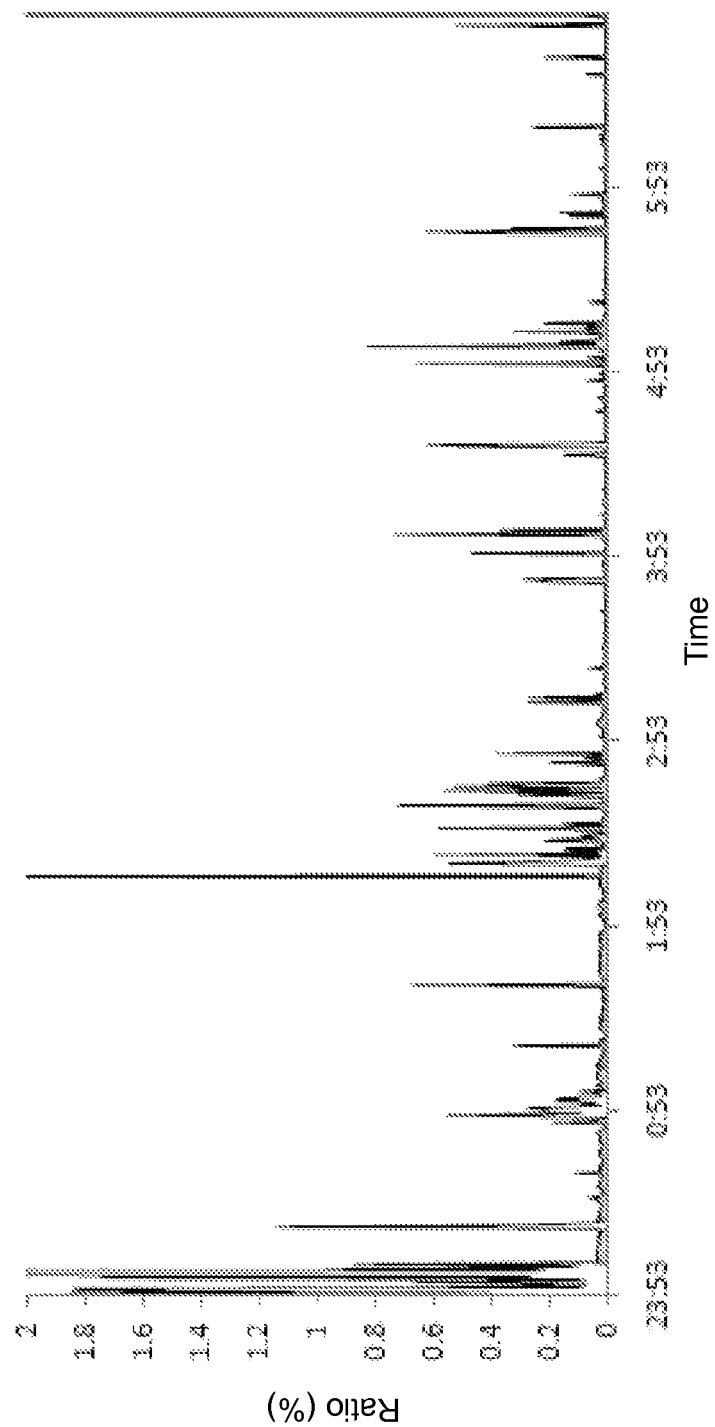
FIG. 8 is a graph showing the appearance rate of $\gamma$ waves, illustrating the mental disorder analysis apparatus according to this example.

Furthermore, FIG. 8 is an exemplary graph in which generation ratios of γ waves in respective epochs in sleep period of a healthy person, obtained by performing FFT on the epochs, are arranged in a time series.

As clearly seen from FIGS. 7 and 8, a patient with depression has lower appearance rates of γ waves than those of a healthy person in the first half of sleep period.

Using this aspect, the medication determining portion 103 determines whether or not drug administration has been performed for a mental disorder, by determining how often the test subject rolls over, using the information indicating an appearance status of γ waves contained in the sleep electroencephalogram information. Here, as an example, a case will be described in which the medication determining portion 103 uses the γ appearance status acquiring unit 1031 and the administration determining unit 1032 to perform determination regarding medication.

The medication determining portion 103 may be realized typically as an MPU, a memory, or the like. Typically, the processing procedure of the medication determining portion 103 is realized by software, and the software is stored in a storage medium such as a ROM. Note that the processing procedure may be realized also by hardware (a dedicated circuit).

The γ appearance status acquiring unit 1031 acquires information indicating an appearance status of γ waves contained in the sleep electroencephalogram information stored in the storage portion 101. In consideration of the influence of medication, for example, the γ appearance status acquiring unit 1031 preferably acquires information indicating an appearance status of γ waves in part or the whole of the sleep electroencephalogram information in the first half of sleep period. The information indicating an appearance status is, for example, information indicating an appearance rate. For example, as in the processing in which the appearance status acquiring unit 1021 acquires information indicating an appearance rate of α waves as in (2) above, the γ appearance status acquiring unit 1031 performs Fourier transform to detect a γ wave component in each of multiple periods in the sleep electroencephalogram information, and acquires information indicating an appearance rate of periods in which a γ wave component is detected, as information indicating an appearance rate of γ waves. The period in which a γ wave component is detected may be considered as a period in which γ waves at a predetermined threshold value or more are detected. Furthermore, as in (3) above, the power of the γ waves in one or more periods in the sleep electroencephalogram information may be acquired as information indicating an appearance status of γ waves.

The γ appearance status acquiring unit 1031 may be realized typically as an MPU, a memory, or the like. Typically, the processing procedure of the γ appearance status acquiring unit 1031 is realized by software, and the software is stored in a storage medium such as a ROM. Note that the processing procedure may be realized also by hardware (a dedicated circuit).

The administration determining unit 1032 determines whether or not drug administration has been performed for a mental disorder, according to the information indicating an appearance status of γ waves acquired by the γ appearance status acquiring unit 1031. For example, the administration determining unit 1032 reads a predetermined threshold value, and determines whether or not the value of the information indicating an appearance status of γ waves acquired by the γ appearance status acquiring unit 1031 exceeds the threshold value. If the value does not exceed the threshold value, the administration determining unit 1032 determines that drug administration has been performed for a mental disorder. For example, if the number of times of appearance of γ waves in sleep period for 7 to 8 hours is less than 30, the administration determining unit 1032 determines that drug administration has been performed. Furthermore, since generation of γ waves in the first half of sleep period is low if drug administration has been performed, the administration determining unit 1032 may determine that drug administration has been performed if the number of times of appearance of γ waves in about 3 hours in the first half of sleep period is less than 10. In order to perform more reliable determination, it may be determined that drug administration has been performed if the number of times of appearance of γ waves is less than 5.

The administration determining unit 1032 may be realized typically as an MPU, a memory, or the like. Typically, the processing procedure of the administration determining unit 1032 is realized by software, and the software is stored in a storage medium such as a ROM. Note that the processing procedure may be realized also by hardware (a dedicated circuit).

The output portion 104 outputs a result of the analysis performed by the analyzing portion 102. For example, the output portion 104 outputs a result of the determination regarding the presence or absence of a mental disorder performed by the analyzing portion 102 (here, in particular, the determining unit 1022). The result of the determination regarding the presence or absence of a mental disorder may be information including the name of the mental disorder. Furthermore, the output portion 104 may output a result of the determination performed by the medication determining portion 103 (here, in particular, the administration determining unit 1032). For example, a result of the determination indicating the presence or absence of medication may be output.

Furthermore, the output portion 104 may output, for example, the sleep electroencephalogram information at the specific frequency acquired by the analyzing portion 102 (here, in particular, the specific electroencephalogram acquiring unit 1023). The output indicating the sleep electroencephalogram information at a specific frequency may be output of a waveform at the specific frequency acquired by the analyzing portion 102 using filtering or the like, such as a waveform of α waves as it is, or may be output indicating the portion or period containing the specific frequency acquired by the analyzing portion 102 in the sleep electroencephalogram information. Such output makes it easy to find an abnormal portion.

The output portion 104 may output, for example, the sleep electroencephalogram information at the specific frequency acquired by the analyzing portion 102 (here, in particular, the specific electroencephalogram acquiring unit 1023) and the sleep electroencephalogram information from which said sleep electroencephalogram information has been acquired. For example, this output may be output of a waveform at a specific frequency acquired using filtering or the like, such as a waveform of α waves, and a waveform of sleep electroencephalogram information from which said waveform has been acquired, or may be output of a portion in which a waveform at a specific frequency has been acquired in the sleep electroencephalogram information, in a display mode different from that of the other portions (e.g., highlighted output).

Furthermore, the output portion 104 outputs, for example, the sleep electroencephalogram information at the two or more specific frequencies acquired by the analyzing portion 102 (here, in particular, the specific electroencephalogram acquiring unit 1023). For example, this output may be output of waveforms at two or more specific frequencies acquired using filtering or the like, such as a waveform of α waves and a waveform of β waves, or may be output of only a portion in which waveforms at two or more specific frequencies are contained in the sleep electroencephalogram information.

Furthermore, the output portion 104 may output, for example, the information indicating the appearance status acquired by the analyzing portion 102 (here, in particular, the specific electroencephalogram acquiring unit 1023). For example, information in which powers at a specific frequency respectively acquired in successive multiple periods (e.g., epochs) contained in the sleep electroencephalogram information are shown in a time series in the form of a graph may be output as information indicating an appearance status.

Output described here is a concept that includes display on a display screen, projection using a projector, printing in a printer, transmission to an external apparatus, accumulation in a storage medium, delivery of a processing result to another processing apparatus or another program, and the like. The output portion 104 may be considered to include or not to include an output device, such as a display screen or a loudspeaker. The output portion 104 may be realized as driver software for an output device, or a combination of driver software for an output device, the output device, and the like.

The electroencephalogram acquiring apparatus 5 measures the electroencephalograms during sleep of a test subject. The sleep electroencephalogram information acquired by the measurement is transmitted to the mental disorder analysis apparatus 1 via a network or a signal wire or accumulated in a storage medium (not shown) or the like. The electroencephalogram acquiring apparatus 5 is, for example, an electroencephalograph.

Figure 9:
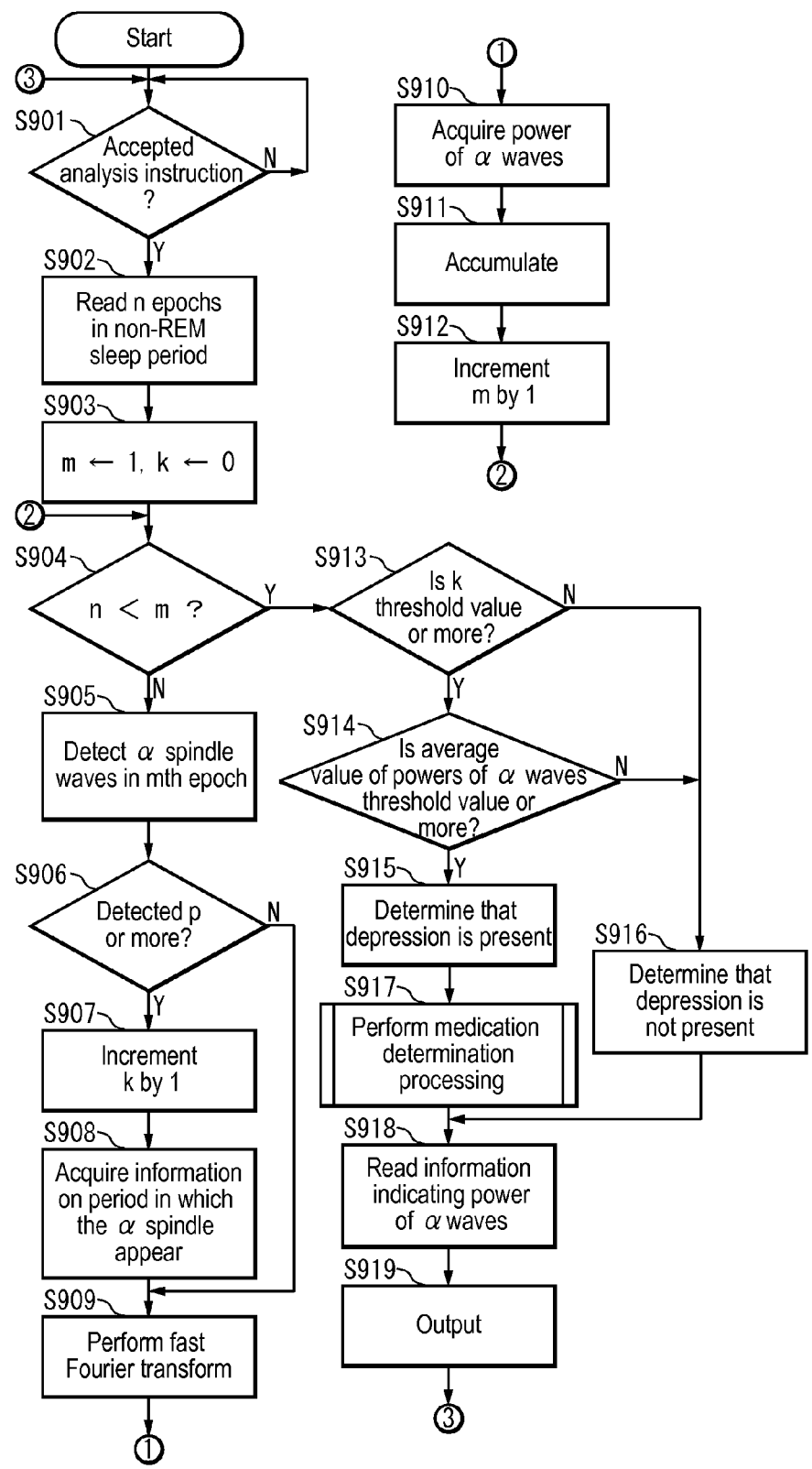
FIG. 9 is a flowchart showing an operation of the mental disorder analysis apparatus according to this example.

FIG. 9 is a flowchart showing an operation of the mental disorder analysis apparatus in this example. Hereinafter, this operation will be described. Here, it is assumed that sleep electroencephalogram information is information composed of multiple epochs.

(Step S901) It is determined whether or not the mental disorder analysis apparatus 1 has accepted an instruction for performing analysis of the sleep electroencephalogram information. This instruction is accepted, for example, via an accepting portion (not shown) or the like. The instruction for performing analysis may have information for identifying a test subject, or information for identifying sleep electroencephalogram information targeted for the analysis. For example, in the storage portion 101, the sleep electroencephalogram information of a test subject is accumulated in association with the information for identifying the test subject and the information for identifying the sleep electroencephalogram information. If the instruction for performing analysis has been accepted, the procedure advances to step S902, and, if not, the procedure returns to step S901.

(Step S902) The appearance status acquiring unit 1021 reads electroencephalogram information for n epochs (n is an integer of 2 or more) in a non-REM sleep period, from the sleep electroencephalogram information stored in the storage portion 101. For example, successive n epochs are read after the elapse of a predetermined period of time after the start time of a non-REM sleep period. The appearance status acquiring unit 1021 reads epochs, for example, from the sleep electroencephalogram information associated with the identifying information of a test subject specified by the instruction for performing analysis, or the sleep electroencephalogram information corresponding to the identifying information specified by the instruction for performing analysis. The read electroencephalogram information is temporarily stored in a memory (not shown) or the like.

(Step S903) The appearance status acquiring unit 1021 substitutes 1 for a counter m, and substitutes 0 for a counter k.

(Step S904) The appearance status acquiring unit 1021 determines whether or not the value of the counter m is larger than n. If the value is not larger than n, the procedure advances to step S905, and, otherwise, the procedure advances to step S913.

(Step S905) The appearance status acquiring unit 1021 detects α spindle waves in an mth epoch.

(Step S906) The appearance status acquiring unit 1021 determines whether or not p or more α spindle waves (p is an integer of 1 or more) are detected in the mth epoch. As the value of p, for example, "2" or the like is used. Note that the value of p is preferably optimized according to experimental results or the like. If p or more α spindle waves are detected, the procedure advances to step S907, and, if not, the procedure advances to step S909.

(Step S907) The appearance status acquiring unit 102 increments the counter k by 1. The counter k is a counter for counting the number of epochs in which the α spindle waves are detected.

(Step S908) The specific electroencephalogram acquiring unit 1023 acquires information indicating a period in which one or more α spindle waves detected in step S905 appear. Information indicating the period is, for example, the start time and the end time of the period. The acquired information is accumulated in the storage medium (not shown) or the like.

(Step S909) The appearance status acquiring unit 1021 performs fast Fourier transform on the mth epoch.

(Step S910) The appearance status acquiring unit 1021 acquires the power of α waves from the result of the fast Fourier transform. For example, a peak level in α wave band is acquired as the power.

(Step S911) The appearance status acquiring unit 1021 accumulates the acquired power of α waves in association with the mth epoch in the storage medium (not shown) or the like. The appearance status acquiring unit 1021 accumulates the acquired power of α waves in association with, for example, the start time of the mth epoch, the identifying information or the reading order of the mth epoch, or the like.

(Step S912) The appearance status acquiring unit 1021 increments the counter m by 1. Then, the procedure returns to step S904.

(Step S913) The determining unit 1022 determines whether or not the value of the counter k is a threshold value or more. As the threshold value, for example, a value of 80 to 90% of the value of n is used. For example, the determining unit 1022 determines whether or not the value of the counter k is 0.8×n or more. If the value is the threshold value or more, the procedure advances to step S914, and, if not, the procedure advances to step S916. Note that, instead of whether or not the value of k is the threshold value or more, whether or not k/n is a threshold value or more may be determined. As the threshold value in this case, for example, a value of 0.8 to 0.9 is used.

(Step S914) The determining unit 1022 calculates an average value of the powers of α waves in the respective epochs acquired in step S910, and determines whether or not the average value is a predetermined threshold value or more. This determination is determination regarding whether or not depression is present based on the power of α waves. If the value is the threshold value or more, the procedure advances to step S915, and, if not, the procedure advances to step S916.

(Step S915) The determining unit 1022 determines that the test subject targeted for the analysis has depression. Then, the procedure advances to step S917.

(Step S916) The determining unit 1022 determines that the test subject targeted for the analysis does not have depression. Then, the procedure advances to step S918.

(Step S917) The medication determining portion 103 determines whether or not, when the electroencephalogram information was acquired, drug administration had been performed on the test subject associated with the sleep electroencephalogram information targeted for the analysis, thereby acquiring a determination result. Note that this processing will be described later in detail.

(Step S918) The specific electroencephalogram acquiring unit 1023 reads information indicating the power of α waves accumulated by the appearance status acquiring unit 1021 in association with each epoch in step S911.

(Step S919) The output portion 104 outputs information indicating the determination result acquired by the determining unit 1022 in step S915 or S916. Furthermore, the output portion 104 outputs a graph in which powers are shown as heights in a time series, the graph being generated using the information indicating the power of α waves in each epoch acquired in step S918. Furthermore, the output portion 104 reads the sleep electroencephalogram information targeted for the analysis from the storage portion 101, uses this information to generate sleep electroencephalogram information in which the period acquired in step S908 is displayed in a mode different from that of the other periods, and outputs the information. Furthermore, the determination result in step S917 regarding drug administration is output. Then, the procedure returns to step S901.

Here, the process is terminated by powering off or an interruption to abort the process in the flowchart in FIG. 9.

Figure 10:
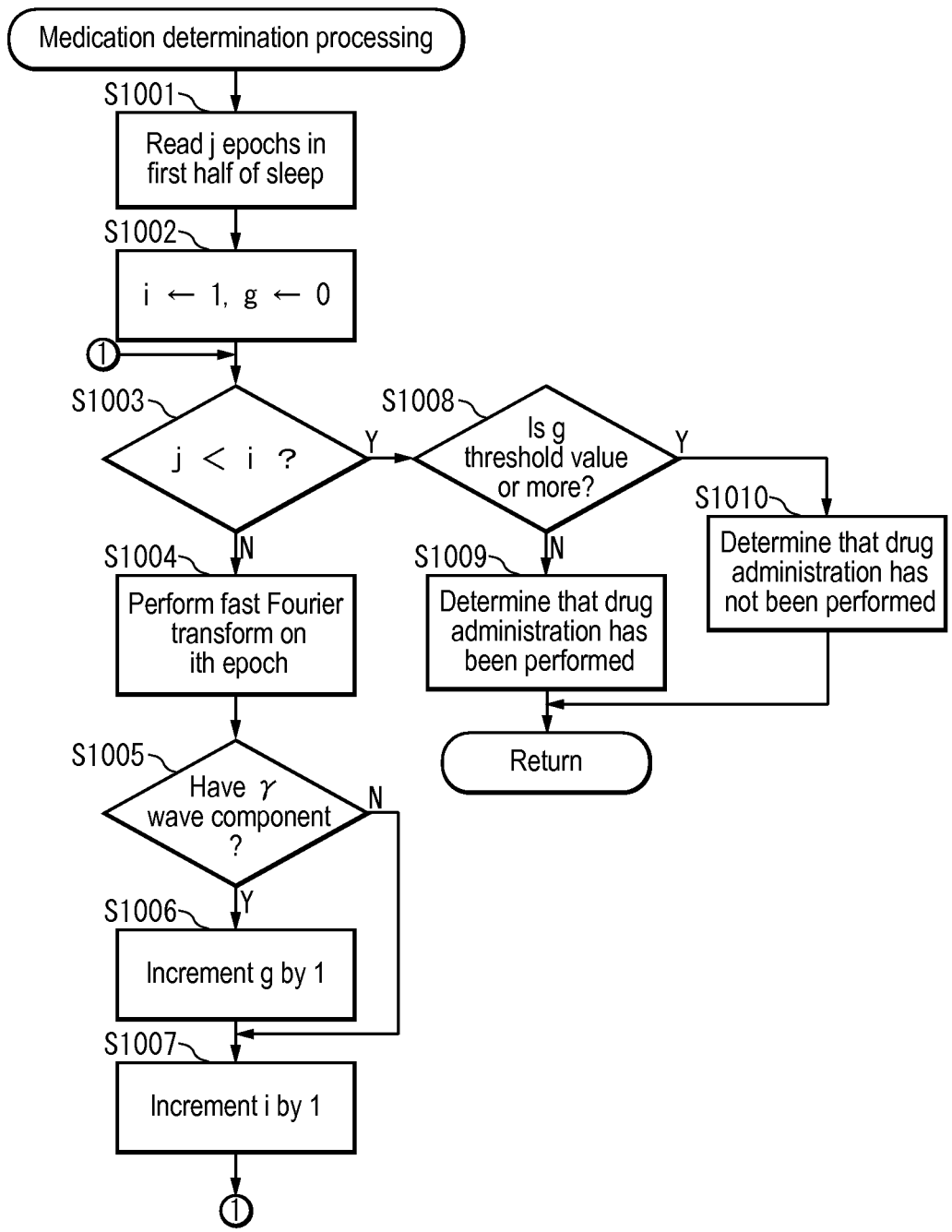
FIG. 10 is a flowchart showing an operation in medication determination processing performed by the mental disorder analysis apparatus according to this example.

FIG. 10 is a flowchart showing an operation in medication determination processing performed by the mental disorder analysis apparatus in this example, and corresponds to the process in step S917 in FIG. 9. Hereinafter, this operation will be described.

(Step S1001) The medication determining portion 103 reads electroencephalogram information for j epochs (j is an integer of 2 or more) in the first half of sleep period, from the same sleep electroencephalogram information as the sleep electroencephalogram information read in step S902. For example, successive j epochs are read after the elapse of a predetermined period of time after the onset of sleep. The read electroencephalogram information is temporarily stored in a memory (not shown) or the like.

(Step S1002) The γ appearance status acquiring unit 1031 substitutes 1 for a counter i, and substitutes 0 for a counter g.

(Step S1003) The γ appearance status acquiring unit 1031 determines whether or not the value of the counter i is larger than j. If the value is not larger than j, the procedure advances to step S1004, and, otherwise, the procedure advances to step S1008.

(Step S1004) The γ appearance status acquiring unit 1031 performs fast Fourier transform on an ith epoch.

(Step S1005) The γ appearance status acquiring unit 1031 determines whether or not there is a γ wave component, from the result of the fast Fourier transform. If there is, the procedure advances to step S1006, and, if not, the procedure advances to step S1007.

(Step S1006) The γ appearance status acquiring unit 1031 increments the counter g by 1.

(Step S1007) The γ appearance status acquiring unit 1031 increments the counter i by 1. Then, the procedure returns to step S1003.

(Step S1008) The administration determining unit 1032 determines whether or not the value of the counter g is a threshold value or more. If the value is the threshold value or more, the procedure advances to step S1010, and, if not, the procedure advances to step S1009.

(Step S1009) The administration determining unit 1032 determines that drug administration has been performed. Then, the determination result is returned to the upper-level processing.

(Step S1010) The administration determining unit 1032 determines that drug administration has not been performed. Then, the determination result is returned to the upper-level processing.

Hereinafter, a specific operation of the mental disorder analysis apparatus 1 in this example will be described. Here, as an example, a case will be described in which the mental disorder analysis apparatus 1 is an apparatus that diagnoses depression. Here, it is assumed that, in the storage portion 101, the sleep electroencephalogram information of multiple test subjects acquired by the electroencephalogram acquiring apparatus 5 is stored.

FIG. 11 is an electroencephalogram information management table that manages the sleep electroencephalogram information stored in the storage portion 101. The electroencephalogram information management table has items "test subject name" and "sleep electroencephalogram information". In the table, "sleep electroencephalogram information" refers to the file name of the sleep electroencephalogram information. It is assumed that, here, the sleep electroencephalogram information is composed of multiple pieces of electroencephalogram information in the unit of epoch. Note that the length of each epoch is 30 seconds in this example.

For example, it is assumed that the user gives an instruction for analyzing the sleep electroencephalogram information of a test subject with the test subject name "Kimura A" via an accepting portion (not shown) or the like to the mental disorder analysis apparatus 1.

The appearance status acquiring unit 1021 reads n epochs (n is an integer of 1 or more) in a non-REM sleep period in the sleep electroencephalogram information managed as a record in which "test subject name" is "Kimura A" in the electroencephalogram information management table shown in FIG. 11. Here, as an example, it is assumed that the value of n is "20". Furthermore, here, for example, it is assumed that epochs are read after the elapse of a predetermined number of epochs after the start of a non-REM sleep period. Then, the read sleep electroencephalogram information in the unit of epoch is temporarily stored in association with the start time of each epoch in a storage medium such as a memory (not shown).

Next, the appearance status acquiring unit 1021 detects α spindle waves in a first epoch with the earliest start time, in the read sleep electroencephalogram information in the unit of epoch. The α spindle waves are detected according to processing or the like with use of known arts for acquiring sleep spindle waves as described above.

Here, for example, it is assumed that the appearance status acquiring unit 1021 has detected two α spindle waves from the first epoch. Then, the appearance status acquiring unit 1021 determines whether or not the detected number is p or more (p is an integer of 1 or more), which is a predetermined number. Note that p may be considered as a threshold value. For example, if p is "1", the appearance status acquiring unit 1021 determines that the number of detected α spindle waves "2" is the predetermined number p or more. Thus, the appearance status acquiring unit 1021 increments, by 1, the counter k, which is for counting the number of epochs in which the α spindle waves are detected. If the counted number is less than the predetermined number p, the counter k is not incremented. It is assumed that, in this example, this threshold value is stored in advance in a storage medium (not shown) or the like. The same is applied to the other threshold values.

Furthermore, the specific electroencephalogram acquiring unit 1023 acquires the start time and the end time of each of the two detected α spindle waves from the sleep electroencephalogram information, and accumulates the information in the storage medium (not shown) or the like.

Next, the appearance status acquiring unit 1021 performs fast Fourier transform (FFT) on the first epoch. Then, α wave peak values in the transform result are acquired. In this example, the first epoch is divided into eight portions each in 4 seconds, and eight values are obtained by performing fast Fourier transform on each of these portions. The average value of these values is used as the value obtained by performing fast Fourier transform on the first epoch. The same is applied to a second and subsequent epochs. In this example, since one epoch has 30 seconds, if one epoch is divided into portions each in 4 seconds, a portion in only 2 seconds appears. This portion in 2 seconds is subjected as it is to fast Fourier transform, and the obtained value is multiplied by two and used as the value obtained by performing fast Fourier transform on that portion. For example, it is assumed that the acquired peak value is "1.5 $\mu V^2$". Then, the peak value is accumulated in association with the start time of the first epoch in a storage medium (not shown) or the like. Note that, instead of the peak values, integral values of the powers of α waves obtained by FFT may be acquired. Furthermore, the information may be accumulated, in association with identifying information of an epoch such as the number indicating the order of the epoch, instead of association with the start time of the epoch.

In a similar manner, the appearance status acquiring unit 1021 and the specific electroencephalogram acquiring unit 1023 repeat similar processing on the second to the nth epochs. It is assumed that, as a result obtained by repeating the processing, the value of the counter k becomes "20".

FIG. 12 is an α spindle wave management table that manages the start time and the end time of the α spindle waves acquired by the specific electroencephalogram acquiring unit 1023 as a result obtained by repeating the processing.

FIG. 13 is an α power management table that manages the power of α waves in each epoch obtained by the appearance status acquiring unit 1021 as a result obtained by repeating the processing, and the start time of each epoch.

Next, the determining unit 1022 determines whether or not the value of the counter k, indicating the number of times of appearance of epochs in which the α spindle waves are detected, is at least a predetermined threshold value for the number of epochs in which the α spindle waves are detected. Here, if the threshold value is "10", it is determined that the value of the counter k "20" exceeds the threshold value.

Furthermore, the determining unit 1022 calculates an average value of values of "α power" in the α power management table shown in FIG. 13. It is assumed that the calculated average value is "1.45 $\mu V^2$". Then, it is determined whether or not the average value is at least a predetermined threshold value for the power of α waves. For example, if the threshold value is "1.0 $\mu V^2$", it is determined that the average value is the threshold value or more.

The determining unit 1022 acquires a determination result that the test subject is a patient with depression, because the number of times of appearance of epochs in which the α spindle waves are detected is the threshold value or more, and because the average value of the powers of α waves is the threshold value or more. If the value is less than the threshold value even in one of these conditions, a determination result that the test subject is not a patient with depression is acquired.

Since it is determined that the test subject is a patient with depression, the γ appearance status acquiring unit 1031 reads j epochs (j is an integer of 1 or more) from the first half of sleep period in the sleep electroencephalogram information managed as the record in which "test subject name" is "Kimura A" in the electroencephalogram information management table shown in FIG. 11. Here, as an example, it is assumed that the value of j is "20". Furthermore, for example, it is assumed that epochs are read after the elapse of a predetermined number of epochs after the start of sleep period. Then, the read sleep electroencephalogram information in the unit of epoch is temporarily stored in association with the start time of each epoch in a storage medium such as a memory (not shown).

Next, the γ appearance status acquiring unit 1031 performs fast Fourier transform on the first epoch with the earliest start time, in the read sleep electroencephalogram information in the unit of epoch. Then, it is determined whether or not γ waves are detected in the FFT result. Here, it is determined whether or not γ waves at a level (power) of a threshold value or more are detected. If such γ waves are detected, the counter g is incremented by 1. If not, the counter g is not incremented.

The γ appearance status acquiring unit 1031 performs similar processing on all of the read epochs. Then, the administration determining unit 1032 determines whether or not the obtained value of the counter g is a predetermined threshold value or more. If the obtained value of the counter g is "1", and the threshold value is "3", the value of the counter g is less than the threshold value, and, thus, the administration determining unit 1032 determines that drug administration has been performed, and acquires information indicating the determination result. If the obtained value is the threshold value or more, it is determined that drug administration has not been performed, and information indicating the determination result is acquired.

The output portion 104 displays, on a monitor (not shown) or the like, information indicating the determination result "test subject is a patient with depression" acquired by the determining unit 1022. Furthermore, the output portion 104 generates a graph in which powers of α waves are shown as heights in a time series, using the α power management table shown in FIG. 13, and displays this graph on a monitor (not shown) or the like. Furthermore, the output portion 104 reads information on periods around the multiple epochs targeted for the analysis, in the sleep electroencephalogram information associated with "Kimura A" targeted for the analysis, from the storage portion 101. Then, the electroencephalogram information in a period in which α spindle waves are acquired is acquired from the sleep electroencephalogram information, the period being indicated with the start time and the end time in each record in the α spindle wave management table shown in FIG. 12, and a waveform graph of the sleep electroencephalogram information is generated in which the acquired portion of the electroencephalogram information is displayed in a mode different from that of the other portions, and displayed on a monitor (not shown) or the like. For example, a waveform graph is generated in which the color of the background and the color of the line plotting the waveform in that region are inverted with respect to those in the other regions. Furthermore, the determination result regarding drug administration indicating that drug administration has been performed, which is acquired by the administration determining unit 1032, is output.

Figure 14:
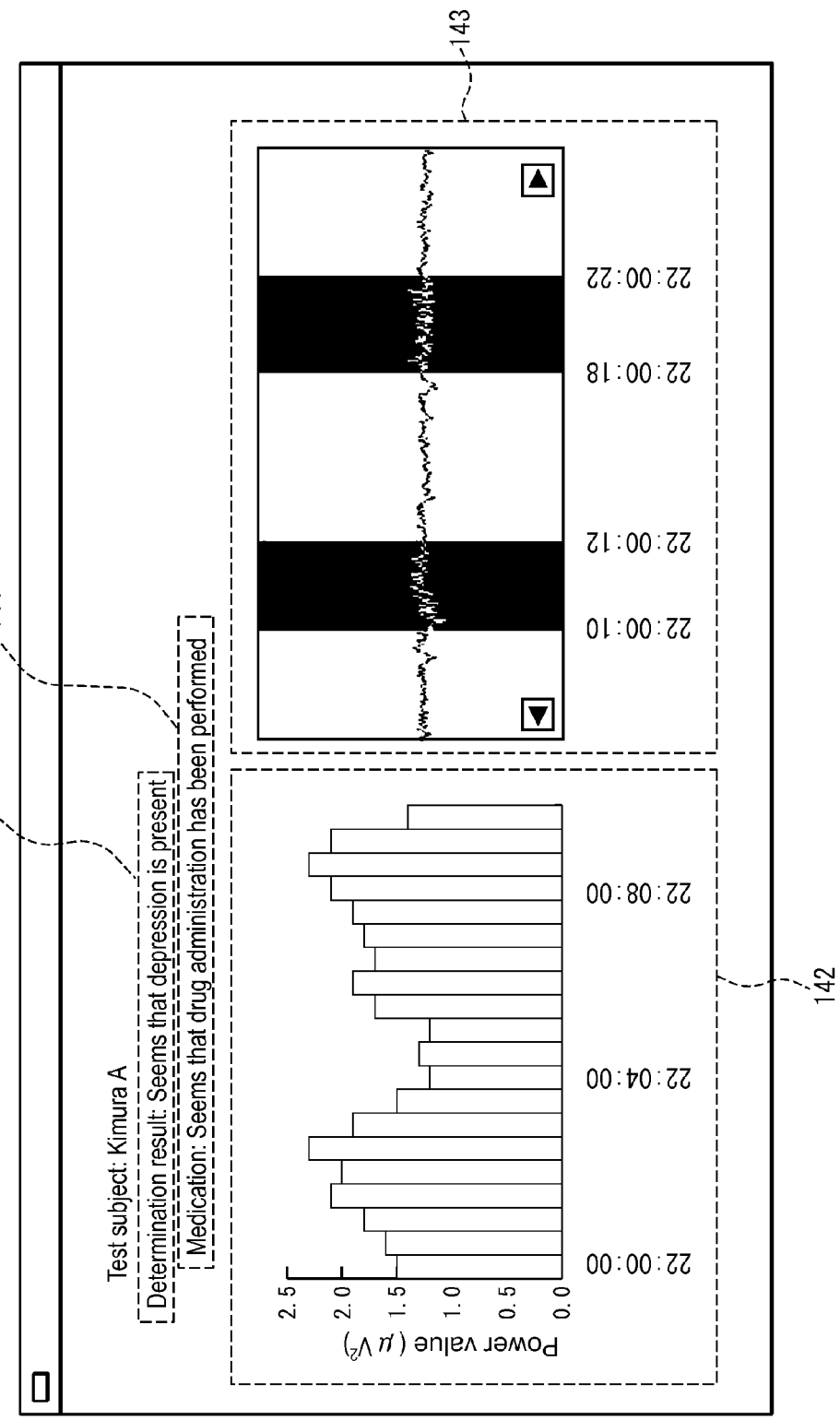
FIG. 14 is a diagram showing a display example of a result of an analysis performed by the mental disorder analysis apparatus according to this example.

FIG. 14 is a diagram showing an example in which a result obtained by analyzing the sleep electroencephalogram information is displayed by the output portion 104. In the diagram, a region 141 displays the determination result acquired by the determining unit 1022. Furthermore, a region 142 shows a graph of the α power. Furthermore, a region 143 displays α spindle waves together with the sleep electroencephalogram information based on which the analysis has been performed. Furthermore, a region 144 displays the determination result regarding drug administration acquired by the administration determining unit 1032.

As described above, according to this example, since the electroencephalogram information during sleep is used to determine the presence or absence of a mental disorder, the influence on the electroencephalograms due to actions and the like from the outside on the test subject is reduced to the extent possible, and, thus, a mental disorder can be accurately diagnosed. In particular, with the appearance status of α waves in a non-REM sleep period, a mental disorder can be accurately diagnosed.

Furthermore, with the appearance rate of γ waves in the first half of sleep, it is possible to determine the presence or absence of medication on the test subject related to a mental disorder.

Furthermore, together with the sleep electroencephalogram information based on which the analysis has been performed, α spindle waves detected from the sleep electroencephalogram information can be output, and, thus, information useful for diagnosing a mental disorder and the like can be provided. Furthermore, a reason based on which the mental disorder analysis apparatus 1 has diagnosed a mental disorder can be confirmed.

ANOTHER EXAMPLE

This example is different from the foregoing example in that the analyzing portion 102 is replaced by an analyzing portion 202 that determines the presence or absence of a mental disorder using δ waves in the sleep electroencephalogram information.

Figure 15:
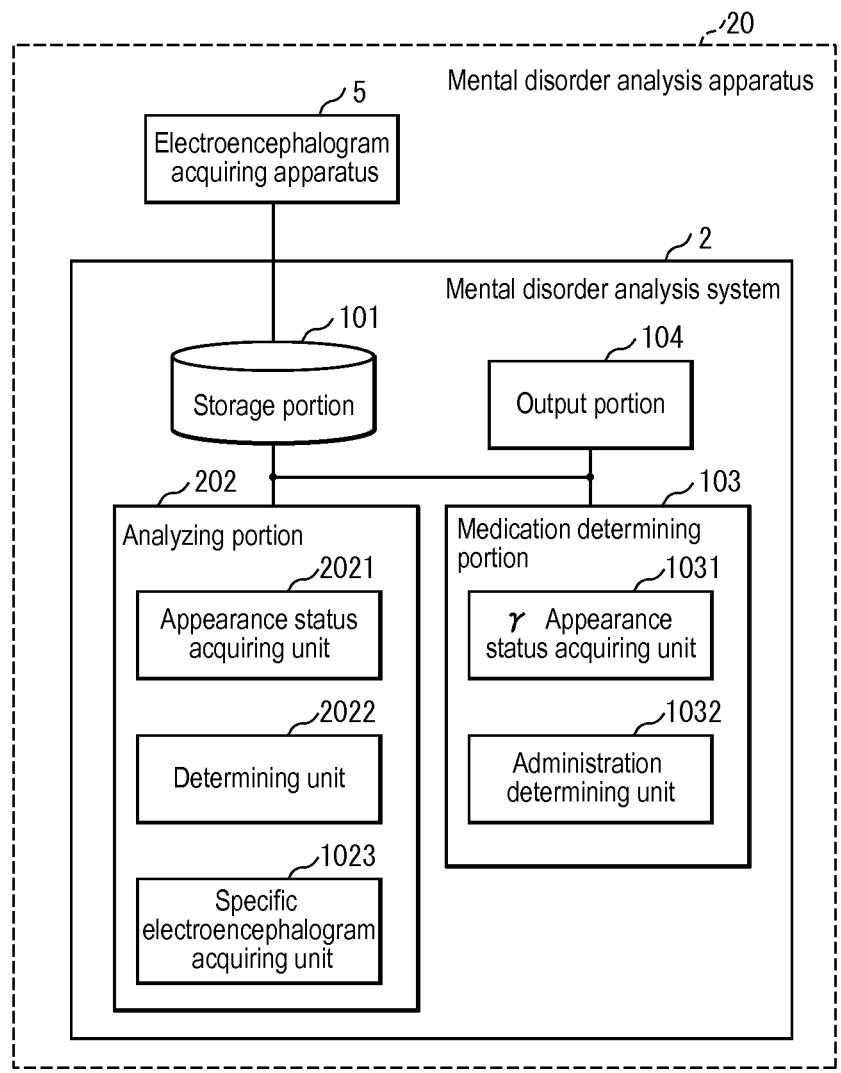
FIG. 15 is a block diagram of a mental disorder analysis system according to Another Example of the present invention.

FIG. 15 is a block diagram of a mental disorder analysis system 20 in this example. The mental disorder analysis system 20 uses a mental disorder analysis apparatus 2 including the analyzing portion 202, instead of the mental disorder analysis apparatus 1 including the analyzing portion 102 in the mental disorder analysis system 10 shown in FIG. 1, and has a configuration similar to that of the foregoing example except for the analyzing portion 202.

The analyzing portion 202 includes an appearance status acquiring unit 2021, a determining unit 2022, and the specific electroencephalogram acquiring unit 1023. The specific electroencephalogram acquiring unit 1023 is similar to the specific electroencephalogram acquiring unit 1023 in the Example, and, thus, a description thereof has been omitted.

In contrast to the foregoing example in which the analyzing portion 102 acquires information indicating an appearance status of α waves contained in the sleep electroencephalogram information in a non-REM sleep period, and determines the presence or absence of a mental disorder according to the acquired information, the analyzing portion 202 acquires information indicating an appearance rate or a power of δ waves contained in the sleep electroencephalogram information in a non-REM sleep period, in the sleep electroencephalogram information, and determines the presence or absence of a mental disorder according to the acquired information. The other portions of the configuration and the like are similar to those of the analyzing portion 102 described above, and, thus, a description thereof has been omitted.

The appearance status acquiring unit 2021 acquires information indicating an appearance status of δ waves contained in the sleep electroencephalogram information in a non-REM sleep period, in the sleep electroencephalogram information. For example, the appearance status acquiring unit 2021 acquires information indicating an appearance rate or a power of δ waves contained in the sleep electroencephalogram information in a non-REM sleep period, in the sleep electroencephalogram information. Here, as an example, cases will be respectively described in which, in order to determine the presence or absence of depression, which is one type of mental disorder, the appearance status acquiring unit 2021 acquires (4) information indicating an appearance rate of δ waves in a non-REM sleep period and (5) a power of δ waves in a non-REM sleep period.

(4) The Case in which Information Indicating an Appearance Rate of δ Waves is Acquired As a result of an in-depth study by the inventors, a new finding was obtained that δ waves seldom appear in a non-REM sleep period of a patient with depression, whereas the δ waves very often appear in a non-REM sleep period of a healthy person.

Figure 16:
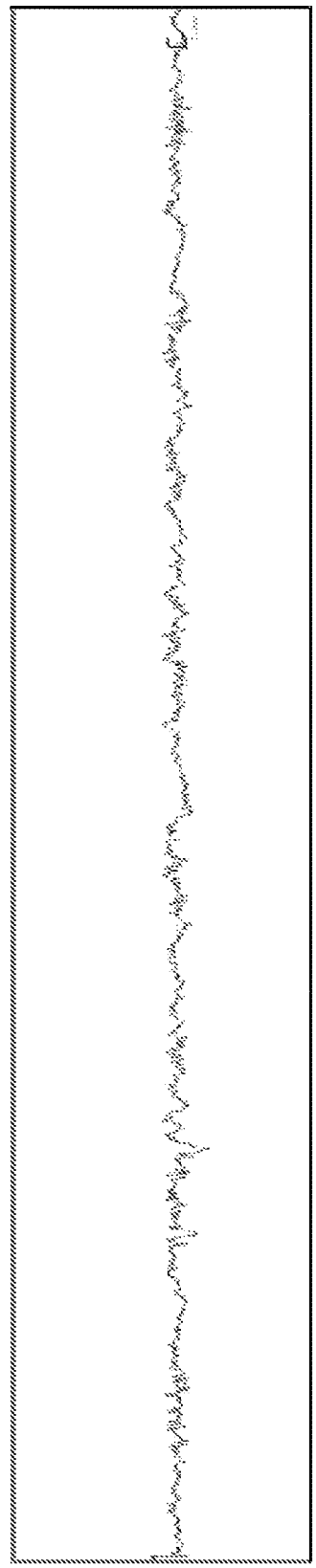
FIG. 16 is a graph showing an exemplary electroencephalogram of a patient with depression, illustrating the mental disorder analysis apparatus according to this example.

FIG. 16 is a graph showing an exemplary electroencephalogram in one epoch in a non-REM sleep period, in the sleep electroencephalogram information of a patient with depression.

Figure 17:
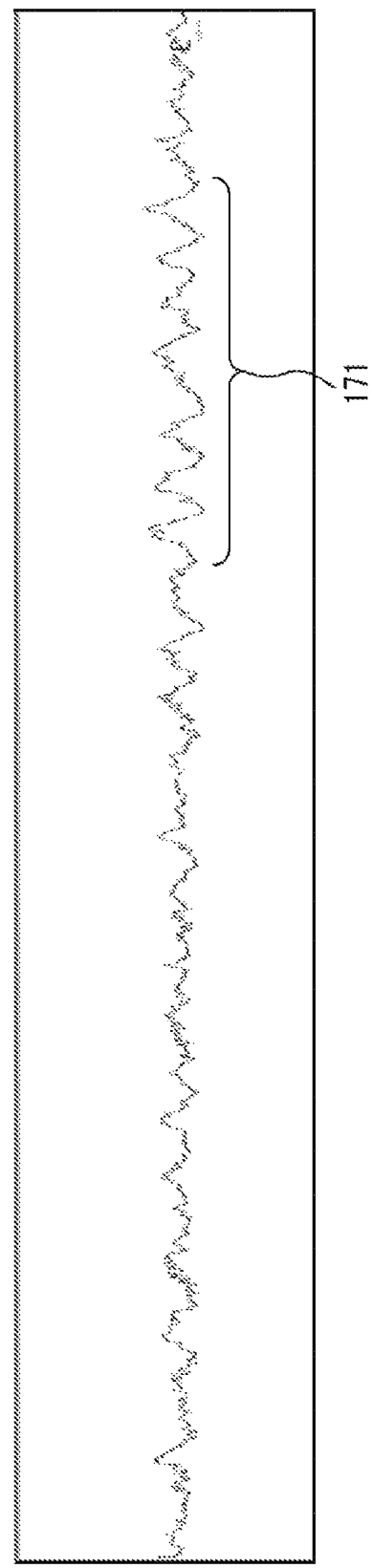
FIG. 17 is a graph showing an exemplary electroencephalogram of a healthy person, illustrating the mental disorder analysis apparatus according to this example.

FIG. 17 is a graph showing an exemplary electroencephalogram in one epoch in a non-REM sleep period, in the sleep electroencephalogram information of a healthy person. In the graph, a period 171 corresponds to a portion in which δ waves are detected.

As shown in FIG. 16, δ waves seldom appear in the electroencephalogram information in a non-REM sleep period of a patient with depression, whereas, as shown in FIG. 17, δ waves are detected in the electroencephalogram information in a non-REM sleep period of a healthy person.

Thus, the appearance status acquiring unit 2021 acquires information indicating an appearance rate of δ waves in the sleep electroencephalogram information in a non-REM sleep period, in the sleep electroencephalogram information. Here, as an example, the appearance status acquiring unit 2021 performs Fourier transform to detect a δ wave component in each of multiple periods forming a non-REM sleep period in the sleep electroencephalogram information. The processing and the like here are similar to those performed by the appearance status acquiring unit 1021 in the above-described case (2) except that the frequency band targeted for the acquisition is set to δ waves, and, thus, a detailed description thereof has been omitted.

(5) The Case in which a Power of δ Waves in a Non-REM Sleep Period is Acquired

As a result of an in-depth study by the inventors, a new finding was obtained that a power of δ waves in a non-REM sleep period of a healthy person is sufficiently larger than that of a patient with depression. The obtained finding was that, for example, the power in a REM sleep period is at most about 1 $\mu V^2$/min, whereas the power in a non-REM sleep period increases to about 7 to 10 $\mu V^2$/min.

Figure 18:
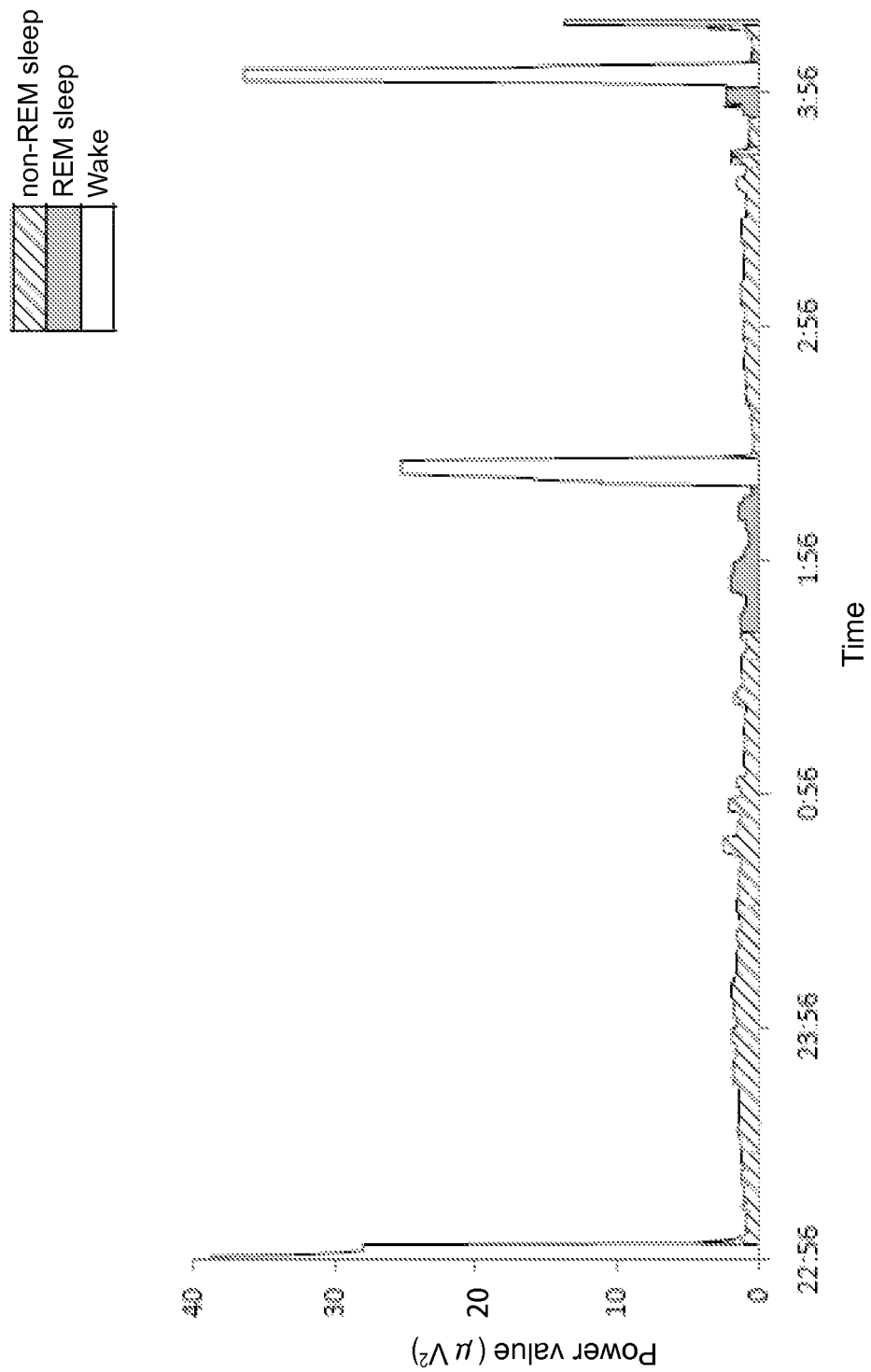
FIG. 18 is a graph showing the power of $\delta$ waves, illustrating the mental disorder analysis apparatus according to this example.

FIG. 18 is an exemplary graph in which δ wave peak values obtained by performing FFT on the epochs of the sleep electroencephalogram information of a patient with depression are arranged in a time series. In the graph, a non-REM sleep period is indicated as a hatched portion.

Figure 19:
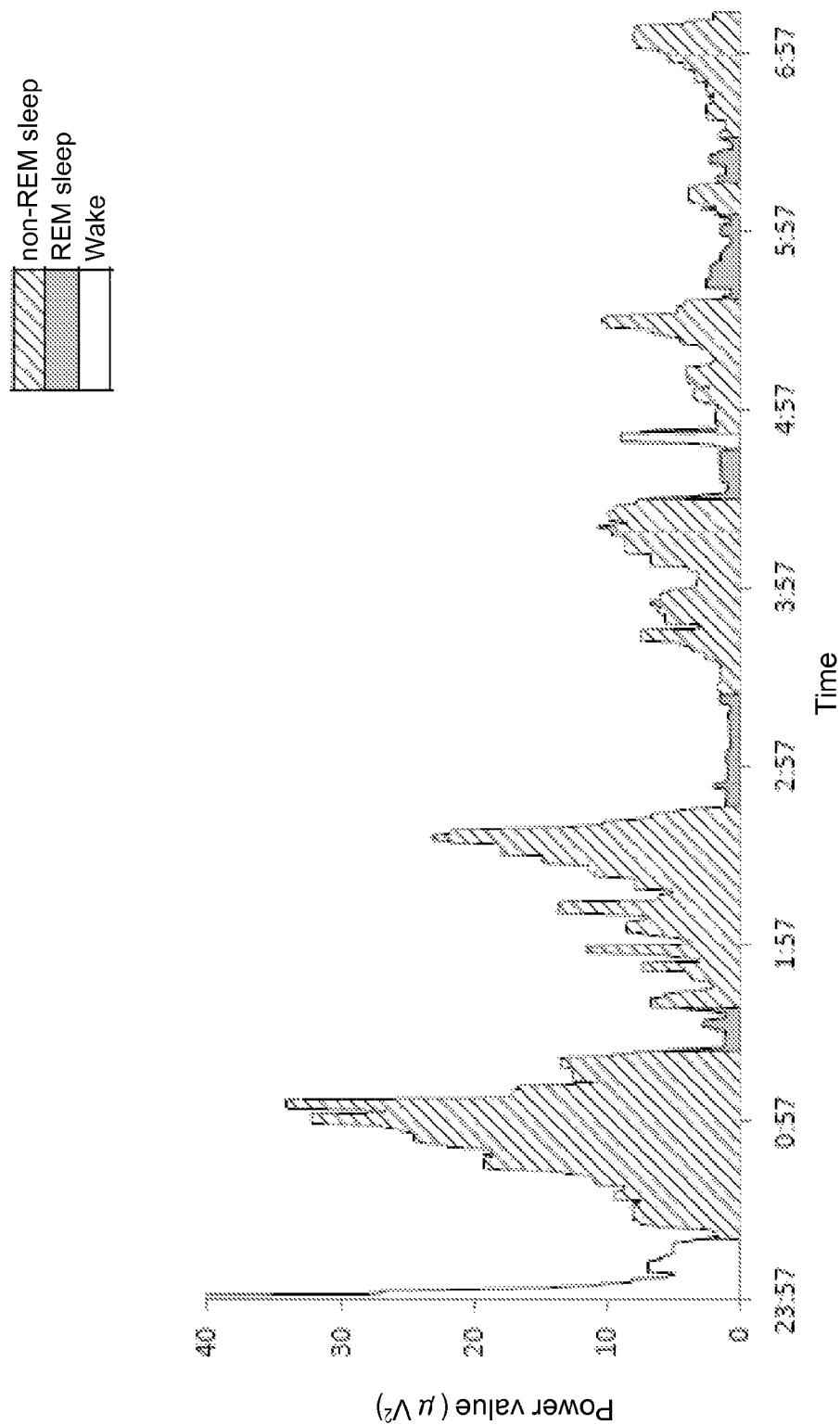
FIG. 19 is a graph showing the power of $\delta$ waves, illustrating the mental disorder analysis apparatus according to this example.

Furthermore, FIG. 19 is an exemplary graph in which δ wave peak values obtained by performing FFT on the epochs of the sleep electroencephalogram information of a healthy person are arranged in a time series. In the graph, a non-REM sleep period is indicated as a hatched portion.

As clearly seen from FIGS. 18 and 19, a healthy person has higher powers of δ waves in a non-REM sleep period.

Thus, the appearance status acquiring unit 2021 acquires information indicating a power of δ waves in the sleep electroencephalogram information in a non-REM sleep period, in the sleep electroencephalogram information. Here, as an example, the appearance status acquiring unit 2021 performs Fourier transform to detect a δ wave component in each of one or more periods forming a non-REM sleep period in the sleep electroencephalogram information, and acquires a level (value) such as peak of the detected δ wave component, as information indicating a power of δ waves in each period. The processing and the like here are similar to those performed by the appearance status acquiring unit 1021 in the above-described case (3) except that the frequency band targeted for the acquisition is set to δ waves, and, thus, a detailed description thereof has been omitted.

The appearance status acquiring unit 2021 may perform only one process or may perform both processes of the above-described processes (4) and (5).

The appearance status acquiring unit 2021 may be realized typically as an MPU, a memory, or the like. Typically, the processing procedure of the appearance status acquiring unit 2021 is realized by software, and the software is stored in a storage medium such as a ROM. Note that the processing procedure may be realized also by hardware (a dedicated circuit).

The determining unit 2022 determines the presence or absence of a mental disorder according to the information indicating an appearance status of δ waves acquired by the appearance status acquiring unit 2021. For example, the determining unit 2022 determines the presence or absence of a mental disorder according to the information indicating an appearance rate or a power of δ waves acquired by the appearance status acquiring unit 2021.

For example, if the appearance status acquiring unit 2021 acquires information indicating an appearance rate of δ waves in a non-REM sleep period as in (4) above, the determining unit 2022 reads a threshold value for the appearance rate of δ waves prepared in advance, and determines whether or not the value indicating the appearance rate of periods in which δ waves are detected exceeds the threshold value, the appearance rate being acquired by the appearance status acquiring unit 2021. If the value exceeds the threshold value, it is determined that the test subject associated with the sleep electroencephalogram information does not have depression. For example, the determining unit 2022 determines that the test subject does not have depression if the appearance rate of δ waves in a non-REM sleep period, which is the first cycle of sleep, is 10% or more. Furthermore, if one epoch has 30 seconds, and an average of integral values of δ waves respectively contained in the multiple epochs is 1.5 $\mu V^2$ or more, it may be determined that the test subject does not have depression.

Furthermore, for example, if the appearance status acquiring unit 2021 acquires the information indicating a power of a δ wave component in a non-REM sleep period as in (5) above, the determining unit 2022 reads a threshold value for the power of δ waves prepared in advance, and determines whether or not any δ wave component acquired in each period by the appearance status acquiring unit 2021 has a power exceeding the threshold value. If any δ wave component exceeds the threshold value, the determining unit 2022 determines that the test subject associated with the sleep electroencephalogram information does not have depression. The threshold value for the power in this case is, for example, 5 $\mu V^2$. Alternatively, in consideration of factors such as noise or measurement errors, it may be determined that any δ wave component acquired in each period has a power exceeding the threshold value, if the number of periods exhibiting a power exceeding the threshold value is a predetermined number or more. Furthermore, the determining unit 2022 may calculate an average value of the powers of δ waves in the respective periods, and determine whether or not this average value exceeds the predetermined threshold value, thereby determining whether or not any δ wave component acquired in each period by the appearance status acquiring unit 2021 has a power exceeding the threshold value. It will be appreciated that, if the average value exceeds the threshold value, a value exceeding the threshold value is included, and, thus, such determination eventually provides a similar determination result.

Note that, if the appearance status acquiring unit 2021 performs both the above-described processes (4) and (5), the determining unit 2022 may individually perform the above-described determination on each of the processing results, and acquire the respective determination results. Furthermore, a comprehensive determination result may be acquired by further using these determination results. For example, only if all the determination results on the respective multiple processes indicate that depression is present, a determination result that depression is present may be acquired. Furthermore, if the determination results on the respective multiple processes include both a determination result that depression is present and a determination result that depression is not present, a determination result that there is a possibility of depression or the like may be acquired.

The determining unit 2022 may be realized typically as an MPU, a memory, or the like. Typically, the processing procedure of the determining unit 2022 is realized by software, and the software is stored in a storage medium such as a ROM.

Note that the processing procedure may be realized also by hardware (a dedicated circuit).

Figure 20:
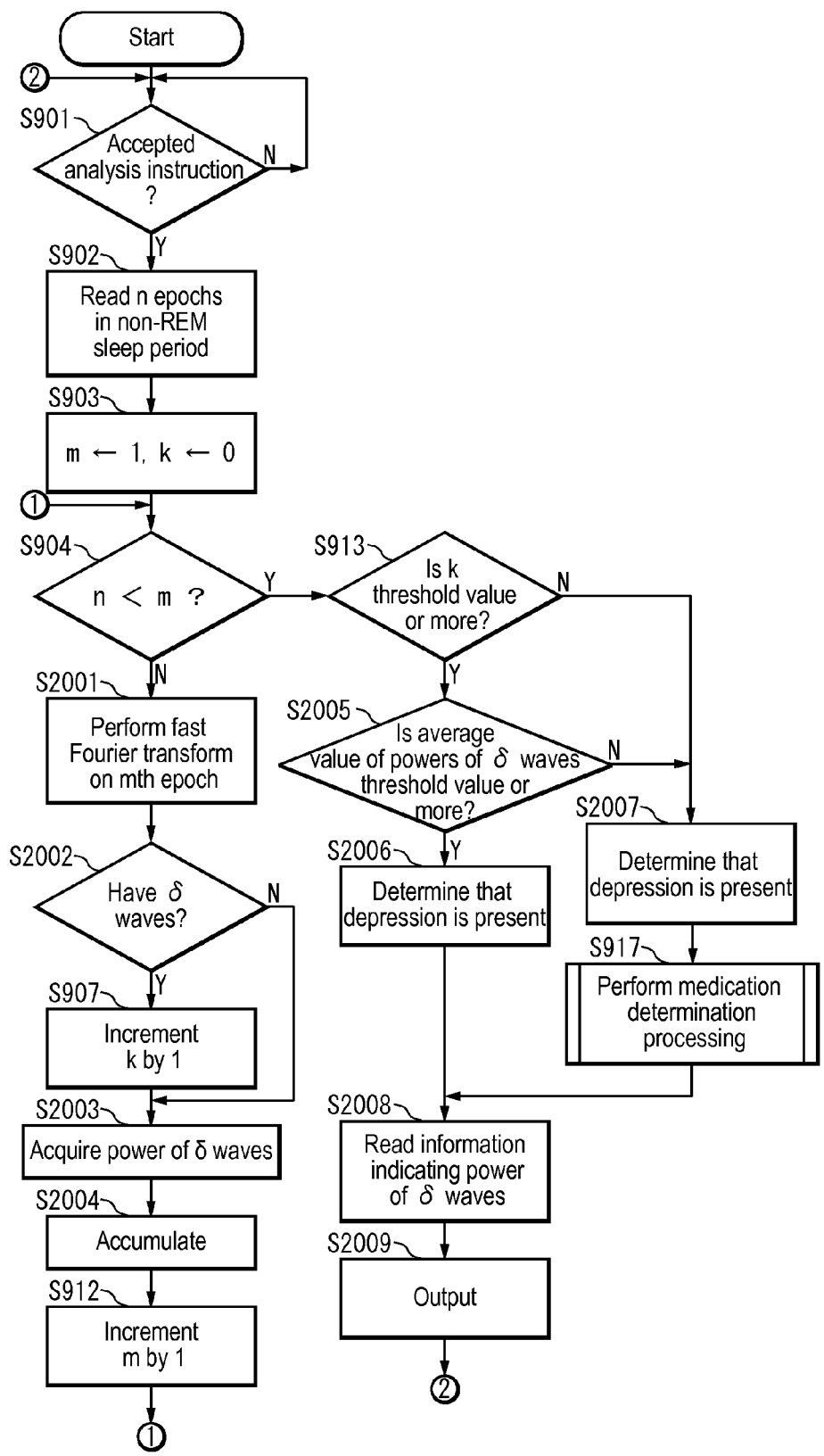
FIG. 20 is a flowchart showing an operation of the mental disorder analysis apparatus according to this example.

FIG. 20 is a flowchart showing an operation of the mental disorder analysis apparatus in this example. Hereinafter, this operation will be described. Note that, in FIG. 20, the same reference numerals as in FIG. 9 indicate the same or corresponding steps.

(Step S2001) The appearance status acquiring unit 2021 performs fast Fourier transform on the mth epoch.

(Step S2002) The appearance status acquiring unit 2021 determines whether or not δ waves are contained in the result of the fast Fourier transform in step S2001. This determination may be determination regarding whether or not δ waves at a predetermined power or more are contained. If such δ waves are contained, the procedure advances to step S907, and, if not, the procedure advances to step S2003.

(Step S2003) The appearance status acquiring unit 2021 acquires the power of δ waves from the result of the fast Fourier transform in step S2001.

(Step S2004) The appearance status acquiring unit 2021 accumulates the acquired power of δ waves in association with the mth epoch in a storage medium (not shown) or the like.

(Step S2005) The determining unit 2022 calculates an average value of the powers of δ waves in the respective epochs acquired in step S2003, and determines whether or not the average value is a predetermined threshold value or more. If the value is the threshold value or more, the procedure advances to step S2006, and, if not, the procedure advances to step S2007.

(Step S2006) The determining unit 2022 determines that the test subject targeted for the analysis does not have depression. Then, the procedure advances to step S2008.

(Step S2007) The determining unit 2022 determines that the test subject targeted for the analysis has depression. Then, the procedure advances to step S2008.

(Step S2008) The specific electroencephalogram acquiring unit 1023 reads information indicating the power of δ waves accumulated by the appearance status acquiring unit 2021 in association with each epoch in step S2004.

(Step S2009) The output portion 104 outputs information indicating the determination result acquired by the determining unit 2022 in step S2006 or S2007. Furthermore, the output portion 104 outputs a graph in which powers are shown as heights in a time series, the graph being generated using the information indicating the power of δ waves in each epoch acquired in step S2008. Furthermore, the output portion 104 outputs the determination result regarding drug administration in step S917. Then, the procedure returns to step S901.

Here, the process is terminated by powering off or an interruption to abort the process in the flowchart in FIG. 20.

Hereinafter, a specific example of this example will be described. Here, as in the Example above, it is assumed that an instruction for analyzing the sleep electroencephalogram information of a test subject is given, and FFT is performed on the first epoch read from a non-REM sleep period.

The appearance status acquiring unit 2021 determines whether or not δ waves are detected in the detected electroencephalogram information. Here, for example, it is determined whether or not δ waves with a peak value of 5 $\mu V^2$ or more are detected. Here, it is assumed that δ waves at the threshold value or more are detected. Thus, the appearance status acquiring unit 2021 increments the counter k by 1. Furthermore, the appearance status acquiring unit 2021 accumulates the δ wave peak value indicated by the FFT result in association with the start time of the epoch or the like in the storage medium (not shown) or the like.

Then, in a similar manner, the appearance status acquiring unit 2021 repeats similar processing on the second to the nth epochs. It is assumed that, as a result obtained by repeating the processing, the value of the counter k becomes "18". The information indicating the power of δ waves acquired by the appearance status acquiring unit 2021 is managed, for example, using a δ power management table similar to that in FIG. 13.

Next, the determining unit 2022 determines whether or not the value of the counter k is a predetermined threshold value or more. Here, if the threshold value is "15", it is determined that the value of the counter k "18" exceeds the threshold value.

Furthermore, the determining unit 2022 calculates an average value of the powers of δ waves acquired in the respective epochs by the appearance status acquiring unit 2021. Then, it is determined whether or not the average value is a predetermined threshold value or more. For example, if the threshold value is "1.0 $\mu V^2$", it is determined that the average value is the threshold value or more.

The determining unit 2022 acquires a determination result that the test subject is not a patient with depression, because the number of times of appearance of epochs in which the δ waves are detected is the threshold value or more, and because the average value of the powers of δ waves is the threshold value or more. The determination result that the test subject is not a patient with depression may be considered as a determination result that the possibility of being a patient with depression is high. The same is applied to descriptions in the other parts. If the value is less than the threshold value even in one of these conditions, a determination result that the test subject is a patient with depression is acquired.

The subsequent processing is similar to that in the Example above, and, thus, a description thereof has been omitted.

As described above, according to this example, since the electroencephalogram information during sleep is used to determine the presence or absence of a mental disorder, the influence on the electroencephalograms due to actions and the like from the outside on the test subject is reduced to the extent possible, and, thus, a mental disorder can be more accurately diagnosed. In particular, with the appearance status of δ waves in a non-REM sleep period, a mental disorder can be accurately diagnosed.

YET ANOTHER EXAMPLE

This example is different from the Example in that the analyzing portion 102 is replaced by an analyzing portion 302 that determines the presence or absence of a mental disorder using β waves in the sleep electroencephalogram information.

Figure 21:
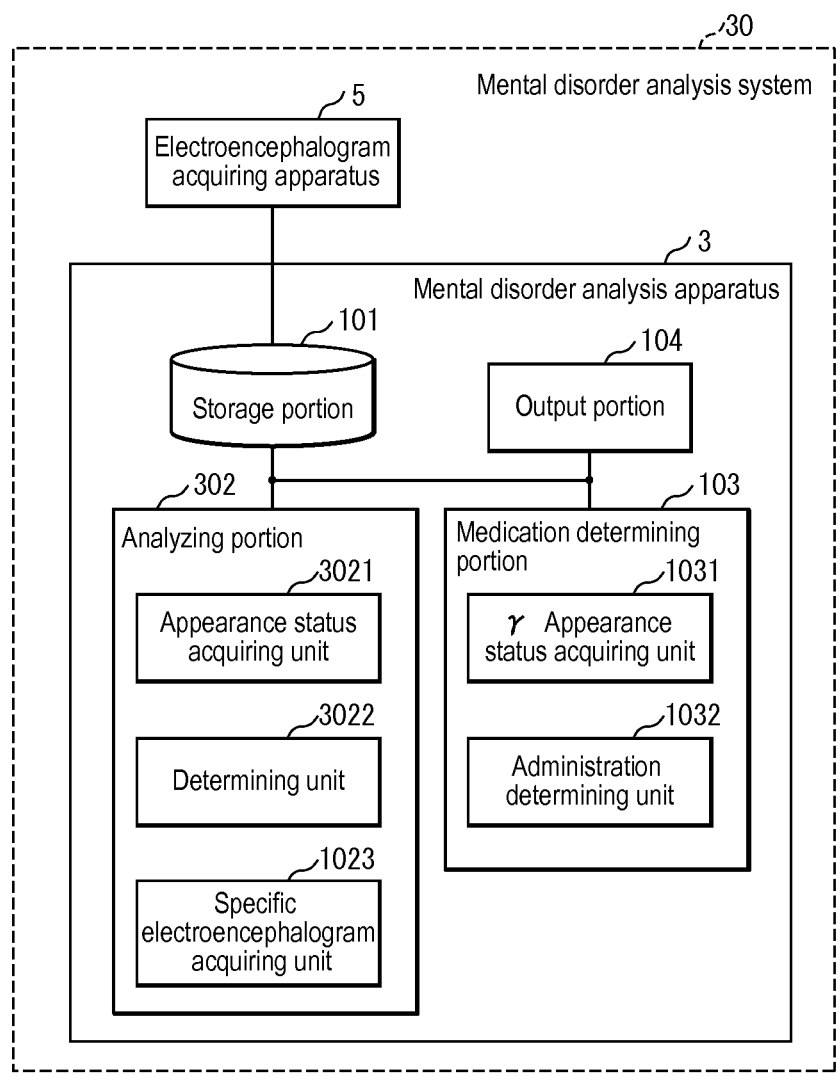
FIG. 21 is a block diagram of a mental disorder analysis system according to Yet Another Example of the present invention.

FIG. 21 is a block diagram of a mental disorder analysis system 30 in this example. The mental disorder analysis system 30 uses a mental disorder analysis apparatus 3 including the analyzing portion 302, instead of the mental disorder analysis apparatus 1 including the analyzing portion 102 in the mental disorder analysis system 10 shown in FIG. 1, and has a configuration similar to that of the foregoing example except for the analyzing portion 302.

The analyzing portion 302 includes an appearance status acquiring unit 3021, a determining unit 3022, and the specific electroencephalogram acquiring unit 1023. The specific electroencephalogram acquiring unit 1023 is similar to the specific electroencephalogram acquiring unit 1023 in the Example, and, thus, a description thereof has been omitted.

In contrast to the foregoing example in which the analyzing portion 102 acquires information indicating an appearance status of α waves contained in the sleep electroencephalogram information in a non-REM sleep period, and determines the presence or absence of a mental disorder according to the acquired information, the analyzing portion 302 acquires information indicating an appearance rate or a change in a waveform size of β waves contained in the sleep electroencephalogram information in a REM sleep period, in the sleep electroencephalogram information, and determines the presence or absence of a mental disorder according to the acquired information. The other portions of the configuration and the like are similar to those of the analyzing portion 102 described above, and, thus, a description thereof has been omitted.

The appearance status acquiring unit 3021 acquires information indicating an appearance status of β waves contained in the sleep electroencephalogram information in a REM sleep period, in the sleep electroencephalogram information. For example, the appearance status acquiring unit 3021 acquires information indicating an appearance rate or a change in a waveform size of β waves contained in the sleep electroencephalogram information in a REM sleep period, in the sleep electroencephalogram information. Here, as an example, cases will be respectively described in which, in order to determine the presence or absence of depression, which is one type of mental disorder, the appearance status acquiring unit 3021 acquires (6) information indicating an appearance rate of β waves in a REM sleep period and (7) information indicating a change in a waveform size of β waves in a REM sleep period.

(6) The Case in which Information Indicating an Appearance Rate of β Waves is Acquired As a result of an in-depth study by the inventors, a new finding was obtained that an appearance ratio of β waves in a REM sleep period of a patient with depression is very high. The appearance ratio of β waves is, for example, an appearance ratio of β waves with respect to the electroencephalogram information at all frequencies that have appeared. The appearance ratio of β waves may be considered as, for example, a ratio of power of β waves with respect to the sum of the powers of the electroencephalogram information at all frequencies.

Figure 22:
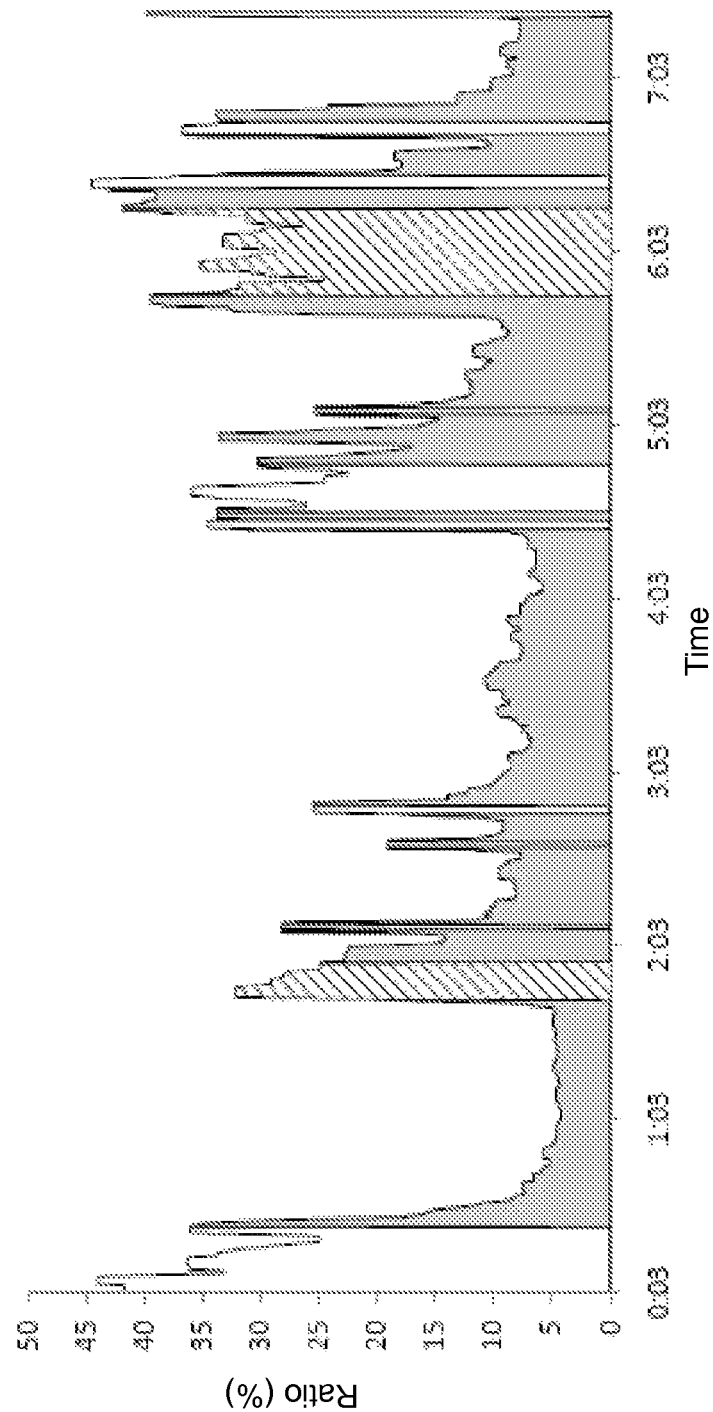
FIG. 22 is a graph showing the appearance rate of $\beta$ waves, illustrating the mental disorder analysis apparatus according to this example.

FIG. 22 is an exemplary graph in which ratios of β waves obtained by performing FFT on the epochs of the sleep electroencephalogram information of a patient with depression are arranged in a time series. In the graph, a REM sleep period is indicated as a hatched portion.

Figure 23:
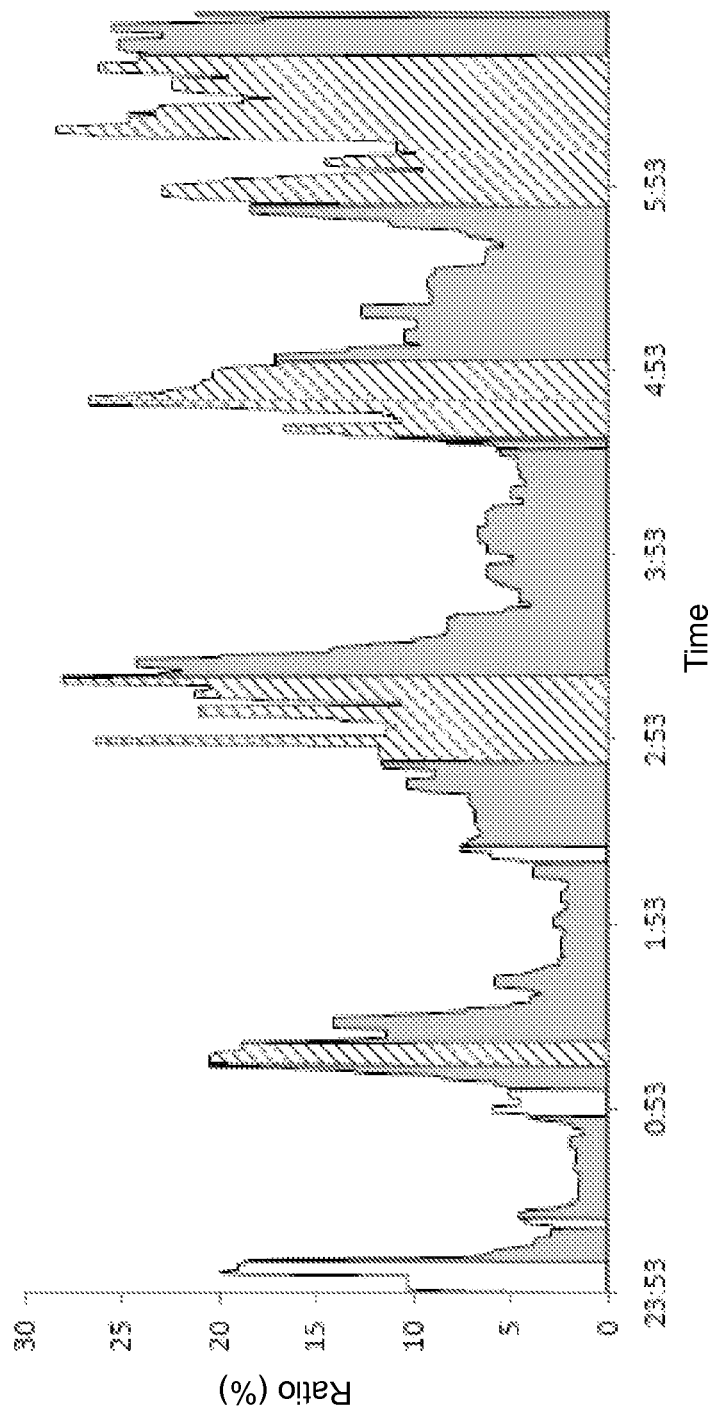
FIG. 23 is a graph showing the appearance rate of $\beta$ waves, illustrating the mental disorder analysis apparatus according to this example.

Furthermore, FIG. 23 is an exemplary graph in which ratios of β waves obtained by performing FFT on the epochs of the sleep electroencephalogram information of a healthy person are arranged in a time series. In the graph, a REM sleep period is indicated as a hatched portion.

As clearly seen from FIGS. 22 and 23, a patient with depression has higher ratios of β waves in a REM sleep period, and often has a ratio exceeding 30%. On the other hand, a healthy person does not have a ratio of β waves exceeding 30%.

Thus, the appearance status acquiring unit 3021 acquires information indicating an appearance rate of β waves in the sleep electroencephalogram information in a REM sleep period, in the sleep electroencephalogram information. Here, as an example, the appearance status acquiring unit 3021 performs Fourier transform to acquire an appearance ratio of a β wave component in each of multiple periods forming a REM sleep period in the sleep electroencephalogram information, and acquires information indicating an appearance rate of periods in which the acquired ratio is a predetermined threshold value or more, as information indicating an appearance rate of β waves. The processing and the like here are similar to those performed by the appearance status acquiring unit 1021 in the above-described case (2) except that the frequency band targeted for the acquisition is set to β waves, for example, and, thus, a detailed description thereof has been omitted.

(7) The Case in which Information Indicating a Waveform Size or a Change in The Size of β Waves in a REM Sleep Period As a result of an in-depth study by the inventors, a new finding was obtained that the shape of β waves that appear in a REM sleep period of a patient with depression is disturbed, and, as a result, the waveform size increases, and a change in the size becomes large.

Figure 24:
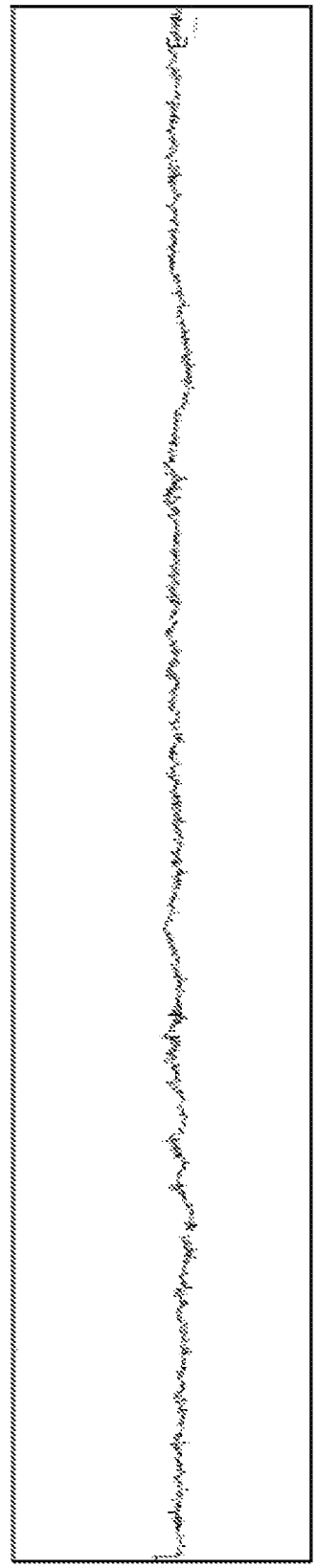
FIG. 24 is a graph showing an exemplary electroencephalogram of a patient with depression, illustrating the mental disorder analysis apparatus according to this example.

FIG. 24 is a graph showing an exemplary electroencephalogram in one epoch in a REM sleep period of the sleep electroencephalogram information of a patient with depression.

Figure 25:
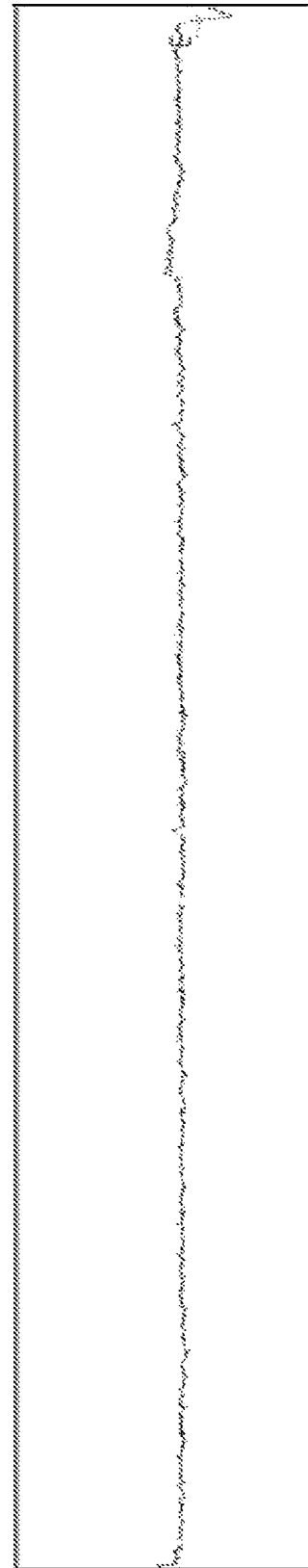
FIG. 25 is a graph showing an exemplary electroencephalogram of a healthy person, illustrating the mental disorder analysis apparatus according to this example.

FIG. 25 is a graph showing an exemplary electroencephalogram in one epoch in a REM sleep period of the sleep electroencephalogram information of a healthy person.

As seen from FIGS. 24 and 25, both a healthy person and a patient with depression have β waves in the electroencephalogram information in a REM sleep period. Meanwhile, in the case of the β waves of a patient with depression, the output is large, a change in the waveform is large, and the waveform is disturbed, compared with a healthy person.

Thus, the appearance status acquiring unit 3021 acquires information indicating a waveform size or a change in the size of β waves in the sleep electroencephalogram information in a REM sleep period, in the sleep electroencephalogram information. For example, the waveform of β waves is extracted using a filter or the like from the sleep electroencephalogram information in one or more periods in a REM sleep period, and information indicating a difference between amplitudes of adjacent waves in the extracted β waves is acquired as information indicating a change in the waveform size. Alternatively, a sum of the differences between the acquired amplitudes or the like is acquired as information indicating a change in the waveform size. Alternatively, a variance or the like indicating dispersion in amplitudes or peak values may be acquired as a value indicating a change in the waveform size. Note that the entire electroencephalogram information in a REM sleep period may be considered as β waves, and the above-described process that extracts β waves using a filter or the like may be omitted.

The appearance status acquiring unit 3021 may perform only one process or may perform both processes of the above-described processes (6) and (7).

The appearance status acquiring unit 3021 may be realized typically as an MPU, a memory, or the like. Typically, the processing procedure of the appearance status acquiring unit 3021 is realized by software, and the software is stored in a storage medium such as a ROM. Note that the processing procedure may be realized also by hardware (a dedicated circuit).

The determining unit 3022 determines the presence or absence of a mental disorder according to the information indicating an appearance status of β waves acquired by the appearance status acquiring unit 3021. For example, the determining unit 3022 determines the presence or absence of a mental disorder according to the information indicating an appearance rate or a change magnitude in a waveform of β waves acquired by the appearance status acquiring unit 3021.

For example, if the appearance status acquiring unit 3021 acquires information indicating an appearance rate of β waves in a REM sleep period as in (6) above, the determining unit 3022 reads a threshold value for the appearance rate of β waves prepared in advance, and determines whether or not the value indicating the appearance rate of periods in which β waves are detected exceeds the threshold value, the appearance rate being acquired by the appearance status acquiring unit 3021. If the value exceeds the threshold value, the determining unit 3022 determines that the test subject associated with the sleep electroencephalogram information has depression. The threshold value for the appearance rate of β waves is, for example, about 35% or more. In order to diagnose a patient with serious depression, the threshold value may be about 50%.

Furthermore, for example, if the appearance status acquiring unit 3021 acquires information indicating a change in a waveform size of β waves in a REM sleep period as in (7) above, the determining unit 3022 reads a threshold value for the change in a waveform size or the power of β waves prepared in advance, and determines whether or not the test subject associated with the sleep electroencephalogram information has depression using this threshold value. For example, if the power of β waves is the predetermined threshold value or more, it may be determined that depression is present. For example, the threshold value for the power of β waves is 0.3 $\mu V^2$. Furthermore, for example, if the information indicating a change in a waveform size of β waves is information indicating a difference between the amplitudes or peak values of adjacent waves in one or more periods as described above, it is determined whether or not any difference between the amplitudes or peak values exceeds the threshold value. If any difference exceeds the threshold value, it is determined that the test subject has depression. If not, it may be determined that depression is not present. Here, whether or not any difference exceeds the threshold value may be considered as whether or not the number of differences exceeding the threshold value is a predetermined number or more. Furthermore, for example, if the information indicating a change in a waveform size of β waves is a value indicating a sum of the differences between the amplitudes or the like or a variance of the differences between the amplitudes or the like as described above, it may be determined whether or not this value exceeds the threshold value, and, if the value exceeds the threshold value, it may be determined that depression is present.

Note that, if the appearance status acquiring unit 3021 performs both the above-described processes (6) and (7), the determining unit 3022 may individually perform the above-described determination on each of the processing results, and acquire the respective determination results. Furthermore, a comprehensive determination result may be acquired by further using these determination results. For example, only if all the determination results on the respective multiple processes indicate that depression is present, a determination result that depression is present may be acquired. Furthermore, if the determination results on the respective multiple processes include both a determination result that depression is present and a determination result that depression is not present, a determination result that there is a possibility of depression or the like may be acquired. Furthermore, since the power of β waves significantly changes between a non-REM sleep period and a REM sleep period of a patient with depression, the determining unit 3022 may acquire a determination result that depression is present if a change in the power of β waves between a non-REM sleep period and a REM sleep period is a predetermined threshold value or more.

The determining unit 3022 may be realized typically as an MPU, a memory, or the like. Typically, the processing procedure of the determining unit 3022 is realized by software, and the software is stored in a storage medium such as a ROM. Note that the processing procedure may be realized also by hardware (a dedicated circuit).

Figure 26:
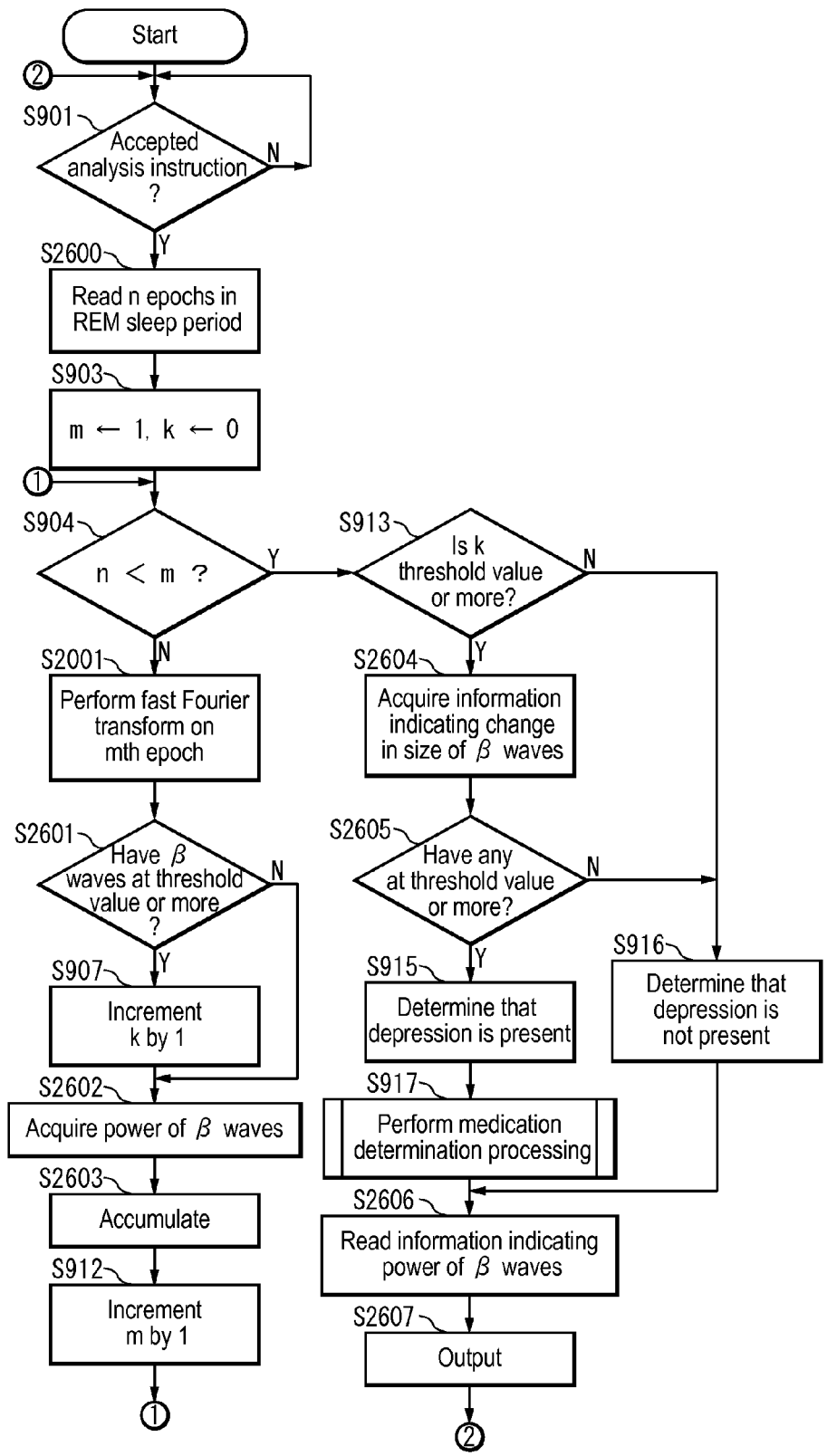
FIG. 26 is a flowchart showing an operation of the mental disorder analysis apparatus according to this example.

FIG. 26 is a flowchart showing an operation of the mental disorder analysis apparatus in this example. Hereinafter, this operation will be described. Note that, in FIG. 26, the same reference numerals as in FIGS. 9 and 20 indicate the same or corresponding steps.

(Step S2600) The appearance status acquiring unit 3021 reads electroencephalogram information for n epochs (n is an integer of 2 or more) in a REM sleep period, from the sleep electroencephalogram information stored in the storage portion 101. The read electroencephalogram information is temporarily stored in a memory (not shown) or the like.

(Step S2601) The appearance status acquiring unit 3021 determines whether or not a ratio of β waves is a predetermined threshold value or more, in the result of the fast Fourier transform in step S2001. Here, the ratio is, for example, a ratio of β waves with respect to the sum of all powers of the waveform obtained by FFT. If the ratio is the predetermined threshold value or more, the procedure advances to step S907, and, if not, the procedure advances to step S2602.

(Step S2602) The appearance status acquiring unit 3021 acquires the power of β waves from the result of the fast Fourier transform in step S2001.

(Step S2603) The appearance status acquiring unit 3021 accumulates the acquired power of β waves in association with the mth epoch in a storage medium (not shown) or the like.

(Step S2604) The appearance status acquiring unit 3021 acquires information indicating a change in a waveform size of β waves for a period of time having a predetermined length, in the sleep electroencephalogram information in a REM sleep period. Here, for example, β waves are extracted using a filter or the like in the first epoch of the epochs read in step S2600, and a difference between amplitudes of adjacent waves is sequentially calculated. Then, the difference between the amplitudes is acquired as information indicating a change in the waveform size.

(Step S2605) The determining unit 3022 determines whether or not any value indicating a change in the waveform size acquired in step S2604 is the predetermined threshold value or more. Here, for example, it may be determined whether or not the number of values at the threshold value or more is a predetermined number or more. If the number is the threshold value or more, the procedure advances to step S915, and, if not, the procedure advances to step S916.

(Step S2606) The specific electroencephalogram acquiring unit 1023 reads information indicating the power of β waves accumulated by the appearance status acquiring unit 3021 in association with each epoch in step S2603.

(Step S2607) The output portion 104 outputs information indicating the determination result acquired by the determining unit 3022 in step S915 or S916. Furthermore, the output portion 104 outputs a graph in which powers are shown as heights in a time series, the graph being generated using the information indicating the power of β waves in each epoch acquired in step S2606. Furthermore, the output portion 104 outputs the determination result regarding drug administration in step S917. Then, the procedure returns to step S901.

Hereinafter, a specific example of this example will be described. Here, as in the specific example of the Example above, it is assumed that an instruction for analyzing the sleep electroencephalogram information of a test subject is given, and FFT is performed on the first epoch read from a REM sleep period.

The appearance status acquiring unit 3021 acquires a ratio of β waves with respect to the sum of all powers of the waveform obtained by FFT, as an appearance ratio of β waves, and determines whether or not this ratio is a predetermined threshold value or more. Here, for example, it is determined whether or not the ratio of β waves is 30% or more. Here, it is assumed that the ratio of β waves detected is the threshold value or more. Thus, the appearance status acquiring unit 3021 increments the counter k by 1. Furthermore, the appearance status acquiring unit 3021 accumulates the β wave peak value indicated by the FFT result in association with the start time of the epoch or the like in a storage medium (not shown) or the like.

Then, in a similar manner, the appearance status acquiring unit 3021 repeats similar processing on the second to the nth epochs. It is assumed that, as a result obtained by repeating the processing, the value of the counter k becomes "18". The information indicating the power of β waves acquired by the appearance status acquiring unit 3021 is managed, for example, using a β power management table similar to that in FIG. 13.

Next, the determining unit 3022 determines whether or not the value of the counter k is a predetermined threshold value or more. Here, if the threshold value is "15", it is determined that the value of the counter k "18" exceeds the threshold value.

Next, the appearance status acquiring unit 3021 extracts β waves using a filter or the like in the first epoch, and sequentially calculates a difference between amplitudes of adjacent waves in the acquired β waves.

Then, the determining unit 3022 determines whether or not each of absolute values of the differences between the amplitudes calculated by the appearance status acquiring unit 3021 is a predetermined threshold value or more, and counts the number of differences between the amplitudes at the threshold value or more. Then, it is determined whether or not this number is a predetermined value or more. For example, it is assumed that the number exceeds the predetermined value.

The determining unit 3022 acquires a determination result that the test subject is a patient with depression, because the number of times of appearance of epochs in which the appearance ratio of β waves is the threshold value or more, that is, the value of the counter k "18" is the threshold value or more, and because, in the information indicating a change in a waveform size of β waves, that is, in the information indicating a difference between amplitudes of adjacent waves, the number of changes or differences at the threshold value or more is the predetermined number or more. If the value is less than the threshold value even in one of these conditions, a determination result that the test subject is not a patient with depression is acquired.

The subsequent processing is similar to that in the Example above, and, thus, a description thereof has been omitted.

As described above, according to this example, since the electroencephalogram information during sleep is used to determine the presence or absence of a mental disorder, the influence on the electroencephalograms due to actions and the like from the outside on the test subject is reduced to the extent possible, and, thus, a mental disorder can be more accurately diagnosed. In particular, with the appearance status of β waves in a REM sleep period, a mental disorder can be accurately diagnosed.

In the foregoing examples, the analyzing portion may acquire two or more pieces of information from among: information indicating an appearance rate or a power of α waves contained in the sleep electroencephalogram information in a non-REM sleep period, in the sleep electroencephalogram information; information indicating an appearance rate or a power of δ waves contained in the sleep electroencephalogram information in a non-REM sleep period, in the sleep electroencephalogram information; and information indicating an appearance rate or a change in a waveform size of β waves contained in the sleep electroencephalogram information in a REM sleep period, in the sleep electroencephalogram information; and determine the presence or absence of a mental disorder according to a combination of the acquired pieces of information. That is to say, two or more processes that analyze the sleep electroencephalogram information described in the foregoing examples may be performed in an appropriate combination, and a mental disorder may be diagnosed according to the combination of the analysis results. For example, two or more pieces of such information may be acquired, the presence or absence of a mental disorder may be determined as described above, and the presence or absence of a mental disorder may be finally determined according to the determination results. For example, it may be determined that a mental disorder is present only if all of these determination results indicate that a mental disorder is present. Alternatively, it may be determined that a mental disorder is not present only if none of these determination results indicates that a mental disorder is present. Furthermore, if there are both a determination result that a mental disorder is present and a determination result that a mental disorder is not present, information indicating that there is a possibility of a mental disorder or the like may be output.

Note that, in order to achieve this sort of configuration, for example, it is sufficient that the mental disorder analysis apparatus is provided with an analyzing portion having a configuration similar to that of the analyzing portion 102, the analyzing portion 202, or the analyzing portion 302 shown in the foregoing examples. In this case, the configurations for performing common operations may be shared.

Furthermore, in this case, in particular, the specific electroencephalogram acquiring unit of the analyzing portion as described above may acquire electroencephalogram information in multiple specific frequency bands from the sleep electroencephalogram information, and the output portion 104 may output the electroencephalogram information in the multiple frequency bands. Accordingly, information useful for diagnosing a mental disorder and the like can be provided, and a reason based on which the mental disorder analysis apparatus has diagnosed a mental disorder can be confirmed.

FURTHER EXAMPLE

This example of the present invention is applied when determining the presence or absence of a mental disorder of the test subject using electroencephalograms during sleep. That is to say, based on the finding that waveforms of the electroencephalograms during sleep are different between a patient with a mental disorder and a healthy person, this example is used to properly determine whether or not a mental disorder is present, by performing output such that these waveforms can be easily compared with the electroencephalogram during sleep of a test subject.

Figure 29:
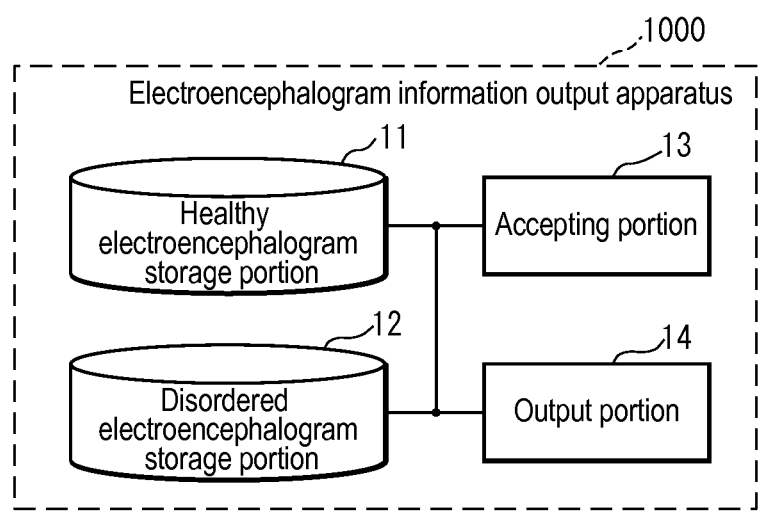
FIG. 29 is a block diagram of an electroencephalogram information output apparatus according to Further Example of the present invention.

FIG. 29 is a block diagram of an electroencephalogram information output apparatus 1000 in this example.

The electroencephalogram information output apparatus 1000 includes a healthy electroencephalogram storage portion 11, a disordered electroencephalogram storage portion 12, an accepting portion 13, and an output portion 14.

In the healthy electroencephalogram storage portion 11, one or more pieces of healthy electroencephalogram information are stored. The healthy electroencephalogram information is information on electroencephalograms during sleep of a healthy person. A healthy person described here is, for example, a person free from at least a predetermined mental disorder. Examples of the predetermined mental disorder include depression, schizophrenia, panic disorder, and the like. The electroencephalogram information is information on electroencephalograms. The electroencephalogram information is, for example, information on output from an electroencephalograph or the like. The electroencephalogram information is, for example, information having one or more output values (e.g., voltage values) of an electroencephalograph in association with a time series. The electroencephalogram information may be, for example, information having sampling times and output values of the electroencephalograms. Note that the electroencephalogram information may be image data indicating an electroencephalogram. The same is applied to the description below. The image data may be vector data or may be raster data. Furthermore, the electroencephalogram information may be data obtained by performing processing such as noise reduction on actual measurement values actually acquired using an electroencephalograph or the like. The same is applied to the description below. The healthy electroencephalogram information may be part or the whole of the electroencephalogram information acquired during sleep of one healthy person. Furthermore, the healthy electroencephalogram information may be part of the electroencephalogram information in a predetermined cycle, phase, period, or the like during sleep. For example, it may be electroencephalogram information in the first cycle of sleep, electroencephalogram information during REM sleep, electroencephalogram information during non-REM sleep, electroencephalogram information after the elapse of a predetermined period of time after the start of sleep, or the like. Furthermore, the healthy electroencephalogram information may be electroencephalogram information in a predetermined frequency band in the electroencephalogram information during sleep. The electroencephalogram information in a predetermined frequency band refers to, for example, α waves, β waves, γ waves, δ waves, or the like. Note that, in the healthy electroencephalogram storage portion 11, electroencephalogram information acquired in different cycles, different phases, or the like or electroencephalogram information in different frequency bands may be stored in a mixed manner. In this case, the healthy electroencephalogram information may have identifying information indicating the cycle, phase, period, or the like of the electroencephalogram information, or identifying information indicating the frequency band of the information. The healthy electroencephalogram information is preferably typical electroencephalogram information during sleep of a healthy person. Furthermore, a start position (start time) or an end position (end time) of a predetermined cycle, phase, or period of the healthy electroencephalogram information may be associated with, for example, so-called index information or marker information that can be used to determine a read start position or the like. The healthy electroencephalogram storage portion 11 is preferably a non-volatile storage medium, but may be realized also as a volatile storage medium.

In the disordered electroencephalogram storage portion 12, one or more pieces of disordered electroencephalogram information are stored. The disordered electroencephalogram information is information on electroencephalograms during sleep of a patient with a mental disorder. A patient with a mental disorder described here is, for example, a person having at least a predetermined mental disorder. Examples of the predetermined mental disorder include depression, schizophrenia, panic disorder, and the like, as described above. The disordered electroencephalogram information may be part or the whole of the electroencephalogram information acquired during sleep of one patient with a mental disorder. Furthermore, the disordered electroencephalogram information may be part of the electroencephalogram information in a predetermined cycle, phase, period, or the like during sleep. Furthermore, the disordered electroencephalogram information may be electroencephalogram information in a predetermined frequency band in the electroencephalogram information during sleep. Note that, in the disordered electroencephalogram storage portion 12, electroencephalogram information acquired in different cycles, different phases, or the like or electroencephalogram information in different frequency bands may be stored in a mixed manner. In this case, the disordered electroencephalogram information may have identifying information indicating the cycle, phase, period, or the like of the electroencephalogram information, or identifying information indicating the frequency band of the information. Furthermore, a start position (start time) or an end position (end time) of a predetermined cycle, phase, or period of the disordered electroencephalogram information may be associated with, for example, so-called index information or marker information that can be used to determine a read start position or the like. Furthermore, in the disordered electroencephalogram storage portion 12, electroencephalogram information during sleep of patients having different mental disorders may be stored. In this case, the disordered electroencephalogram information may have identifying information for identifying a mental disorder. The disordered electroencephalogram storage portion 12 is preferably a non-volatile storage medium, but may be realized also as a volatile storage medium.

The accepting portion 13 accepts one or more pieces of test subject electroencephalogram information. The test subject electroencephalogram information is information on electroencephalograms during sleep of a test subject. Here, the test subject is a person targeted for the diagnosis of a predetermined mental disorder. The test subject electroencephalogram information is similar to the healthy electroencephalogram information, the disordered electroencephalogram information, or the like described above, and, thus, a detailed description thereof has been omitted. The test subject electroencephalogram information may have identifying information of a test subject, identifying information of a mental disorder targeted for the diagnosis, or the like. Here, accepting is a concept that includes reading of test subject electroencephalogram information from a storage medium (not shown) or the like and receiving of the information transmitted from an electroencephalograph or other apparatuses and the like. The accepting portion 13 may be realized as a device driver for a unit for reading information from a storage medium, a communication unit, or their control software, and the like.

The output portion 14 reads the healthy electroencephalogram information stored in the healthy electroencephalogram storage portion 11 and the disordered electroencephalogram information stored in the disordered electroencephalogram storage portion 12, and outputs a waveform indicated by the read healthy electroencephalogram information (hereinafter, referred to as a "healthy electroencephalogram") and a waveform indicated by the read disordered electroencephalogram information (hereinafter, referred to as a "disordered electroencephalogram") in juxtaposition. The output portion 14 may further display scales, legends, titles, or the like put on the waveforms. When outputting the waveforms in juxtaposition, the output portion 14 preferably employs the same units for the horizontal and vertical axes, the same intervals of the scales, and the like. Output described here may be, for example, display of a waveform on a monitor or the like, or printing of a waveform on paper, a resin sheet, or the like. Furthermore, it may be processing in which data for display or printing (e.g., image data, data in an electronic document format, etc.) is generated and transmitted, or accumulated in a storage medium (not shown) or the like. Output by the output portion 14 is used, for example, to diagnose a mental disorder. The output portion 14 outputs, for example, the healthy electroencephalogram and the disordered electroencephalogram with the horizontal axis indicating time and the vertical axis indicating waveform output. When outputting the waveforms, the output portion 14 may generate and output axes indicating time and waveform output. The output portion 14 outputs, for example, the healthy electroencephalogram and the disordered electroencephalogram in vertical juxtaposition. Furthermore, the healthy electroencephalogram and the disordered electroencephalogram may be output in an overlapping manner. The output portion 14 may output the healthy electroencephalogram and the disordered electroencephalogram in different colors, different line types, or the like.

If the healthy electroencephalogram information and the disordered electroencephalogram information have identifying information of a cycle, a phase, or the like, identifying information of a frequency band, or the like as described above, the output portion 14 may output waveforms of the healthy electroencephalogram information and the disordered electroencephalogram information matching at least part of these pieces of identifying information. Furthermore, portions of waveforms matching information that can be used to determine a read start position, such as index, associated with the healthy electroencephalogram information and the disordered electroencephalogram information may be output. Furthermore, the output portion 14 may output waveforms of the healthy electroencephalogram information and the disordered electroencephalogram information having identifying information of a cycle, a phase, a frequency band, or the like specified by the user. Furthermore, the output portion 14 may output portions of waveforms of the healthy electroencephalogram information and the disordered electroencephalogram information having information that can be used to determine a read start position, such as index, specified by an instruction input by the user. Alternatively, waveforms indicated by the healthy electroencephalogram information and the disordered electroencephalogram information in a time (period) specified by an instruction input by the user may be output. Note that the instruction from the user may be accepted, for example, by an instruction accepting portion (not shown) or the like for accepting an instruction. Furthermore, if the healthy electroencephalogram information and the disordered electroencephalogram information have identifying information of a mental disorder as described above, the waveform indicating the healthy electroencephalogram information and the waveform indicating the disordered electroencephalogram information having identifying information of the same mental disorder may be output.

Furthermore, the output portion 14 may output a waveform indicated by the test subject electroencephalogram information accepted by the accepting portion 13 (hereinafter, "test subject electroencephalogram") in juxtaposition with the healthy electroencephalogram information and the disordered electroencephalogram information. For example, the output portion 14 may output the healthy electroencephalogram, the disordered electroencephalogram, and the test subject electroencephalogram in vertical juxtaposition. In particular, when outputting the waveforms in vertical juxtaposition, the output portion 14 preferably outputs them such that the test subject electroencephalogram is positioned between the healthy electroencephalogram and the disordered electroencephalogram. Accordingly, it can be easily determined which of the electroencephalogram of a healthy person and the electroencephalogram of a patient with a mental disorder is closer to the test subject electroencephalogram.

The output portion 14 may be considered to include or not to include an output device, such as a display screen or a printer. The output portion 14 may be realized as driver software for an output device, or a combination of driver software for an output device, the output device, and the like.

Figure 30:
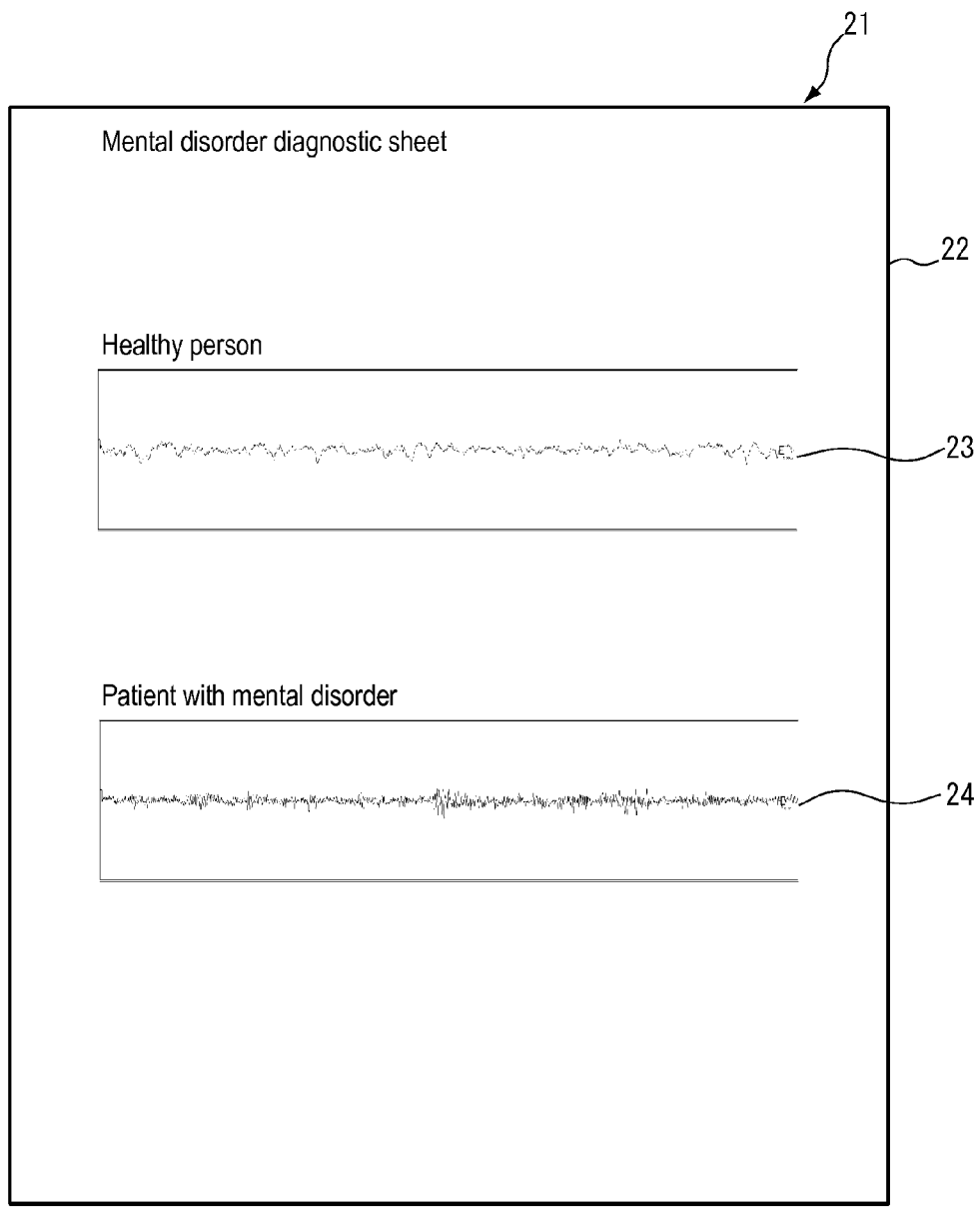
FIG. 30 is a view showing an exemplary mental disorder diagnostic sheet according to this example.

FIG. 30 is a view showing an exemplary sheet showing the healthy electroencephalogram and the disordered electroencephalogram output by the output portion 14 of the electroencephalogram information output apparatus 1000. Such a sheet showing at least the healthy electroencephalogram and the disordered electroencephalogram is a sheet used to diagnose a mental disorder, and, thus, such a sheet is in this example referred to as a mental disorder diagnostic sheet. In a mental disorder diagnostic sheet 21, a healthy electroencephalogram 23 and a disordered electroencephalogram 24 are shown on a sheet 22. The sheet 22 may be made of paper or a resin sheet. There is no limitation on the thickness and the size of the sheet 22. Furthermore, there is no limitation on the color and the like of the sheet 22. The sheet 22 is preferably a transparent sheet, which makes it possible to perform comparison in an overlapping manner with an electroencephalogram during sleep of a test subject. The mental disorder diagnostic sheet 21 shows the healthy electroencephalogram 23 and the disordered electroencephalogram 24, for example, each in the form of a waveform graph with the horizontal axis indicating time and the vertical axis indicating waveform output (e.g., voltage). Furthermore, the healthy electroencephalogram 23 and the disordered electroencephalogram 24 are displayed in juxtaposition in the vertical direction (i.e., in the vertical axis direction).

Figure 31:
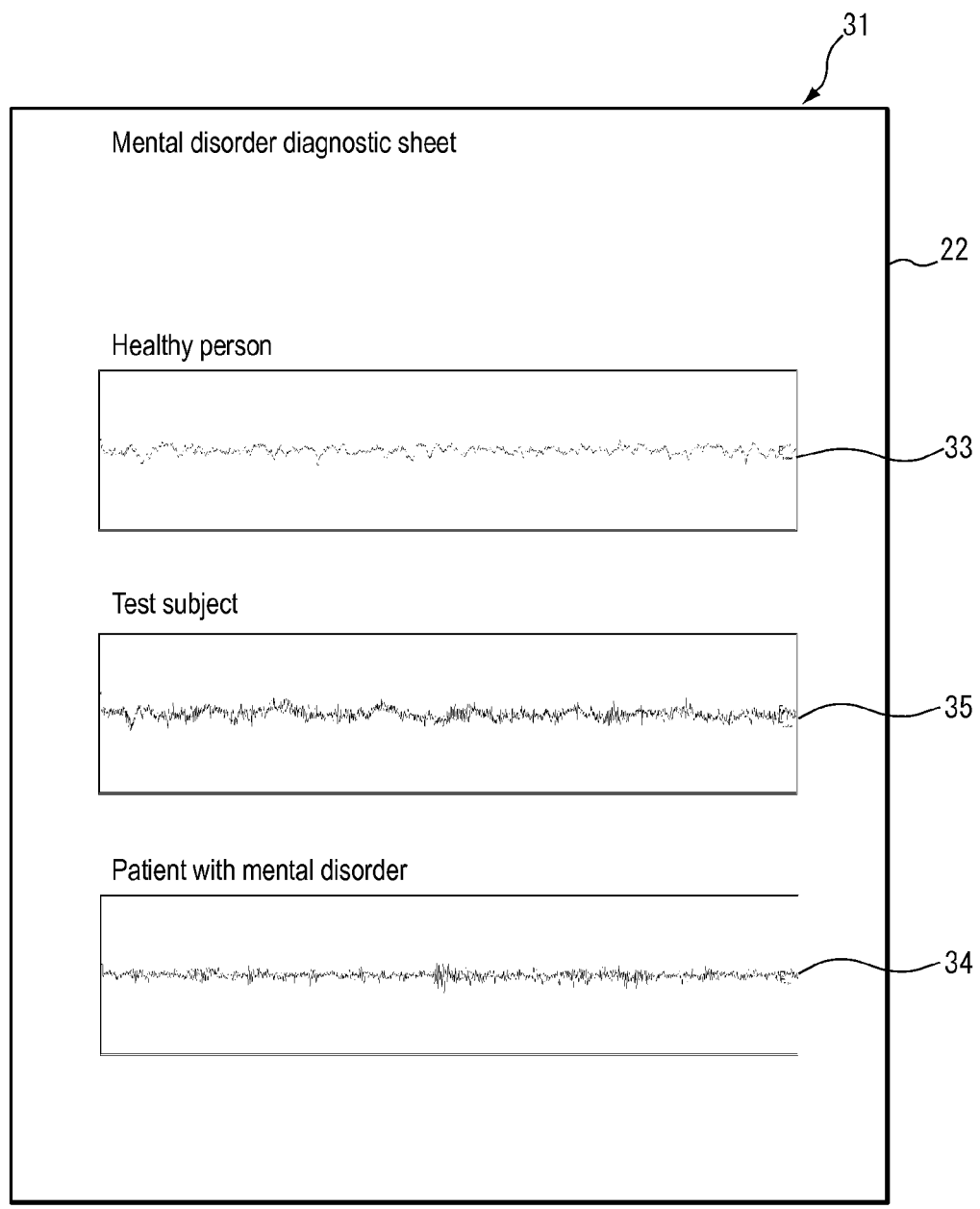
FIG. 31 is a view showing an exemplary mental disorder diagnostic sheet according to this example.

FIG. 31 is a view showing an exemplary mental disorder diagnostic sheet showing the healthy electroencephalogram, the disordered electroencephalogram, and the test subject electroencephalogram output by the output portion 14 of the electroencephalogram information output apparatus 1000. In a mental disorder diagnostic sheet 31, a healthy electroencephalogram 33, a disordered electroencephalogram 34, and a test subject electroencephalogram 35 are shown on the sheet 22 described above. The mental disorder diagnostic sheet 31 shows the healthy electroencephalogram 33, the disordered electroencephalogram 34, and the test subject electroencephalogram 35, for example, each in the form of a waveform graph with the horizontal axis indicating time and the vertical axis indicating waveform output (e.g., voltage). Furthermore, the healthy electroencephalogram 33, the disordered electroencephalogram 34, and the test subject electroencephalogram 35 are displayed in juxtaposition in the vertical direction (i.e., in the vertical axis direction) such that the test subject electroencephalogram 35 is positioned between the healthy electroencephalogram 33 and the disordered electroencephalogram 34.

Next, an operation of the electroencephalogram information output apparatus 1000 will be described with reference to the flowchart in FIG. 32.

(Step S101) The electroencephalogram information output apparatus 1000 determines whether or not an instruction for outputting a healthy electroencephalogram and a disordered electroencephalogram has been accepted. If such an instruction has been accepted, the procedure advances to step S102, and, if not, the procedure advances to step S105.

(Step S102) The output portion 14 reads healthy electroencephalogram information from the healthy electroencephalogram storage portion 11.

(Step S103) The output portion 14 reads disordered electroencephalogram information from the disordered electroencephalogram storage portion 12.

(Step S104) The output portion 14 outputs, in juxtaposition, waveforms respectively indicated by the healthy electroencephalogram information and the disordered electroencephalogram information read in steps S102 and S103. For example, the mental disorder diagnostic sheet 21 is output in which the healthy electroencephalogram and the disordered electroencephalogram are displayed in juxtaposition. Then, the procedure returns to step S101.

(Step S105) The electroencephalogram information output apparatus 1000 determines whether or not an instruction for outputting a healthy electroencephalogram, a disordered electroencephalogram, and a test subject electroencephalogram has been accepted. If such an instruction has been accepted, the procedure advances to step S106, and, if not, the procedure returns to step S101.

(Step S106) The accepting portion 13 determines whether or not test subject electroencephalogram information has been accepted. If such information has been accepted, the procedure advances to step S107, and, if not, the procedure returns to step S106.

(Step S107) The output portion 14 reads healthy electroencephalogram information from the healthy electroencephalogram storage portion 11.

(Step S108) The output portion 14 reads disordered electroencephalogram information from the disordered electroencephalogram storage portion 12.

(Step S109) The output portion 14 outputs, in juxtaposition, a waveform indicated by the test subject electroencephalogram information accepted in step S106 and waveforms respectively indicated by the healthy electroencephalogram information and the disordered electroencephalogram information read in steps S107 and S108. For example, the mental disorder diagnostic sheet 31 is output in which the test subject electroencephalogram is positioned between the healthy electroencephalogram and the disordered electroencephalogram that are displayed in juxtaposition. Then, the procedure returns to step S101.

Figure 32:
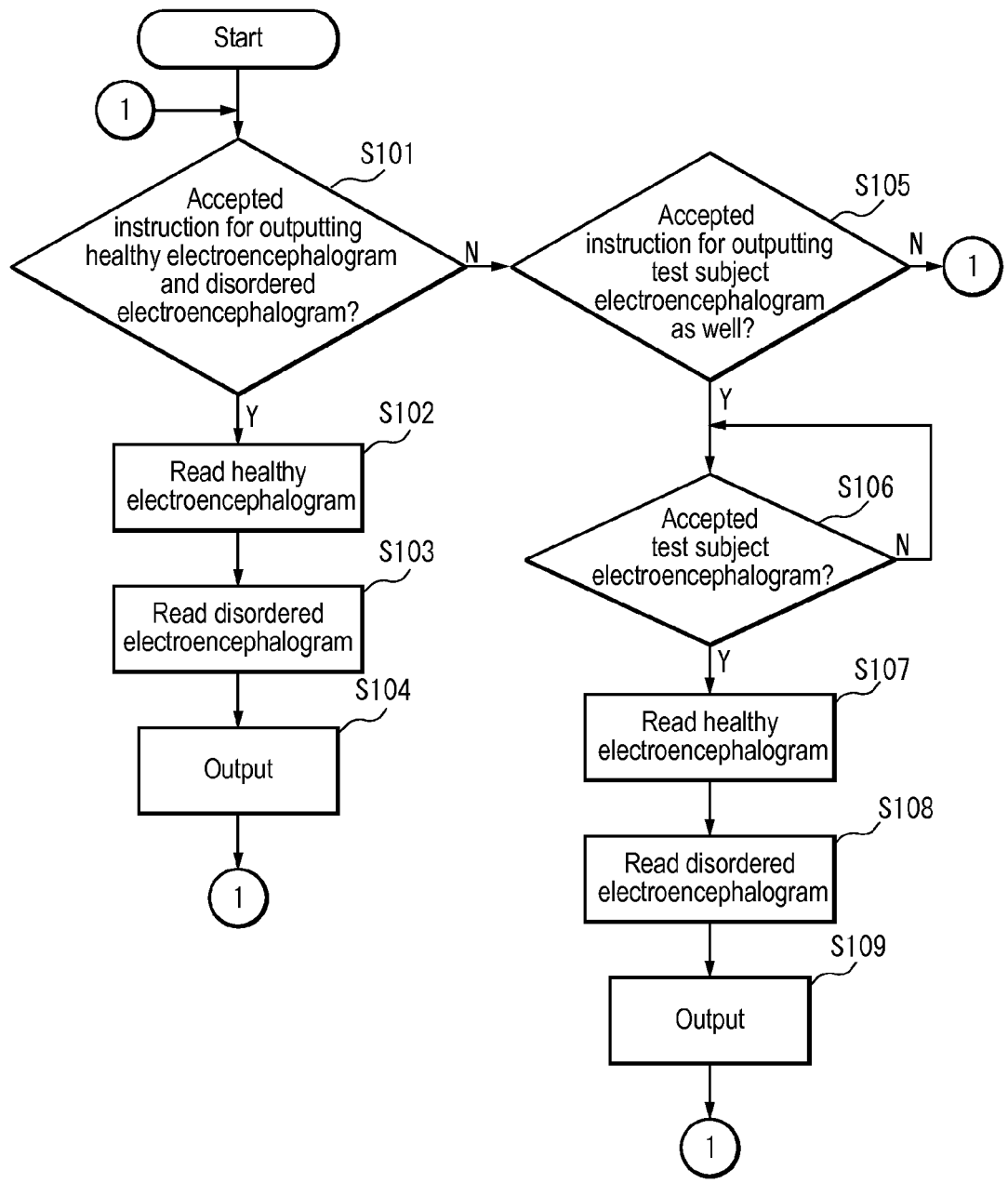
FIG. 32 is a flowchart illustrating an operation of the electroencephalogram information output apparatus according to this example.

Here, the process is terminated by powering off or an interruption to abort the process in the flowchart in FIG. 32.

Hereinafter, a specific operation of the electroencephalogram information output apparatus 1000 in this example will be described.

Figure 33:
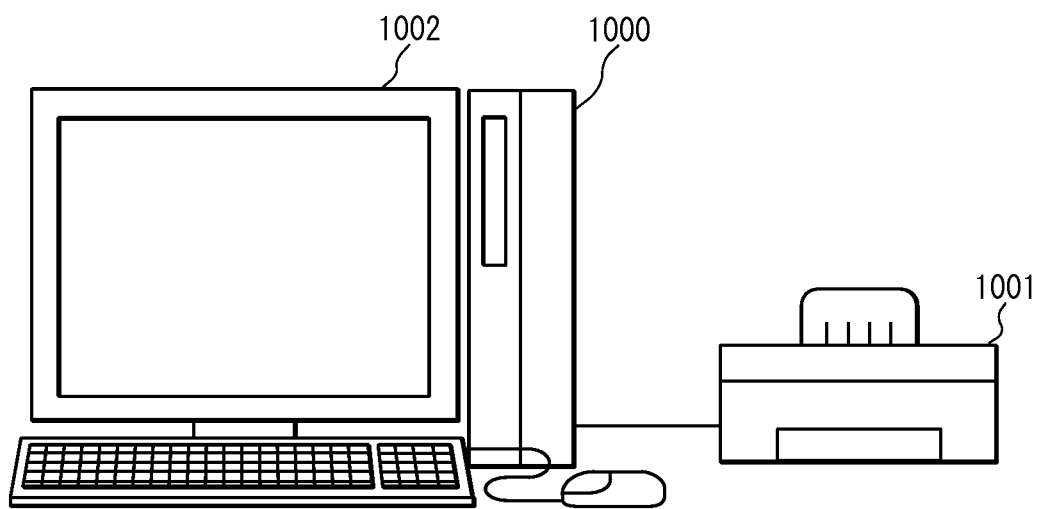
FIG. 33 is a schematic view of the electroencephalogram information output apparatus according to this example.

FIG. 33 is a conceptual view of the electroencephalogram information output apparatus 1000. In the view, the output portion 14 of the electroencephalogram information output apparatus 1000 is connected to a printer 1001 and a monitor 1002, which are output devices.

FIG. 34 is a table showing exemplary healthy electroencephalogram information stored in the healthy electroencephalogram storage portion 11. The healthy electroencephalogram information has items "time" indicating sampling time (sec) and "output" indicating output (μV) of the acquired electroencephalograms. Here, it is assumed that "time" is time elapsed after starting measurement of the electroencephalogram information. Note that it may be time on clock. Here, as an example, a case will be described in which only one piece of healthy electroencephalogram information is stored in the healthy electroencephalogram storage portion 11, but multiple pieces of healthy electroencephalogram information may be stored, and one piece of healthy electroencephalogram information that is to be output may be selected with an instruction from the user.

Furthermore, here, it is assumed that one piece of disordered electroencephalogram information similar to that in FIG. 34 is stored in the disordered electroencephalogram storage portion 12. As in the case of the healthy electroencephalogram storage portion 11, multiple pieces of disordered electroencephalogram information may be stored in the disordered electroencephalogram storage portion 12, and one piece of disordered electroencephalogram information that is to be output may be selected with an instruction from the user.

First, it is assumed that the user operates a keyboard, a mouse, or the like such that an instruction for outputting the healthy electroencephalogram and the disordered electroencephalogram is input via an input menu or the like to an instruction accepting portion (not shown) or the like of the electroencephalogram information output apparatus 1000. Furthermore, it is assumed that information specifying either the printer 1001 or the monitor 1002 as an output destination is also input.

The output portion 14 reads the healthy electroencephalogram information shown in FIG. 34 and the disordered electroencephalogram information similar to that in FIG. 34 respectively from the healthy electroencephalogram storage portion 11 and the disordered electroencephalogram storage portion 12.

Then, the output portion 14 outputs the read information to the output destination specified by the above-described input operation. For example, if the printer 1001 is selected as the output destination, image information of waveforms obtained by plotting the healthy electroencephalogram information and the disordered electroencephalogram information that have been read, that is, image information of the healthy electroencephalogram and image information of the disordered electroencephalogram are respectively generated, and image information in which these pieces of information are arranged in vertical juxtaposition is generated. For example, images of the waveforms are arranged in a template or the like prepared in advance. Then, the generated image information is printed using the printer 1001, for example, on a transparent sheet (e.g., transparent film, etc.).

Accordingly, the mental disorder diagnostic sheet 21 as shown in FIG. 30 is obtained. Note that the sheet 22 of the mental disorder diagnostic sheet 21 obtained here is a transparent sheet.

Since the mental disorder diagnostic sheet 21 is a transparent sheet, the healthy electroencephalogram and the disordered electroencephalogram shown in the mental disorder diagnostic sheet 21 can be compared, in an overlapping manner, with a test subject electroencephalogram output separately from the mental disorder diagnostic sheet 21. Accordingly, this sheet is easy to use in comparison, and makes it possible to perform accurate diagnosis.

Furthermore, if the monitor 1002 is specified as the output destination, an image in which the healthy electroencephalogram and the disordered electroencephalogram are arranged in vertical juxtaposition as in the image in the mental disorder diagnostic sheet 21 shown in FIG. 30 is displayed on the monitor 1002.

Furthermore, it is assumed that the user operates a keyboard, a mouse, or the like such that an instruction for outputting the healthy electroencephalogram, the disordered electroencephalogram, and the test subject electroencephalogram is input via an input menu or the like to an instruction accepting portion (not shown) or the like of the electroencephalogram information output apparatus 1000. Furthermore, it is assumed that information specifying either the printer 1001 or the monitor 1002 as an output destination is also input.

If this instruction is input, information requiring the user to specify test subject electroencephalogram information that is to be output is displayed on the monitor 1002. Then, it is assumed that information (e.g., a file name or a path name of the test subject electroencephalogram information) for specifying test subject electroencephalogram information stored in advance in a storage medium (not shown) or the like of the electroencephalogram information output apparatus 1000 is input by the user to an instruction accepting portion (not shown) or the like. It is assumed that the test subject electroencephalogram information is stored in advance in the storage medium (not shown) or the like of the electroencephalogram information output apparatus 1000. Furthermore, it is assumed that this test subject electroencephalogram information is information similar to the healthy electroencephalogram information shown in FIG. 34.

If the instruction accepting portion (not shown) or the like accepts information specifying test subject electroencephalogram information, the output portion 14 reads the specified test subject electroencephalogram information. Furthermore, as described above, the healthy electroencephalogram information and the disordered electroencephalogram information are respectively read from the healthy electroencephalogram storage portion 11 and the disordered electroencephalogram storage portion 12.

Then, the output portion 14 outputs the read information to the output destination specified by the above-described input operation. For example, if the printer 1001 is selected as the output destination, image information of waveforms obtained by plotting the test subject electroencephalogram information, the healthy electroencephalogram information, and the disordered electroencephalogram information that have been read, that is, image information of the test subject electroencephalogram, image information of the healthy electroencephalogram, and image information of the disordered electroencephalogram are respectively generated, and image information in which these pieces of information are arranged in vertical juxtaposition such that the test subject electroencephalogram is positioned between the healthy electroencephalogram and the disordered electroencephalogram is generated. For example, images of the waveforms are arranged in a template or the like prepared in advance. Then, the generated image information is printed using the printer 1001, in this case, on a transparent sheet (e.g., transparent film, etc.).

Accordingly, the mental disorder diagnostic sheet 31 as shown in FIG. 31 is obtained. The sheet 22 of the mental disorder diagnostic sheet 31 obtained here is a transparent sheet. Furthermore, if the test subject electroencephalogram information has identifying information such as a name of the test subject, this information may be displayed near the image of the test subject electroencephalogram.

The mental disorder diagnostic sheet 31 can be used in a similar manner to the mental disorder diagnostic sheet 21. Moreover, the test subject electroencephalogram, the healthy electroencephalogram, and the disordered electroencephalogram can be compared with each other only with the mental disorder diagnostic sheet 31. Furthermore, since the test subject electroencephalogram information is positioned between the healthy electroencephalogram and the disordered electroencephalogram, the waveforms that are to be compared with each other are located near each other. Furthermore, no other waveform is displayed between these waveforms. Accordingly, the comparison can be very easily performed.

Furthermore, if the monitor 1002 is specified as the output destination, an image in which the test subject electroencephalogram, the healthy electroencephalogram, and the disordered electroencephalogram are arranged in vertical juxtaposition as in the image in the mental disorder diagnostic sheet 31 shown in FIG. 31 is displayed on the monitor 1002.

As described above, according to this example, the healthy electroencephalogram and the disordered electroencephalogram can be output in juxtaposition. Thus, for example, a doctor who visually compares the waveforms indicated by this output result with the waveform indicated by the test subject electroencephalogram information can more accurately and more easily determine whether or not the waveform indicated by the test subject electroencephalogram information is that of a patient with a mental disorder.

Furthermore, the healthy electroencephalogram, the disordered electroencephalogram, and the test subject electroencephalogram can be output in juxtaposition. Thus, for example, a doctor who visually compares the test subject electroencephalogram with the other electroencephalogram waveforms indicated by the output result can more accurately and more easily determine whether or not the waveform indicated by the test subject electroencephalogram information is that of a patient with a mental disorder.

In particular, since the test subject electroencephalogram is positioned between the healthy electroencephalogram and the disordered electroencephalogram, and these waveforms are arranged in vertical juxtaposition, the test subject electroencephalogram is located near each of the healthy electroencephalogram and the disordered electroencephalogram. Thus, the test subject electroencephalogram can be more easily compared with the healthy electroencephalogram and the disordered electroencephalogram.

Furthermore, in particular, since these waveforms are printed on a transparent sheet, the healthy electroencephalogram and the disordered electroencephalogram printed on this sheet can be overlapped with the test subject electroencephalogram, and, in this state, it can be determined which of the waveforms is closer to the test subject electroencephalogram. Accordingly, the presence or absence of a mental disorder can be easily determined.

In the foregoing examples, the exemplary status was described in which electroencephalogram information obtained by multiplying, by ⅕, a value of the electroencephalogram information acquired by the electroencephalogram acquiring apparatus (i.e., by multiplying an amplitude by ⅕) is used by the mental disorder analysis apparatus, and an average value of eight values obtained by the appearance status acquiring unit dividing one epoch in 30 seconds into eight portions each in 4 seconds and performing Fourier transform on each of these portions is used as a result obtained by performing Fourier transform on that one epoch. The values such as the threshold values shown in the foregoing examples are values set according to this sort of case. Setting the sensitivity of the electroencephalogram information smaller, and setting the time duration for Fourier transform shorter are proper in order to perform the analysis at high quality, for example, in the case where a noise level of the electroencephalogram acquiring apparatus such as an electroencephalograph is high (e.g., approximately 10 μV).

However, in the case where a high-performance electroencephalogram acquiring apparatus with a noise level of approximately 3 μV or less is used, in the present invention, the sensitivity of the electroencephalogram information does not have to be set small, and the electroencephalogram information acquired by the electroencephalogram acquiring apparatus may be used as it is. Furthermore, instead of performing Fourier transform on each of multiple time segments obtained by dividing an epoch and acquiring an average value of the resulting values, it is possible to use the result obtained by performing Fourier transform once on an entire epoch, as it is, as a result obtained by performing Fourier transform on the epoch. Accordingly, the analysis can be performed at higher quality.

Note that, in the case where the electroencephalogram information acquired by the electroencephalogram acquiring apparatus is used as it is, and the result obtained by the appearance status acquiring unit performing Fourier transform on an entire epoch is used as a result obtained by performing Fourier transform on that epoch, the values acquired by the appearance status acquiring unit performing Fourier transform, and the values such as the threshold values used to diagnose a mental disorder or the like, described in the foregoing examples, have to be changed as appropriate. Specifically, an output value of the electroencephalogram information becomes a value five times the above-mentioned value because it is changed from 1/5 to 1, and the time duration for Fourier transform becomes 7.5 times the above-mentioned duration because it is changed from 4 seconds, which is a time duration obtained by dividing an epoch, to 30 seconds, which is a time duration of an entire epoch. Thus, power values of $\alpha$ waves, $\beta$ waves, $\delta$ waves, and the like obtained by Fourier transform, and the threshold values and the like related thereto respectively become $5^2 \times 7.5$ (=187.5) times the values shown in the foregoing examples.

Specifically, the values acquired by the appearance status acquiring unit performing Fourier transform and the values such as the threshold values used to diagnose a mental disorder or the like are changed as below.

In the description of the Example above, the threshold value for the power of $\alpha$ waves used by the determining unit 1022 when determining whether or not the test subject has depression becomes, for example, 187.5 to 281.25 $\mu V^2$, and the threshold value when detecting serious depression becomes, for example, 375 $\mu V^2$. Furthermore, the $\alpha$ wave peak value acquired by the appearance status acquiring unit 1021 performing fast Fourier transform in the example given in the Example above is changed from 1.5 $\mu V^2$ to 281.25 $\mu V^2$.

Furthermore, the values of "$\alpha$ power" in the $\alpha$ power management table shown in FIG. 13 are all changed to values that are 187.5 times the original values. Furthermore, the value calculated by the determining unit 1022 as an average value of the values of "$\alpha$ power" is changed to "271.875 $\mu V^2$". Furthermore, the value shown as the threshold value for the power of $\alpha$ waves in the example given in the Example is changed from "1.0 $\mu V^2$" to "187.5 $\mu V^2$".

Furthermore, in the example given in the Another Example, the power value of $\delta$ waves in a REM sleep period is changed from about 1 $\mu V^2$/min to about 187.5 $\mu V^2$/min, and the power value in a non-REM sleep period is changed from about 7 to 10 $\mu V^2$/min to about 1312.5 to 1875 $\mu V^2$/min.

Furthermore, in the example given in the Another Example, the average value of integral values of $\delta$ waves respectively contained in the multiple epochs, used to determine that the test subject does not have depression, is changed from 1.5 $\mu V^2$ or more to 281.25 $\mu V^2$.

Furthermore, in the example given in the Another Example, the threshold value for the power of $\delta$ waves, used when determining the number of times of appearance of $\delta$ waves in order to determine that depression is not present, is changed from "5 $\mu V^2$" to "937.5 $\mu V^2$", and the threshold value for the average value of the powers of $\delta$ waves is changed from "1.0 $\mu V^2$" to "187.5 $\mu V^2$".

Furthermore, in the Another Example, the threshold value used by the determining unit 2022 when determining whether or not the average value of the powers of $\delta$ waves acquired in the respective epochs by the appearance status acquiring unit 2021 is the threshold value or more is changed from "1.0 $\mu V^2$" to "187.5 $\mu V^2$".

Furthermore, the threshold value for the power of $\beta$ waves shown in the foregoing example is changed to 56.25 $\mu V^2$.

Furthermore, the power values in the graphs shown in FIGS. 5, 6, 13, 14, 18, and 19 are all changed to values that are 187.5 times the original values.

Furthermore, the values of "output" in the healthy electroencephalogram information shown in FIG. 34 are all changed to values that are five times the original values.

In the foregoing examples, if one epoch is set at 4 seconds, for example, the values acquired by the appearance status acquiring unit performing Fourier transform, and the values such as the threshold values used to diagnose a mental disorder or the like, described in the foregoing examples, can be used as they are.

In the foregoing examples, each process (each function) may be realized as integrated processing using a single apparatus (system), or may be realized as distributed processing using multiple apparatuses.

Furthermore, in the foregoing examples, the case was described in which the mental disorder analysis apparatus is a stand-alone apparatus, but the mental disorder analysis apparatus may be either a stand-alone apparatus or a server apparatus in a server-client system. In the latter case, the output portion and the accepting portion use a communication line to accept input or output a screen.

In the foregoing examples, software for realizing the mental disorder analysis apparatus is a program as below. That is to say, this program is a program for causing a computer that can access a storage portion in which sleep electroencephalogram information, which is information on electroencephalograms during sleep of a test subject, is stored to function as: an analyzing portion that performs analysis regarding presence or absence of a mental disorder using the sleep electroencephalogram information stored in the storage portion; and an output portion that outputs a result of the analysis performed by the analyzing portion.

Furthermore, this program is a program for causing a computer that can access a healthy electroencephalogram storage portion in which healthy electroencephalogram information, which is information on electroencephalograms during sleep of a healthy person, is stored and a disordered electroencephalogram storage portion in which disordered electroencephalogram information, which is information on electroencephalograms during sleep of a patient with a mental disorder, is stored to function as: an output portion that outputs a waveform indicated by the healthy electroencephalogram information and a waveform indicated by the disordered electroencephalogram information in juxtaposition.

Note that, in the programs, the functions realized by the programs do not include functions that can be realized only by hardware. For example, functions that can be realized only by hardware, such as a modem or an interface card, in an acquiring portion that acquires information or an output portion that outputs information are not included in the functions realized by the above-described programs.

Furthermore, a computer that executes the programs may be a single computer or may be multiple computers. That is to say, integrated processing may be performed, or distributed processing may be performed.

Figure 27:
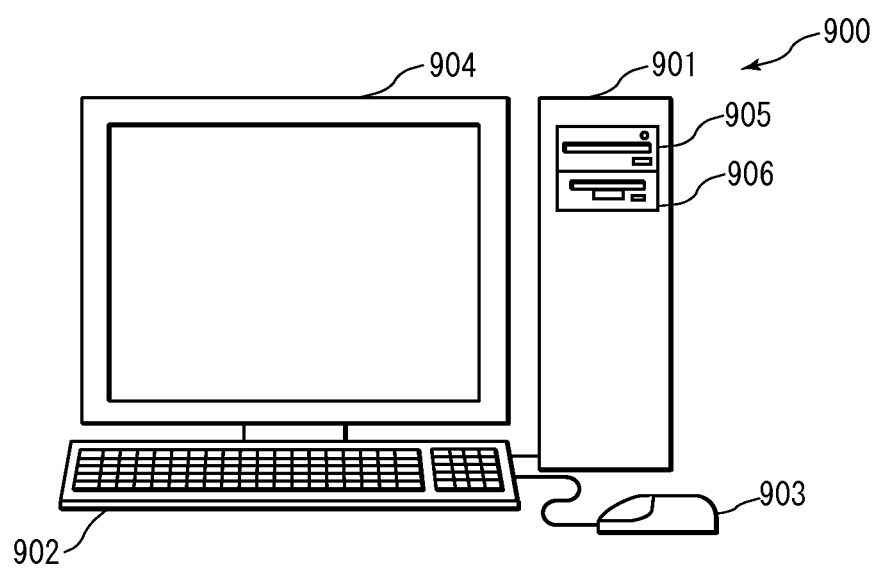
FIG. 27 is a view showing an exemplary appearance of a computer system according to the examples of the present invention.

FIG. 27 is a schematic view showing an exemplary appearance of a computer that executes the programs described above to realize the mental disorder analysis apparatus in the foregoing examples. The foregoing examples may be realized using computer hardware and computer programs executed thereon.

In FIG. 27, a computer system 900 is provided with a computer 901 including a CD-ROM (compact disk read only memory) drive 905 and an FD (Floppy (registered trademark) disk) drive 906, a keyboard 902, a mouse 903, and a monitor 904.

Figure 28:
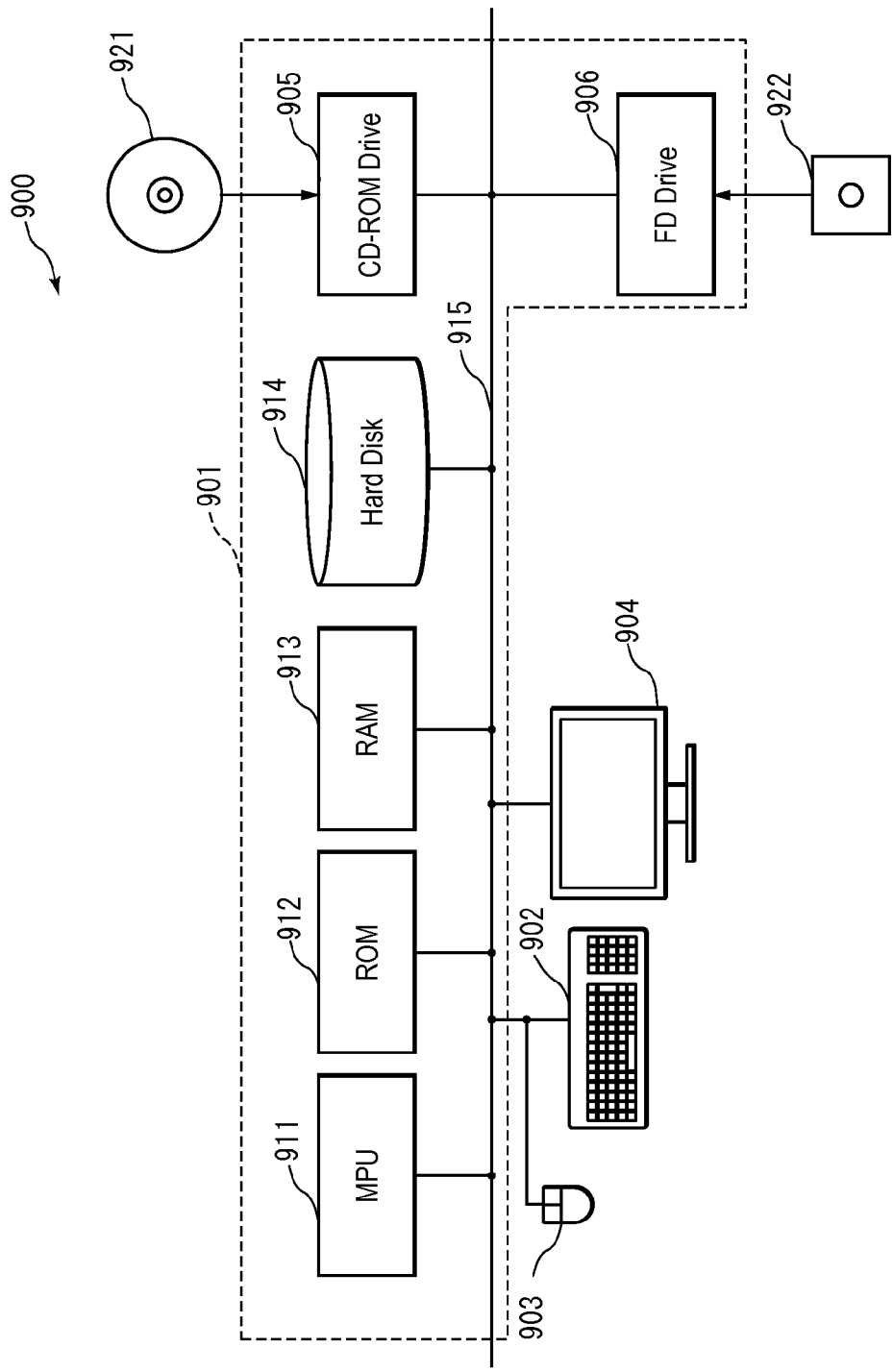
FIG. 28 is a diagram showing an exemplary configuration of the computer system according to the examples.

FIG. 28 is a diagram showing an internal configuration of the computer system 900. In FIG. 28, the computer 901 is provided with, not only the CD-ROM drive 905 and the FD drive 906, but also an MPU (micro processing unit) 911, a ROM 912 in which a program such as a startup program is to be stored, a RAM (random access memory) 913 that is connected to the MPU 911 and in which a command of an application program is temporarily stored, and a temporary storage area is provided, a hard disk 914 in which an application program, a system program, and data are stored, and a bus 915 that connects the MPU 911, the ROM 912, and the like. Note that the computer 901 may include a network card (not shown) for providing a connection to a LAN.

The program for causing the computer system 900 to execute the functions of the mental disorder analysis apparatuses and the like in the foregoing examples may be stored in a CD-ROM 921 or a FD 922 that is inserted into the CD-ROM drive 905 or the FD drive 906, and be transmitted to the hard disk 914. Alternatively, the program may be transmitted via a network (not shown) to the computer 901 and stored in the hard disk 914. At the time of execution, the program is loaded into the RAM 913. The program may be loaded from the CD-ROM 921 or the FD 922, or directly from a network.

The program does not necessarily have to include, for example, an operating system (OS) or a third party program to cause the computer 901 to execute the functions of the mental disorder analysis apparatus in the foregoing examples. The program may only include a command portion to call an appropriate function (module) in a controlled mode and obtain desired results. The manner in which the computer system 900 operates is well known, and, thus, a detailed description thereof has been omitted.

The present invention is not limited to the examples set forth herein. Various modifications are possible within the scope of the present invention.

As described above, the mental disorder analysis apparatus according to the present invention is suitable as an apparatus for analyzing information on electroencephalograms, and is particularly useful as an apparatuses and the like for diagnosing a mental disorder using the information on electroencephalograms.

The invention claimed is:

1. A mental disorder analysis apparatus, comprising:
a storage unit that stores sleep electroencephalogram information that is information on electroencephalograms during sleep of a test subject;
an analyzing unit that performs analysis regarding presence or absence of a mental disorder using the sleep electroencephalogram information stored in the storage unit; and
an output unit that outputs a result of the analysis performed by the analyzing unit,
wherein, as the analysis, the analyzing unit acquires information indicating an appearance status of any of $\alpha$ waves, $\delta$ waves and $\beta$ waves contained in the sleep electroencephalogram information, and determines the presence or absence of a mental disorder according to the information,
wherein the output unit outputs a result of determination regarding the presence or absence of a mental disorder performed by the analyzing unit,
wherein the analyzing unit acquires information indicating either one of an appearance rate and a power of $\alpha$ waves contained in sleep electroencephalogram information in a non-REM sleep period, in the sleep electroencephalogram information, and determines the presence or absence of a mental disorder according to the information, and
wherein the analyzing unit detects spindle waves in an $\alpha$ band in sleep electroencephalogram information in a non-REM sleep period, in the sleep electroencephalogram information, and determines that depression is present in a case where an appearance rate of the detected spindle waves exceeds a predetermined threshold value.

2. A mental disorder analysis apparatus, comprising:
a storage unit that stores sleep electroencephalogram information that is information on electroencephalograms during sleep of a test subject;
an analyzing unit that performs analysis regarding presence or absence of a mental disorder using the sleep electroencephalogram information stored in the storage unit; and
an output unit that outputs a result of the analysis performed by the analyzing unit,
wherein, as the analysis, the analyzing unit acquires information indicating an appearance status of any of $\alpha$ waves, $\delta$ waves and $\beta$ waves contained in the sleep electroencephalogram information, and determines the presence or absence of a mental disorder according to the information,
wherein the output unit outputs a result of determination regarding the presence or absence of a mental disorder performed by the analyzing unit,
wherein the analyzing unit acquires information indicating either one of an appearance rate and a power of $\alpha$ waves contained in sleep electroencephalogram information in a non-REM sleep period, in the sleep electroencephalogram information, and determines the presence or absence of a mental disorder according to the information, and
wherein the analyzing unit performs Fourier transform to detect an $\alpha$ wave component in each of multiple periods forming a non-REM sleep period in the sleep electroencephalogram information, and determines that depression is present in a case where an appearance rate of periods in which the $\alpha$ wave component is detected exceeds a predetermined threshold value.

3. A mental disorder analysis apparatus, comprising:
a storage unit that stores sleep electroencephalogram information that is information on electroencephalograms during sleep of a test subject;
an analyzing unit that performs analysis regarding presence or absence of a mental disorder using the sleep electroencephalogram information stored in the storage unit; and
an output unit that outputs a result of the analysis performed by the analyzing unit,
wherein, as the analysis, the analyzing unit acquires information indicating an appearance status of any of $\alpha$ waves, $\delta$ waves and $\beta$ waves contained in the sleep electroencephalogram information, and determines the presence or absence of a mental disorder according to the information, wherein the output unit outputs a result of determination regarding the presence or absence of a mental disorder performed by the analyzing unit, wherein the analyzing unit acquires information indicating either one of an appearance rate and a power of δ waves contained in sleep electroencephalogram information in a non-REM sleep period, in the sleep electroencephalogram information, and determines the presence or absence of a mental disorder according to the information, and wherein the analyzing unit performs Fourier transform to detect a δ wave component in each of multiple periods forming a non-REM sleep period in the sleep electroencephalogram information, and determines that depression is not present in a case where an appearance rate of periods in which the δ wave component is detected exceeds a predetermined threshold value.

4. A mental disorder analysis apparatus, comprising:

a storage unit that stores sleep electroencephalogram information that is information on electroencephalograms during sleep of a test subject;

an analyzing unit that performs analysis regarding presence or absence of a mental disorder using the sleep electroencephalogram information stored in the storage unit, and an output unit that outputs a result of the analysis performed by the analyzing unit, wherein, as the analysis, the analyzing unit acquires information indicating an appearance status of any of α waves, δ waves and β waves contained in the sleep electroencephalogram information, and determines the presence or absence of a mental disorder according to the information, wherein the output unit outputs a result of determination regarding the presence or absence of a mental disorder performed by the analyzing unit, wherein the analyzing unit acquires information indicating either one of an appearance rate and a power of δ waves contained in sleep electroencephalogram information in a non-REM sleep period, in the sleep electroencephalogram information, and determines the presence or absence of a mental disorder according to the information, and wherein the analyzing unit performs Fourier transform to detect a δ wave component in each of at least one period forming a non-REM sleep period in the sleep electroencephalogram information, and determines that depression is not present in a case where any detected δ wave component has a power exceeding a predetermined threshold value.

5. A mental disorder analysis apparatus, comprising:

a storage unit that stores sleep electroencephalogram information that is information on electroencephalograms during sleep of a test subject;

an analyzing unit that performs analysis regarding presence or absence of a mental disorder using the sleep electroencephalogram information stored in the storage unit; and an output unit that outputs a result of the analysis performed by the analyzing unit, wherein, as the analysis, the analyzing unit acquires information indicating an appearance status of any of α waves, δ waves and β waves contained in the sleep electroencephalogram information, and determines the presence or absence of a mental disorder according to the information, wherein the output unit outputs a result of determination regarding the presence or absence of a mental disorder performed by the analyzing unit, wherein the analyzing unit acquires information indicating either one of an appearance rate and a change in a waveform size of β waves contained in sleep electroencephalogram information in a REM sleep period, in the sleep electroencephalogram information, and determines the presence or absence of a mental disorder according to the information, and wherein the analyzing unit performs Fourier transform to detect a β wave component in each of multiple periods forming a REM sleep period in the sleep electroencephalogram information, and determines that depression is present in a case where an appearance rate of periods in which the β wave component is detected exceeds a predetermined threshold value.

6. A mental disorder analysis apparatus, comprising:

a storage unit that stores sleep electroencephalogram information that is information on electroencephalograms during sleep of a test subject;

an analyzing unit that performs analysis regarding presence or absence of a mental disorder using the sleep electroencephalogram information stored in the storage unit; and an output unit that outputs a result of the analysis performed by the analyzing unit, wherein, as the analysis, the analyzing unit acquires information indicating an appearance status of any of α waves, δ waves and β waves contained in the sleep electroencephalogram information, and determines the presence or absence of a mental disorder according to the information, wherein the output unit outputs a result of determination regarding the presence or absence of a mental disorder performed by the analyzing unit, wherein the analyzing unit acquires information indicating either one of an appearance rate and a change in a waveform size of β waves contained in sleep electroencephalogram information in a REM sleep period, in the sleep electroencephalogram information, and determines the presence or absence of a mental disorder according to the information, and wherein the analyzing unit acquires a difference between amplitudes of adjacent waves in β waves in each of at least one period forming a REM sleep period in the sleep electroencephalogram information, and determines that depression is present in a case where any acquired difference between the amplitudes exceeds a predetermined threshold value.

7. A mental disorder analysis apparatus, comprising:

a storage unit that stores sleep electroencephalogram information that is information on electroencephalograms during sleep of a test subject;

an analyzing unit that performs analysis regarding presence or absence of a mental disorder using the sleep electroencephalogram information stored in the storage unit; and an output unit that outputs a result of the analysis performed by the analyzing unit, wherein, as the analysis, the analyzing unit acquires information indicating an appearance status of any of α waves, δ waves and β waves contained in the sleep electroencephalogram information, and determines the presence or absence of a mental disorder according to the information, wherein the output unit outputs a result of determination regarding the presence or absence of a mental disorder performed by the analyzing unit, wherein the mental disorder analysis apparatus further comprises a medication determining unit that acquires information indicating an appearance status of γ waves contained in the sleep electroencephalogram information stored in the storage unit, and determines whether or not drug administration has been performed for a mental disorder according to the information, and wherein the output unit further outputs a result of determination performed by the medication determining unit.

8. A mental disorder analysis method performed using a storage unit that stores sleep electroencephalogram information that is information on electroencephalograms during sleep of a test subject, an analyzing unit, and an output unit, the method comprising:

an analyzing step of the analyzing unit performing analysis regarding presence or absence of a mental disorder using the sleep electroencephalogram information stored in the storage unit; and an output step of the output unit outputting a result of the analysis performed in the analyzing step;

wherein, in the analyzing step, as the analysis, information indicating an appearance status of any of α waves, δ waves and β waves contained in the sleep electroencephalogram information is acquired, and the presence or absence of a mental disorder is determined according to the information, wherein, in the output step, a result of determination regarding the presence or absence of a mental disorder performed in the analyzing step is output, wherein, in the analyzing step, information indicating either one of an appearance rate and a power of α waves contained in sleep electroencephalogram information in a non-REM sleep period, in the sleep electroencephalogram information, is acquired, and the presence or absence of a mental disorder according to the information is determined, and wherein, in the analyzing step, spindle waves in an α band in sleep electroencephalogram information in a non-REM sleep period, in the sleep electroencephalogram information, is detected, and depression being present is determined in a case where an appearance rate of the detected spindle waves exceeds a predetermined threshold value.

9. A mental disorder analysis method performed using a storage unit that stores sleep electroencephalogram information that is information on electroencephalograms during sleep of a test subject, an analyzing unit, and an output unit, the method comprising:

an analyzing step of the analyzing unit performing analysis regarding presence or absence of a mental disorder using the sleep electroencephalogram information stored in the storage unit; and an output step of the output unit outputting a result of the analysis performed in the analyzing step;

wherein, in the analyzing step, as the analysis, information indicating an appearance status of any of α waves, δ waves and β waves contained in the sleep electroencephalogram information is acquired, and the presence or absence of a mental disorder is determined according to the information, wherein, in the output step, a result of determination regarding the presence or absence of a mental disorder performed in the analyzing step is output, wherein, in the analyzing step, information indicating either one of an appearance rate and a power of α waves contained in sleep electroencephalogram information in a non-REM sleep period, in the sleep electroencephalogram information, is acquired, and the presence or absence of a mental disorder according to the information is determined, and wherein, in the analyzing step, Fourier transform is performed to detect an α wave component in each of multiple periods forming a non-REM sleep period in the sleep electroencephalogram information, and depression being present is determined in a case where an appearance rate of periods in which the α wave component is detected exceeds a predetermined threshold value.

10. A mental disorder analysis method performed using a storage unit that stores sleep electroencephalogram information that is information on electroencephalograms during sleep of a test subject, an analyzing unit, and an output unit, the method comprising:

an analyzing step of the analyzing unit performing analysis regarding presence or absence of a mental disorder using the sleep electroencephalogram information stored in the storage unit; and an output step of the output unit outputting a result of the analysis performed in the analyzing step;

wherein, in the analyzing step, as the analysis, information indicating an appearance status of any of α waves, δ waves and β waves contained in the sleep electroencephalogram information is acquired, and the presence or absence of a mental disorder is determined according to the information, wherein, in the output step, a result of determination regarding the presence or absence of a mental disorder performed in the analyzing step is output, wherein, in the analyzing step, information indicating either one of an appearance rate and a power of δ waves contained in sleep electroencephalogram information in a non-REM sleep period, in the sleep electroencephalogram information, is acquired, and the presence or absence of a mental disorder according to the information is determined, and wherein, in the analyzing step, Fourier transform is performed to detect a δ wave component in each of multiple periods forming a non-REM sleep period in the sleep electroencephalogram information, and depression being not present is determined in a case where an appearance rate of periods in which the δ wave component is detected exceeds a predetermined threshold value.

11. A mental disorder analysis method performed using a storage unit that stores sleep electroencephalogram information that is information on electroencephalograms during sleep of a test subject, an analyzing unit, and an output unit, the method comprising:

an analyzing step of the analyzing unit performing analysis regarding presence or absence of a mental disorder using the sleep electroencephalogram information stored in the storage unit; and an output step of the output unit outputting a result of the analysis performed in the analyzing step;

wherein, in the analyzing step, as the analysis, information indicating an appearance status of any of α waves, δ waves and β waves contained in the sleep electroencephalogram information is acquired, and the presence or absence of a mental disorder is determined according to the information, wherein, in the output step, a result of determination regarding the presence or absence of a mental disorder performed in the analyzing step is output, wherein, in the analyzing step, information indicating either one of an appearance rate and a power of δ waves contained in sleep electroencephalogram information in a non-REM sleep period, in the sleep electroencephalogram information, is acquired, and the presence or absence of a mental disorder according to the information is determined, and wherein, in the analyzing step, Fourier transform is performed to detect a δ wave component in each of at least one period forming a non-REM sleep period in the sleep electroencephalogram information, and depression being not present is determined in a case where any detected δ wave component has a power exceeding a predetermined threshold value.

12. A mental disorder analysis method performed using a storage unit that stores sleep electroencephalogram information that is information on electroencephalograms during sleep of a test subject, an analyzing unit, and an output unit, the method comprising:

an analyzing step of the analyzing unit performing analysis regarding presence or absence of a mental disorder using the sleep electroencephalogram information stored in the storage unit; and an output step of the output unit outputting a result of the analysis performed in the analyzing step;

wherein, in the analyzing step, as the analysis, information indicating an appearance status of any of α waves, δ waves and β waves contained in the sleep electroencephalogram information is acquired, and the presence or absence of a mental disorder is determined according to the information, wherein, in the output step, a result of determination regarding the presence or absence of a mental disorder performed in the analyzing step is output, wherein, in the analyzing step, information indicating either one of an appearance rate and a change in a waveform size of β waves contained in sleep electroencephalogram information in a REM sleep period, in the sleep electroencephalogram information, is acquired, and the presence or absence of a mental disorder according to the information is determined, and wherein, in the analyzing step, Fourier transform is performed to detect a β wave component in each of multiple periods forming a REM sleep period in the sleep electroencephalogram information, and depression being present is determined in a case where an appearance rate of periods in which the β wave component is detected exceeds a predetermined threshold value.

13. A mental disorder analysis method performed using a storage unit that stores sleep electroencephalogram information that is information on electroencephalograms during sleep of a test subject, an analyzing unit, and an output unit, the method comprising:

an analyzing step of the analyzing unit performing analysis regarding presence or absence of a mental disorder using the sleep electroencephalogram information stored in the storage unit; and an output step of the output unit outputting a result of the analysis performed in the analyzing step;

wherein, in the analyzing step, as the analysis, information indicating an appearance status of any of α waves, δ waves and β waves contained in the sleep electroencephalogram information is acquired, and the presence or absence of a mental disorder is determined according to the information, wherein, in the output step, a result of determination regarding the presence or absence of a mental disorder performed in the analyzing step is output, wherein, in the analyzing step, information indicating either one of an appearance rate and a change in a waveform size of β waves contained in sleep electroencephalogram information in a REM sleep period, in the sleep electroencephalogram information, is acquired, and the presence or absence of a mental disorder according to the information is determined, and wherein, in the analyzing step, a difference between amplitudes of adjacent waves in β waves in each of at least one period forming a REM sleep period in the sleep electroencephalogram information is acquired, and depression being present is determined in a case where any acquired difference between the amplitudes exceeds a predetermined threshold value.

14. A mental disorder analysis method performed using a storage unit that stores sleep electroencephalogram information that is information on electroencephalograms during sleep of a test subject, an analyzing unit, and an output unit, the method comprising:

an analyzing step of the analyzing unit performing analysis regarding presence or absence of a mental disorder using the sleep electroencephalogram information stored in the storage unit; and an output step of the output unit outputting a result of the analysis performed in the analyzing step;

wherein, in the analyzing step, as the analysis, information indicating an appearance status of any of α waves, δ waves and β waves contained in the sleep electroencephalogram information is acquired, and the presence or absence of a mental disorder is determined according to the information, wherein, in the output step, a result of determination regarding the presence or absence of a mental disorder performed in the analyzing step is output, wherein the mental disorder analysis method further comprises a medication determining step of a medication determining unit acquiring information indicating an appearance status of γ waves contained in the sleep electroencephalogram information stored in the storage unit, determining whether or not drug administration has been performed for a mental disorder according to the information, and outputting a result of determination performed by the medication determining step.

15. A non-transitory computer-readable medium containing a computer program stored therein for causing a computer, which accesses a storage portion that stores sleep electroencephalogram information that is information on electroencephalograms during sleep of a test subject, to function as:

an analyzing portion that performs analysis regarding presence or absence of a mental disorder using the sleep electroencephalogram information stored in the storage portion; and an output portion that outputs a result of the analysis performed by the analyzing portion, wherein, as the analysis, the analyzing portion acquires information indicating an appearance status of any of α waves, δ waves and β waves contained in the sleep electroencephalogram information, and determines the presence or absence of a mental disorder according to the information, wherein the output portion outputs a result of determination regarding the presence or absence of a mental disorder performed by the analyzing portion, wherein the analyzing portion acquires information indicating either one of an appearance rate and a power of α waves contained in sleep electroencephalogram information in a non-REM sleep period, in the sleep electroencephalogram information, and determines the presence or absence of a mental disorder according to the information, and wherein the analyzing portion detects spindle waves in an α band in sleep electroencephalogram information in a non-REM sleep period, in the sleep electroencephalogram information, and determines that depression is present in a case where an appearance rate of the detected spindle waves exceeds a predetermined threshold value.

16. A non-transitory computer-readable medium containing a computer program stored therein for causing a computer, which accesses a storage portion that stores sleep electroencephalogram information that is information on electroencephalograms during sleep of a test subject, to function as:

an analyzing portion that performs analysis regarding presence or absence of a mental disorder using the sleep electroencephalogram information stored in the storage portion; and an output portion that outputs a result of the analysis performed by the analyzing portion, wherein, as the analysis, the analyzing portion acquires information indicating an appearance status of any of α waves, δ waves and β waves contained in the sleep electroencephalogram information, and determines the presence or absence of a mental disorder according to the information, wherein the output portion outputs a result of determination regarding the presence or absence of a mental disorder performed by the analyzing portion, wherein the analyzing portion acquires information indicating either one of an appearance rate and a power of α waves contained in sleep electroencephalogram information in a non-REM sleep period, in the sleep electroencephalogram information, and determines the presence or absence of a mental disorder according to the information, and wherein the analyzing portion performs Fourier transform to detect an α wave component in each of multiple periods forming a non-REM sleep period in the sleep electroencephalogram information, and determines that depression is present in a case where an appearance rate of periods in which the α wave component is detected exceeds a predetermined threshold value.

17. A non-transitory computer-readable medium containing a computer program stored therein for causing a computer, which accesses a storage portion that stores sleep electroencephalogram information that is information on electroencephalograms during sleep of a test subject, to function as:

an analyzing portion that performs analysis regarding presence or absence of a mental disorder using the sleep electroencephalogram information stored in the storage portion; and an output portion that outputs a result of the analysis performed by the analyzing portion, wherein, as the analysis, the analyzing portion acquires information indicating an appearance status of any of α waves, δ waves and β waves contained in the sleep electroencephalogram information, and determines the presence or absence of a mental disorder according to the information, wherein the output portion outputs a result of determination regarding the presence or absence of a mental disorder performed by the analyzing portion, wherein the analyzing portion acquires information indicating either one of an appearance rate and a power of δ waves contained in sleep electroencephalogram information in a non-REM sleep period, in the sleep electroencephalogram information, and determines the presence or absence of a mental disorder according to the information, and wherein the analyzing portion performs Fourier transform to detect a δ wave component in each of multiple periods forming a non-REM sleep period in the sleep electroencephalogram information, and determines that depression is not present in a case where an appearance rate of periods in which the δ wave component is detected exceeds a predetermined threshold value.

18. A non-transitory computer-readable medium containing a computer program stored therein for causing a computer, which accesses a storage portion that stores sleep electroencephalogram information that is information on electroencephalograms during sleep of a test subject, to function as:

an analyzing portion that performs analysis regarding presence or absence of a mental disorder using the sleep electroencephalogram information stored in the storage portion; and an output portion that outputs a result of the analysis performed by the analyzing portion, wherein, as the analysis, the analyzing portion acquires information indicating an appearance status of any of α waves, δ waves and β waves contained in the sleep electroencephalogram information, and determines the presence or absence of a mental disorder according to the information, wherein the output portion outputs a result of determination regarding the presence or absence of a mental disorder performed by the analyzing portion, wherein the analyzing portion acquires information indicating either one of an appearance rate and a power of δ waves contained in sleep electroencephalogram information in a non-REM sleep period, in the sleep electroencephalogram information, and determines the presence or absence of a mental disorder according to the information, and wherein the analyzing portion performs Fourier transform to detect a δ wave component in each of at least one period forming a non-REM sleep period in the sleep electroencephalogram information, and determines that depression is not present in a case where any detected δ wave component has a power exceeding a predetermined threshold value.

19. A non-transitory computer-readable medium containing a computer program stored therein for causing a computer, which accesses a storage portion that stores sleep electroencephalogram information that is information on electroencephalograms during sleep of a test subject, to function as:

an analyzing portion that performs analysis regarding presence or absence of a mental disorder using the sleep electroencephalogram information stored in the storage portion; and an output portion that outputs a result of the analysis performed by the analyzing portion, wherein, as the analysis, the analyzing portion acquires information indicating an appearance status of any of α waves, δ waves and β waves contained in the sleep electroencephalogram information, and determines the presence or absence of a mental disorder according to the information, wherein the output portion outputs a result of determination regarding the presence or absence of a mental disorder performed by the analyzing portion, wherein the analyzing portion acquires information indicating either one of an appearance rate and a change in a waveform size of β waves contained in sleep electroencephalogram information in a REM sleep period, in the sleep electroencephalogram information, and determines the presence or absence of a mental disorder according to the information, and wherein the analyzing portion performs Fourier transform to detect a β wave component in each of multiple periods forming a REM sleep period in the sleep electroencephalogram information, and determines that depression is present in a case where an appearance rate of periods in which the β wave component is detected exceeds a predetermined threshold value.

20. A non-transitory computer-readable medium containing a computer program stored therein for causing a computer, which accesses a storage portion that stores sleep electroencephalogram information that is information on electroencephalograms during sleep of a test subject, to function as:

an analyzing portion that performs analysis regarding presence or absence of a mental disorder using the sleep electroencephalogram information stored in the storage portion; and an output portion that outputs a result of the analysis performed by the analyzing portion, wherein, as the analysis, the analyzing portion acquires information indicating an appearance status of any of α waves, δ waves and β waves contained in the sleep electroencephalogram information, and determines the presence or absence of a mental disorder according to the information, wherein the output portion outputs a result of determination regarding the presence or absence of a mental disorder performed by the analyzing portion, wherein the analyzing portion acquires information indicating either one of an appearance rate and a change in a waveform size of β waves contained in sleep electroencephalogram information in a REM sleep period, in the sleep electroencephalogram information, and determines the presence or absence of a mental disorder according to the information, and wherein the analyzing portion acquires a difference between amplitudes of adjacent waves in β waves in each of at least one period forming a REM sleep period in the sleep electroencephalogram information, and determines that depression is present in a case where any acquired difference between the amplitudes exceeds a predetermined threshold value.

21. A non-transitory computer-readable medium containing a computer program stored therein for causing a computer, which accesses a storage portion that stores sleep electroencephalogram information that is information on electroencephalograms during sleep of a test subject, to function as:

an analyzing portion that performs analysis regarding presence or absence of a mental disorder using the sleep electroencephalogram information stored in the storage portion; and an output portion that outputs a result of the analysis performed by the analyzing portion, wherein, as the analysis, the analyzing portion acquires information indicating an appearance status of any of α waves, δ waves and β waves contained in the sleep electroencephalogram information, and determines the presence or absence of a mental disorder according to the information, wherein the output portion outputs a result of determination regarding the presence or absence of a mental disorder performed by the analyzing portion, wherein the computer program further cause the computer to function as a medication determining portion that acquires information indicating an appearance status of γ waves contained in the sleep electroencephalogram information stored in the storage portion, and determines whether or not drug administration has been performed for a mental disorder according to the information, and wherein the output portion further outputs a result of determination performed by the medication determining portion.

* * * * *